US012258400B2

(12) United States Patent
Foucher et al.

(10) Patent No.: US 12,258,400 B2
(45) Date of Patent: Mar. 25, 2025

(54) ANTIBODIES HAVING SPECIFICITY FOR BTN2 AND USES THEREOF

(71) Applicants: IMCHECK THERAPEUTICS SAS, Marseilles (FR); INSERM (INSTITUT NATIONAL DE LA SANTÉ ET DE LA RECHERCHE MÉDICALE), Paris (FR); CENTRE NATIONAL DE LA RECHERCHE SCIENTIFIQUE—CNRS, Paris (FR); INSTITUT JEAN PAOLI & IRENE CALMETTES, Marseilles (FR); UNIVERSITÉ D'AIX-MARSEILLE, Marseilles (FR)

(72) Inventors: Etienne Foucher, Marseilles (FR); Carla Cano, Marseilles (FR); Kieu Suong Le, Marseilles (FR); Christine Pasero, Marseilles (FR); Daniel Olive, Marseilles (FR)

(73) Assignees: IMCHECK THERAPEUTICS SAS, Marseilles (FR); INSERM (INSTITUT NATIONAL DE LA SANTÉ ET DE LA RECHERCHE MÉDICALE), Paris (FR); CENTRE NATIONAL DE LA RECHERCHE SCIENTIFIQUE—CNRS—, Paris (FR); INSTITUT JEAN PAOLI & IRENE CALMETTES, Marseilles (FR); UNIVERSITÉ D'AIX-MARSEILLE, Marseilles (FR)

( * ) Notice: Subject to any disclaimer, the term of this patent is extended or adjusted under 35 U.S.C. 154(b) by 857 days.

(21) Appl. No.: 17/440,836

(22) PCT Filed: Mar. 20, 2020

(86) PCT No.: PCT/EP2020/057794
§ 371 (c)(1),
(2) Date: Sep. 20, 2021

(87) PCT Pub. No.: WO2020/188086
PCT Pub. Date: Sep. 24, 2020

(65) Prior Publication Data
US 2022/0162305 A1 May 26, 2022

(30) Foreign Application Priority Data

Mar. 20, 2019 (EP) ..................... 19305345
Dec. 24, 2019 (EP) ..................... 19219691

(51) Int. Cl.
*C07K 16/28* (2006.01)

(52) U.S. Cl.
CPC ...... *C07K 16/2803* (2013.01); *C07K 2317/33* (2013.01); *C07K 2317/34* (2013.01); *C07K 2317/73* (2013.01); *C07K 2317/74* (2013.01); *C07K 2317/92* (2013.01)

(58) Field of Classification Search
None
See application file for complete search history.

(56) References Cited

U.S. PATENT DOCUMENTS

2019/0023783 A1* 1/2019 Behren .............. A61K 47/6849
2023/0183346 A1 6/2023 Olive

FOREIGN PATENT DOCUMENTS

| CN | 108368171 A | 8/2018 |
|---|---|---|
| WO | 2006116192 A2 | 11/2006 |
| WO | 2009/030884 A2 | 3/2009 |
| WO | 2015/077844 A1 | 6/2015 |
| WO | 2017009258 A1 | 1/2017 |
| WO | 2019057933 A1 | 3/2019 |

OTHER PUBLICATIONS

Modern Imunology, No. 6, Nov. 30, 2009, Yang Yang et al.
Molecular cancer, vol. 22, No. 31, Feb. 15, 2023, Zhifei Gao et al.
Karunakuran, M. et al., "Butyrophilin-2A1 Directly Binds Germline-Encoded Regions of the Vg9Vd2 TCR and Is Essential for Phosphoantigen Sensing", Immunity 52, 2020.
Rigau, M. et al., "Butyrophilin 2A1 is essential for phosphoantigen reactivity by γδ T cells", Science, 2020.
Cano, C. et al., "BTN2A, a New Immune-checkpoint Targeting Vγ9Vδ2 T cell Cytotoxicity", poster, SITC annual meeting, 2019.
Smith Isobel A. et al: "BRN1A1, the Mammary Gland Butyrophilin, and BTN2A2 Are Both Inhibitors of T Cell Activation", The Journal of Immunology, the American Association of Immunologists, Inc, US, vol. 184, No. 7, Apr. 1, 2010, pp. 3514-3525.
Heather A. Arnett et al: "Immune modulation by butyrophilins", Nature Reviews Immunology, vol. 14, No. 8, Jul. 25, 2014, pp. 559-569.
Aparna Palakodeti et al: "The Molecular Basis for Modulation of Human V[gamma]9V[delta]2 T Cell Responses by CD277/Butyrophilin-3 (BTN3A)-specific Antibodies", Journal of Biological Chemistry, vol. 287, No. 39, Sep. 21, 2012, pp. 32780-32790.

* cited by examiner

Primary Examiner — Daniel E Kolker
Assistant Examiner — James Ryland Melchior
(74) Attorney, Agent, or Firm — WCF IP

(57) ABSTRACT

The present invention relates to antibodies having specificity for BTN2A and uses thereof, in particular for the treatment of cancer.

Figure 1:
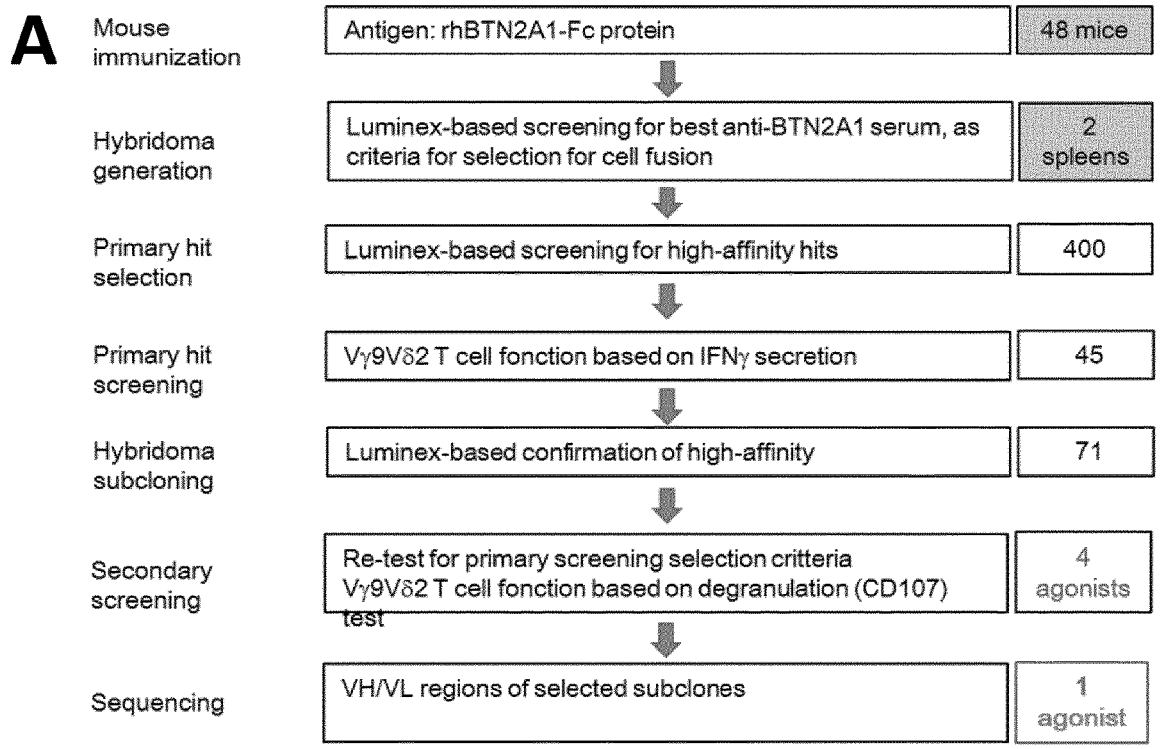
Figure 1:
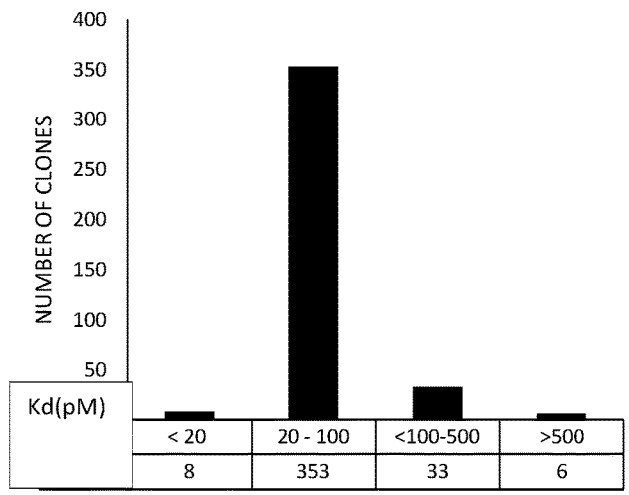
Figure 1:
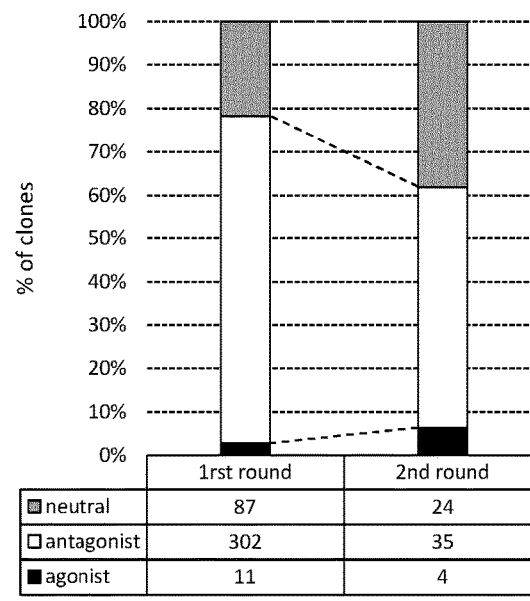

14 Claims, 30 Drawing Sheets
Specification includes a Sequence Listing.

G

H

I

A

B

ANTIBODIES HAVING SPECIFICITY FOR BTN2 AND USES THEREOF

FIELD OF THE INVENTION

The present invention relates to anti-BTN2A1 activating antibodies that bind to BTN2A1, shift macrophage population towards anti-tumoral M1 macrophages and directly activate NK cells as well as cytotoxicity against cancer cells. Alternatively, or in combination, said antibodies can activate Vγ9/Vδ2 T cells. Such antibodies are particularly useful for the treatment of cancer.

BACKGROUND

Macrophages display variable phenotypes that range from a classically activated M1 to alternative M2 types. M1 macrophages rapidly differentiate from monocytes after migration, being activated by bacterial-derived products, such as LPS (lipopolysaccharides), as well as signals associated with infections, such as IFNγ. They are highly inflammatory with high phagocytic and bactericidal potential. They secrete important pro-inflammatory cytokines such as TNFα, IL-1, IL-6, and IL-12 as well as reactive oxygen species. In contrast, M2 macrophages are present later in the healing process when granulation tissue formation occurs; they antagonize the inflammatory response, thus allowing initiation of healing. These anti-inflammatory cells recruit fibroblasts and activate them to differentiate toward myofibroblasts that release pro-angiogenic factors to recruit endothelial progenitor cells and enable new vessel formation, a process that occurs through secretion of key anti-inflammatory cytokines IL-4, IL-10, and IL-13, and are also associated with decreased production of ROS, nitric oxide (NO), and TNFα.

The tumor microenvironment (TME) strongly polarizes macrophages towards a M2-like phenotype, notably in the case of tumors recovering from cancer treatment. This polarization is not only highly pro-angiogenic but also immunosuppressive. Thus, in most solid cancers, increased infiltration with tumor-associated macrophages (TAMs) has long been associated with poor patient prognosis, highlighting their value as potential diagnostic and prognostic biomarkers in cancer.

Reprogramming and selective killing of the M2 macrophages has therefore been suggested as a promising therapeutic strategy (Zhu Y et al. Cancer Res 2014).

Furthermore, as innate immune cells, natural killer (NK) cells play pivotal functions in cancer immune surveillance. NK cells can eliminate a variety of abnormal or stressed cells without prior sensitization, and even preferentially kill stem-like cells or cancer stem cells.

Upon forming immune synapses with target cells, NK cells release preformed cytolytic granules, including perforin, and granzymes, of which function is to induce cell lysis.

Based on this postulate, several studies have successfully exploited adoptive transfer of NK cells against various tumors, especially hematological malignancies. However, cancers employ various tactics to delay, alter, or even stop anti-tumor immunity, leading to failures in the control of tumor growth. The anti-tumor response of NK cells also faces a lot of limitations. In particular, the tumor microenvironment (TME) remains a major barrier to the effectiveness of NK cells and notably adoptively transferred NK cells. For example, tumor-infiltrating immune cells such as dendritic cells (DCs), suppressive or tolerogenic macrophages and regulatory T (Treg) cells as well as cancer-associated fibroblasts, which are embedded in the extracellular matrix, may meddle in NK cell activation either through secretion of immunosuppressive cytokines or by interfering with receptor expression. For instance, in TME, TGF-β (notably secreted by M2 polarized macrophages) is recognized as a main inhibitory cytokine of NK cells which limits the number and anti-metastatic function of NK cells.

It would therefore be extremely valuable from a therapeutic point of view to have a tool that could stimulate anti-tumoral activity by both i) inhibiting the immunosuppressive effect of tumor environment and ii) directly triggering NK cell activation and mediated cytotoxicity.

Butyrophilins constitute a family of transmembrane proteins comprising butyrophilin (BTN), BTN-like (BTNL), and selection and upkeep of intraepithelial T cell (SKINT) proteins (Arnett and Viney, Nat Rev Immunol 2014). Their extracellular moieties contain IgV-like and IgC-like domains exhibiting homology to the corresponding domains of B7 co-stimulatory molecules (Arnett and Viney, 2014), and butyrophilins are thus considered to be members of the extended B7 or Ig superfamily.

The butyrophilin (BTN) family of genes is composed of 13 genes in humans, forming 8 distinct groups (Abeler-Dorner et al. Trends Immunol 2012; Afrache et al. Immunogenetics 2012). The seven human BTN genes are clustered in the MHC class I region of chromosome 6 and are divided into three subfamilies that form phylogenetically associated groups: BTN1, BTN2 and BTN3. The BTN1 subfamily contains only the prototypic single-copy BTN1A1 gene, whereas the BTN2 and BTN3 subfamilies each contain three genes BTN2A1, BTN2A2 and BTN2A3 (which is a pseudogene), BTN3A1, BTN3A2 and BTN3A3, respectively. Several gene polymorphisms have been described for BTN gene family members, which have been associated with different diseases including hypertension, chronic renal failure, inclusion body myositis, type 1 and type 2 diabetes or HCV infection (Chen et al. Int J Clin Exp Pathol, 2015; Horibe et al. Am J Hypertens, 2011 & 2014; Milman et al. Clin Respir, 2011; Murakata et al. Biomed Rep, 2014; Oguri et al. J Med Genet, 2013; Pacheco et al. Orphanet J Rare Dis, 2016). Single-nucleotide variants have been described for BTNL2, BTN2A1, BTN3A2 and BTN3A3, as well as a deleterious copy number variation involving BTNL3 and BTNL8 (Aigner et al. BMC Genet, 2013)

BTN1A1, the first butyrophilin identified, is required for the formation, secretion, and stabilization of milk fat globules (Ogg et al. Proc Natl Acad Sci, 2004). Then, it has been proposed that B7 genes and MHC class I and II genes may have a common ancestral gene and could encode for proteins involved in similar function, such as T cell activation (Rhodes et al. Genomics, 2001; Harly C et al. Blood 2012). BTN2A1 and BTN2A2 protein isoforms display an IgV and an IgC extracellular domain, a transmembrane domain, and the characteristic intracellular B30.2 domain, similar to BTN3A1 and BTN3A3, but not BTN3A2. In mouse, BTN2A2 is a single copy gene and ortholog of the human BTN2A2 gene. Recombinant human BTN2A1-Fc protein revealed that a particular glycoform of BTN2A1 binds to a lectin molecule, DC-SIGN, found on dendritic cells (DCs). Binding of BTN2A1 to DC-SIGN is dependent on high-mannose glycosylation of the protein when expressed by tumor cells (Malcherek et al. J Immunol, 2007).

Growing evidence subsequently suggested that butyrophilins play diverse roles in the immune system. RNA-seq from 53 human tissue samples from the Genotype-Tissue Expression Project (The GTEx Consortium, 2013) shows ubiquitous BTN2A1 transcript expression in normal tissue. Comparison of RNA-Seq data from GTEx and data from The Cancer Genome Atlas (TOGA) database using Gene Expression Profiling Interactive Analysis (Tang, Z. et al. Nucleic Acids Res, 2017) indicates modulation of BTN2A1 transcript expression in several cancers including cervical squamous cell carcinoma and endocervical adenocarcinoma, lung small cell carcinoma, ovarian carcinoma, pancreatic cancer and endometrial carcinoma.

Antibodies that recognize both isoforms of BTN2A have been previously reported (WO2019057933), however said antibodies inhibit the production of IFN-γ and/or TNF-α by activated Vγ9/Vδ2 T cells, and/or inhibit the cytolytic function of activated Vγ9/Vδ2 T cells, and/or inhibit the proliferation of activated Vγ9/Vδ2 T cells.

Vγ9/Vδ2 T cells are important effectors of the immune defense. They lyse directly pathogen infected or abnormal cells. In addition, they regulate immune responses by inducing dendritic cell (DC) maturation as well as the isotypic switching and immunoglobulin production. This important cell platform of the immune system is strictly regulated by surface receptors, chemokines and cytokines. Vδ9/Vδ2 T cells are activated by nonpeptidic phosphorylated isoprenoid pathway metabolites, referred to as phosphoagonists (PAg).

Development of antibodies targeting BTN2A1, and activating immune cells, notably more than one immune cell compartment, such as macrophage, NK and/or γδ T cells, in particular Vγ9/Vδ2 T cells, may be particularly relevant notably in cancer therapy and for the treatment of infectious diseases.

SUMMARY

The present disclosure provides for the first-time antibodies binding to BTN2A (notably binding the BTN2A1 isoform—e.g., the human BTN2A1 polypeptide) that exhibit at least one of the following properties:
 i. inhibit the polarization of monocytes towards M2 macrophages,
 ii. induce reversion of M2 macrophages towards antitumoral M1 macrophages,
 iii. trigger NK cell activation directly,
 iv. enhance NK cell-mediated cytotoxicity.

In particular, an antibody of the present disclosure exhibits at least one of the properties i) and ii), and at least one of properties iii) and iv), more particularly, an antibody of the present disclosure exhibits properties i) to iv).

Such antibodies according to the present disclosure can thus
 favor an anti-tumoral microenvironement by shifting macrophage phenotype and functionality towards pro-inflammatory M1 macrophages, leading to the secretion of pro-inflammatory cytokines, and/or
 trigger NK cell activation directly and thus further reinforce their cytolytic activity.

Such antibodies as per the present disclosure therefore represent powerfull tools that can be used in various strategies for cancer therapy.

In specific embodiments, anti-BTN2A antibodies of the present disclosure compete for binding to BTN2A with any one of:
 the reference murine antibody mAb 101G5 comprising (i) a heavy chain variable region comprising the amino acid sequence of SEQ ID NO:19 and (ii) a light chain variable region comprising the amino acid sequence of SEQ ID NO:20, or
 the reference murine antibody mAb 107G3 comprising (i) a heavy chain variable region comprising the amino acid sequence of SEQ ID NO:1 and a light chain variable region comprising the amino acid sequence of SEQ ID NO:2.

In some embodiments, anti BTN2A antibodies of the present disclosure bind to an epitope comprising amino acid residues located:
 in positions 65, 68, 69, 72, 78; 84, 85, 95, 97, 100 of SEQ ID No 17, or
 in positions 212, 213, 218, 220, 224, 229 of SEQ ID No 17.

In specific embodiments, anti-BTN2A antibodies of the present disclosure comprise:
 a heavy chain variable region CDR1 comprising SEQ ID NO:3, a heavy chain variable region CDR2 comprising SEQ ID NO:4, a heavy chain variable region CDR3 comprising SEQ ID NO:5, a light chain variable region CDR1 comprising SEQ ID NO:6, a light chain variable region CDR2 comprising SEQ ID NO:7, and a light chain variable region CDR3 comprising SEQ ID NO:8, or
 a heavy chain variable region CDR1 comprising SEQ ID NO:21, a heavy chain variable region CDR2 comprising SEQ ID NO:22, a heavy chain variable region CDR3 comprising SEQ ID NO:23, a light chain variable region CDR1 comprising SEQ ID NO:24, a light chain variable region CDR2 comprising SEQ ID NO:25 and a light chain variable region CDR3 comprising SEQ ID NO:26.

In specific embodiments, anti-BTN2A antibodies of the present disclosure comprise:
 a heavy chain variable region comprising a sequence having at least 90% identity with the amino acid sequence of SEQ ID NO:1 and a light chain variable region comprising a sequence having at least 90% identity with the amino acid sequence of SEQ ID NO:2, or
 a heavy chain variable region comprising a sequence having at least 90% identity with the amino acid sequence of SEQ ID NO: 19 and a light chain variable region comprising a sequence having at least 90% identity with the amino acid sequence of SEQ ID NO: 20.

In a specific embodiment, antibodies of the present disclosure further exhibit at least one of the following properties:
 activate secretion of cytolytic molecules from Vγ9Vδ2 T cells,
 activate the cytolytic function of Vγ9Vδ2 T cells, and/or
 activate the proliferation of Vγ9Vδ2 T cells.

Most particularly anti-BTN2A antibodies according to such embodiment may typically compete for binding to BTN2A with the reference murine antibody mAb 107G3 comprising (i) a heavy chain variable region comprising the amino acid sequence of SEQ ID NO:1 and (ii) a light chain variable region comprising the amino acid sequence of SEQ ID NO:2.

More specifically, such anti-BTN2A antibodies may comprise:
 a heavy chain variable region CDR1 comprising SEQ ID NO:3, a heavy chain variable region CDR2 comprising SEQ ID NO:4, a heavy chain variable region CDR3 comprising SEQ ID NO:5, a light chain variable region CDR1 comprising SEQ ID NO:6, a light chain variable region CDR2 comprising SEQ ID NO:7, and a light chain variable region CDR3 comprising SEQ ID NO:8, or a heavy chain variable region comprising a sequence having at least 90% identity with the amino acid sequence of SEQ ID NO:1 and a light chain variable region comprising a sequence having at least 90% identity with the amino acid sequence of SEQ ID NO:2, or a heavy chain variable region comprising a sequence having at least 90% identity with the amino acid sequence of SEQ ID NO:1 and a light chain variable region comprising a sequence having at least 90% identity with the amino acid sequence of SEQ ID NO:2.

In some embodiments of the present disclosure antibodies of the present disclosure have specificity for BTN2A1.

In specific embodiments, anti-BTN2A antibodies of the present disclosure are human, chimeric or humanized antibodies.

The present disclosure also encompasses nucleic acid molecules encoding a heavy chain and/or a light chain of the anti-BTN2A antibodies as described above.

The present disclosure also pertains to a host cell comprising such nucleic acids, in particular for use in the manufacturing of any one of the anti-BTN2A antibodies as described above.

Another aspect of the present disclosure relates to anti-BTN2A as described above for use in therapy, notably for the treatment of cancers or infectious diseases.

Typically, cancers as per the present disclosure includes blood cancers and solid cancers including cervical carcinomas such as squamous cell carcinoma and endocervical adenocarcinoma, ovarian carcinoma, skin cancers including squamous cell carcinoma and melanoma, lung cancers including lung small cell carcinoma, prostate cancers, colon cancers, pancreatic cancers and endometrial carcinomas and more specifically: squamous cell carcinoma and endocervical adenocarcinoma, squamous cell carcinoma, ovarian carcinoma, lung small cell carcinoma, prostate cancers, colon cancers, pancreatic cancers and endometrial carcinomas.

The present disclosure also relates to a pharmaceutical composition comprising an anti-BTN2A antibody as described above and at least a pharmaceutically acceptable carrier.

The present disclosure further provides a method for activating an immune response in a subject, comprising administering to the subject an effective amount of an anti-BTN2A as disclosed herein.

DETAILED DESCRIPTION OF THE INVENTION

Definitions

As used herein the term "BTN2" has its general meaning in the art and refers to human BTN2 polypeptides including either BTN2A1 of SEQ ID NO:17 or BTN2A2 of SEQ ID NO:18.

SEQ ID NO: 17:
BTN2A isoform 1 precursor (Homo sapiens):
MESAAALHFSRPASLLLLLLSLCALVSAQFIVVGPTDPILATVGENTTLR

CHLSPEKNAEDMEVRWFRSQFSPAVFVYKGGRERTEEQMEEYRGRTTFVS

KDISRGSVALVIHNITAQENGTYRCYFQEGRSYDEAILHLVVAGLGSKPL

-continued

ISMRGHEDGGIRLECISRGWPKPLTVWRDPYGGVAPALKEVSMPDADGLF

MVTTAVIIRDKSVRNMSCSINNTLLGQKKESVIFIPESFMPSVSPCAVAL

PIIVVILMIPIAVCIYWINKLQKEKKILSGEKEFERETREIALKELEKER

VQKEEELQVKEKLQEELRWRRTFLHAVDVVLDPDTAHPDLFLSEDRRSVR

RCPFRHLGESVPDNPERFDSQPCVLGRESFASGKHYWEVEVENVIEWTVG

VCRDSVERKGEVLLIPQNGFWTLEMHKGQYRAVSSPDRILPLKESLCRVG

VFLDYEAGDVSFYNMRDRSHIYTCPRSAFSVPVRPFFRLGCEDSPIFICP

ALTGANGVTVPEEGLTLHRVGTHQSL

SEQ ID NO: 18:
BTN2A isofom 2 precursor (Homo sapiens):
MEPAAALHFSLPASLLLLLLLLLLSLCALVSAQFTVVGPANPILAMVGEN

TTLRCHLSPEKNAEDMEVRWFRSQFSPAVFVYKGGRERTEEQMEEYRGRI

TFVSKDINRGSVALVIHNVTAQENGIYRCYFQEGRSYDEAILRLVVAGLG

SKPLIEIKAQEDGSIWLECISGGWYPEPLTVWRDPYGEVVPALKEVSIAD

ADGLFMVTTAVIIRDKYVRNVSCSVNNTLLGQEKETVIFIPESFMPSASP

WMVALAVILTASPWMVSMTVILAVFIIFMAVSICCIKKLQREKKILSGEK

KVEQEEKEIAQQLQEELRWRRTFLHAADVVLDPDTAHPELFLSEDRRSVR

RGPYRQRVPDNPERFDSQPCVLGWESFASGKHYWEVEVENVMVWTVGVCR

HSVERKGEVLLIPQNGFWTLEMFGNQYRALSSPERILPLKESLCRVGVFL

DYEAGDVSFYNMRDRSHIYTCPRSAFTVPVRPFFRLGSDDSPIFICPALT

GASGVMVPEEGLKLHRVGTHQSL

As used herein the term "antibody" or "immunoglobulin" have the same meaning and will be used equally in the present disclosure.

The term "antibody" as used herein refers to immunoglobulin molecules and immunologically active portions of immunoglobulin molecules, i.e., molecules that contain an antigen binding site that immunospecifically binds an antigen. As such, the term "antibody" encompasses not only whole antibody molecules, but also antibody fragments as well as variants (including derivatives) of antibodies and antibody fragments.

The term "antibody" as used herein also includes bispecific or multispecific molecules. An antibody can be derivatized or linked to another functional molecule, e.g., another peptide or protein (e.g., another antibody or ligand for a receptor) to generate a bispecific molecule that binds to at least two different binding sites or target molecules. The antibody may in fact be derivatized or linked to more than one other functional molecule to generate multi-specific molecules that bind to more than two different binding sites and/or target molecules; such multi-specific molecules are also intended to be encompassed by the term "bispecific molecule" as used herein. To create a bispecific molecule, an antibody of the invention can be functionally linked (e.g., by chemical coupling, genetic fusion, noncovalent association or otherwise) to one or more other binding molecules, such as another antibody, antibody fragment, peptide or binding mimetic, such that a bispecific molecule results. Additionally, for the embodiment in which the bispecific molecule is multi-specific, the molecule can further include a third binding specificity, in addition to the first and second target epitope. In one embodiment, the bispecific molecules as disclosed herein comprise as a binding specificity at least one antibody, or an antibody fragment thereof, including, e.g., an Fab, Fab', F(ab')2, Fv, Unibody or a single chain Fv. The antibody may also be a light chain or heavy chain dimer, or any minimal fragment thereof such as a Fv or a single chain construct as described in Ladner et al. U.S. Pat. No. 4,946,778.

Other antibodies which can be employed in the bispecific molecules disclosed herein are murine, chimeric and humanized monoclonal antibodies (mAbs).

The bispecific molecules of the present disclosure can be prepared by conjugating the constituent binding specificities, using methods known in the art. For example, each conjugated to one another. When the binding specificities are proteins or peptides, a variety of coupling or cross-linking agents can be used for covalent conjugation. Examples of cross-linking agents include protein A, carbodiimide, N-succinimidyl-S-acetylthioacetate (SATA), 5,5'-dithiobis(2-nitrobenzoic acid) (DTNB), o-phenylenedimaleimide (oPDM), N-succinimidyl-3-(2 pyridyldithio)propionate (SPDP), and sulfosuccinimidyl 4-(Nmaleimidomethyl) cyclohaxane-I-carboxylate (sulfo-SMCC) (Karpovsky et al., 1984; Liu et al., 1985). Other methods include those described in Brennan et al., 1985; Glennie et al., 1987; Paulus, 1985. Alternatively, both binding specificities can be encoded in the same vector and expressed and assembled in the same host cell. This method is particularly useful where the bispecific molecule is a mAb×mAb, mAb×Fab, Fab×F (ab')2 or ligand x Fab fusion protein. A bispecific molecule of the disclosure can be a single chain molecule comprising one single chain antibody and a binding determinant, or a single chain bispecific molecule comprising two binding determinants. Binding of the bispecific molecules to their specific targets can be confirmed by, for example, enzyme-linked immunosorbent assay (ELISA), radioimmunoassay (REA), FACS analysis, bioassay (e.g., growth inhibition and apoptosis), or Western Blot assay. Each of these assays generally detects the presence of protein-antibody complexes of particular interest by employing a labeled reagent (e.g., an antibody) specific for the complex of interest.

In natural antibodies, two heavy chains are linked to each other by disulfide bonds and each heavy chain is linked to a light chain by a disulfide bond. There are two types of light chain, lambda (λ) and kappa (k). There are five main heavy chain classes (or isotypes) which determine the functional activity of an antibody molecule: IgM, IgD, IgG, IgA and IgE. Each chain contains distinct sequence domains. The light chain includes two domains, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, transplacental mobility, complement binding, and binding to Fc receptors (FcR).

The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from nonhypervariable or framework regions (FR) can participate to the antibody binding site or influence the overall domain structure and hence the combining site. Complementarity Determining Regions or CDRs refer to amino acid sequences, which together define the binding affinity and specificity of the natural Fv region of a native immunoglobulin binding site. The light and heavy chains of an immunoglobulin each have three CDRs, designated L-CDR1, L-CDR2, L-CDR3 and H-CDR1, H-CDR2, H-CDR3, respectively. An antigen-binding site, therefore, typically includes six CDRs, comprising the CDRs set from each of a heavy and a light chain V region. Framework Regions (FRs) refer to amino acid sequences interposed between CDRs. According the variable regions of the light and heavy chains typically comprise 4 framework regions and 3 CDRs of the following sequence: FR1-CDR1-FR2-CDR2-FR3-CDR3-FR4.

The residues in antibody variable domains are conventionally numbered according to a system devised by Kabat et al. This system is set forth in Kabat et al., 1987, in Sequences of Proteins of Immunological Interest, US Department of Health and Human Services, NIH, USA (hereafter "Kabat et al."). This numbering system is used in the present specification. The Kabat residue designations do not always correspond directly with the linear numbering of the amino acid residues in SEQ ID sequences. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence. The CDRs of the heavy chain variable domain are located at residues 31-35 (H-CDR1), residues 50-65 (H-CDR2) and residues 95-102 (H-CDR3) according to the Kabat numbering system. The CDRs of the light chain variable domain are located at residues 24-34 (L-CDR1), residues 50-56 (L-CDR2) and residues 89-97 (L-CDR3) according to the Kabat numbering system.

In specific embodiments, an antibody provided herein is an antibody fragment, and more particularly any protein including an antigen-binding domain of an antibody as disclosed herein. Antibody fragments include, but are not limited to, Fv, Fab, F(ab')2, Fab', dsFv, scFv, sc(Fv)2 and diabodies.

An "isolated antibody", as used herein, refers to an antibody that is substantially free of other antibodies having different antigenic specificities (e.g., an isolated antibody that specifically binds to BTN2A1 is substantially free of antibodies that specifically bind to other antigens than BTN2A). An isolated antibody that specifically binds to BTN2 may, however, have cross-reactivity to other antigens, such as related BTN2 molecules from other species. Moreover, an isolated antibody may be substantially free of other cellular material and/or chemicals.

Antibody affinity refers to the strength with which the antibody binds to the epitope presented on an antigen, such as a BTN2A1 in the present disclosure, through its antigen-binding site (paratope). Affinity may be assessed based on assessment of the Kd value.

The term "$K_D$", as used herein, is intended to refer to the equilibrium dissociation constant, which is obtained from the ratio of $k_{off}$ to $k_{on}$ (i.e. $k_{off}/k_{on}$) and is expressed as a molar concentration (M). The $K_D$ value relates to the concentration of antibody (the amount of antibody needed for a particular experiment) and so the lower the $K_D$ value (lower concentration) and thus the higher the affinity of the antibody. $K_D$ values for antibodies can be determined using methods well established in the art. Preferred methods for determining the $K_D$ values of mAbs can be found in Harlow, et al., Antibodies: A Laboratory Manual, Cold Spring Harbor Laboratory Press, Cold Spring Harbor, N.Y., 1988), Coligan et al., eds., Current Protocols in Immunology, Greene Publishing Assoc. and Wiley Interscience, N.Y., 1992, 1993, and Muller, Meth Enzymol 1983, which references are entirely incorporated herein by reference. A method for determining the $K_D$ of an antibody is by using surface plasmon resonance, or by using a biosensor system such as a Biacore® (see also for detailed information regarding affinity assessment Rich R L, Day Y S, Morton T A, Myszka D G. High-resolution and high-throughput protocols for measuring drug/human serum albumin interactions using BIACORE®. Anal Biochem. 2001) or Octet® systems The Octet® platform is based on bio-layer interferometry (BLI) technology. The principle of BLI technology is based on the optical interference pattern of white light reflected from two surfaces—a layer of immobilized protein and an internal reference layer. The binding between a ligand immobilized on the biosensor tip surface and an analyte in solution produces an increase in optical thickness at the biosensor tip, which results in a shift in the interference pattern measured in nanometers. The wavelength shift ($\Delta\lambda$) is a direct measure of the change in optical thickness of the biological layer, when this shift is measured over a period of time and its magnitude plotted as a function of time, a classic association/dissociation curve is obtained. This interaction is measured in real-time, allowing to monitor binding specificity, association rate and dissociation rate, and concentration. (see Abdiche et al. 2008 but also the details in the results). Affinity measurements are typically performed at 25° C.

The term "$k_{assoc}$" or "$k_a$", or "$k_{on}$" as used herein, is intended to refer to the association rate of a particular antibody-antigen interaction, whereas the term "$k_{dis}$" or "$k_d$,", or $k_{off}$ as used herein, is intended to refer to the dissociation rate of a particular antibody-antigen interaction.

The terms "monoclonal antibody" or "monoclonal antibody composition" as used herein refer to a preparation of antibody molecules of single molecular composition. A monoclonal antibody composition displays a single binding specificity and affinity for a particular epitope.

As used herein, the term "specificity" refers to the ability of an antibody to detectably bind an epitope presented on an antigen, such as a BTN2A isoforms (including BTN2A1 and BTN2A2) in the present disclosure. It is typically intended to refer to an antibody, or protein, that binds to human BTN2A notably to BTN2A1 with a $K_D$ of 10 nM or less, 5 nM, 1 nM or less, 100 pM or less, or 10 pM or less. Typically, the $K_D$ is comprised between $10^{-3}$ pM and 10 nM, notably between 0.1 pM and 10 nM, notably between 0.1 pM and 5 nM, or between 1 pM and 10 nM notably between 1 pM and 5 nM or 10 pM and 5 nM. Typically, an antibody of the present disclosure is specific for BTN2A1 or for both BTN2A1 and BTN2A2, and has a $K_D$ as above defined. Specificity may also be assessed in some embodiments by expressing BTN2A1 in a cell line (for example HEK-293T cell lines) and by staining the transfected cells with increasing concentrations (for example ranging from 5 ng/mL to 75 µg/mL) of a purified anti-BTN2A1 mAb as herein disclosed, or with or a negative control such as its control isotype. Non-linear regression analysis of mean fluorescence intensity data allow to determine $EC_{50}$ as the concentration of mAb for which 50% of maximal fluorescence is observed. Typically, an antibody specific for BTN2A1, as per the present disclosure, binds to BTN2A1 with an $EC_{50}$ of less than 50 µg/mL, notably less than 40 µg/mL (see the Example Section), notably between 0.1 µg/mL and 50 µg/mL or between 0.5 µg/mL and 20 µg/mL.

The phrases "an antibody recognizing an antigen" and "an antibody having specificity for an antigen" are used interchangeably herein with the term "an antibody which binds specifically to an antigen".

"Selective binding" typically means that the antibody binds more strongly to a target, such as an epitope, for which it is specific as compared to the binding to another target. The antibody binds more strongly to a first target as compared to a second target if its affinity for the first target is higher than its affinity for the second target. Typically an antibody binds more strongly to a first target as compared to a second target if it binds to the first target with a equilibrium dissociation constant ($K_D$) or an $EC_{50}$ as mentioned above, that is lower than the equilibrium dissociation constant, or the $EC_{50}$, for the second target. Most specifically the agent does not bind at all to the second target to a relevant extent. In some embodiments of the present application, antibodies are selective for BTN2A and most particularly for BTN2A1. Selectivity can also be further exhibited by, e.g., an about 10:1, about 20:1, about 50:1, about 100:1, 10.000:1 or greater ratio of affinity in binding to the specific antigen versus non-specific binding to other irrelevant molecules (for example the specific antigen is a BTN2A polypeptide, notably BTN2A1 and the other "irrelevant molecule" can be for example a BTN3 isoform).

Selectivity of an antibody as herein disclosed may be tested using cross-reactivity assays to closely related other proteins (for example the BTN3 isoforms) compared with the intended target protein (BTN2A isoforms). When such cross-reactivity cannot be detected, while giving a strong signal of the intended target at the same time and at the same antibody dilution, the antibody is typically deemed selective (see the results detailed in Example corresponding to FIG. 3). An antibody that "cross-reacts with an antigen" is intended to refer to an antibody that binds that antigen with a $K_D$ of 10 nM or less, 1 nM or less, or 100 pM or less. An antibody that "does not cross-react with a particular antigen" is intended to refer to an antibody that binds to that antigen, with a $K_D$ of 100 nM or greater, or a $K_D$ of 1 µM or greater, or a $K_D$ of 10 µM or greater. In certain embodiments, such antibodies that do not cross-react with the antigen exhibit essentially undetectable binding against these proteins in standard binding assays (see typically table 3 or FIG. 3A).

In specific embodiments, the anti-BTN2A1 antibodies of the disclosure cross-react with cynomolgus BTN2A1 ortholog (cynoBTN2A1; NCBI ref. XP_015304392.1) of sequence SEQ ID No 35 as defined below:

MQRQFSKASRPCLPWVLMEPAAALHFSLPASLILLLLLLRLCALVSAQFT

VVGPTDPILAMVGENTTLRCHLSPEKNAEDMEVRWFRSQFSPAVFVYKGG

RERTEEQMEEYRGRTTFVSKDISRGSVALIIHNVTAQENGTYRCYFQEGR

SYDEAILHLMVAGLGSKPLVEMRGHEDGGIRLECISRGWYPKPLTVWRDP

YGRVVPALKEVFPPDTDGLFMVTTAVIIRDKSMRNMSCSISDTLLGQKKE

SVIFIPESFMPSVSPCVVALPIIVVFLMIIIAVCIYWINRLQKETKILSG

EKESERKTREIAVKELKKERVQKEKELQVKEQLQEELRWRRTVLHAVDVV

LDPDTAHPDLLLSEDRRSVRRCPLGHLGESVPDNPERFNSEPCVLGRESF

ASGKHYWEVEVENVIEVVTVGVCRDSVERKEEVLLRPRNGFVVTLEMCKG

-continued

QYRALSSPKRILPLKESLCRVGVFLDYEAGDVSFYNMRDRSHIYTCPRLA

FSVPVRPFFRIGSDDSPIFICPALTGASGITVPEEGLILHRVGTNQSLMP

VGTRCYGHGMRPTGFIRMREERGIHRTTREEREPDMQNFDLGAHWSNNLP

SARSREFLNSDLVPDHSLESPVTPGLANKTGEPQAEVTCLCFSLPSSELR

AFPSTATNHNHKATALGSDLHIEVKGYEDGGIHLECRSTGWYPQPQIQWS

NTKGQHIPAVKAPVVADGVGLYAVAASVIMRGSSGEGVSCIIRNSLLGLE

KTASISITDPFFRNAQPWIAALAGTLPISLLLLAGASYFLWRQQKEKIAL

SRETEREREMKEMGYAATKQEISLRGGEKSLAYHGTHISYLAAPERWEMA

VFPNSGLPRCLLTLILLQLPKLDSAPFDVIGPPEPILAVVGEDAELPCRL

SPNASAEHLELRWFRKKVSPAVLVHRDGREQEAEQMPEYRGRATLVQDGI

AEGRVALRIRGVRVSDDGEYTCFFREDGSYEEALVHLKVAALGSDPHISM

QVQENGEIWLECTSVGWYPEPQVQWRTSKGEKFPSTSESRNPDEEGLFTV

AASVIIRDTSVKNVSCYIQNLLLGQEKEVEIFIPG.

In some of these embodiments, an antibody as herein disclosed binds the cynoBTN2A1 ectodomain with an $EC_{50}$ which is comparable (more or less 10%) to the corresponding $EC_{50}$ obtained on huBTN2A1.

The term "identity" refers to the sequence similarity between two polypeptide molecules or between two nucleic acid molecules. When a position in both compared sequences is occupied by the same base or same amino acid residue, then the respective molecules are identical at that position. The percentage of identity between two sequences corresponds to the number of matching positions shared by the two sequences divided by the number of positions compared and multiplied by 100. Generally, a comparison is made when two sequences are aligned to give maximum identity. The identity may be calculated by alignment using, for example, the GCG (Genetics Computer Group, Program Manual for the GCG Package, Version 7, Madison, Wis.) pileup program, or any of sequence comparison algorithms such as BLAST, FASTA or CLUSTALW.

A functional variant of the reference molecule according to the present disclosure exhibits functional properties that are substantially equal or superior to the corresponding functional properties of the reference molecule (e.g.: the 107G3 mAb). By substantially equal it is herein intended that said functional variant retains at least about 50%, 60%, 70%, 80%, 90%, 95% or 100% of the corresponding functional property of the reference molecule.

In one aspect, the present disclosure relates to an antibody having specificity for BTN2A1 as above defined. Typically, such an antibody is characterized in that it binds to human BTN2A1 with a $K_D$ of 10 nM or less as above defined.

In some embodiments antibodies of the present disclosure do not cross-react with BTN3 isoforms.

An antibody having specificity for BTN2A, and notably BTN2A1, as per the present invention is also typically further characterized in that it has at least one of the following properties:
  i. it inhibits the polarization of monocytes towards M2 macrophages,
  ii. it induces reversion of M2 macrophages towards anti-tumoral M1 macrophages,
  iii. it triggers direct NK cells activation,
  iv. it enhances NK cell-mediated cytotoxicity.

Preferably an antibody of the present disclosure, exhibits at least one of properties i and ii and at least one of properties iii and iv, most probably it exhibits properties i to iv.

The anti-BTN2A antibodies of the present disclosure having such advantageous properties can be screened among anti-BTN2A antibodies using for example the assays as detailed in the Example section. Said assays and their implementation are briefly described below.

In the macrophage polarization assay, M2 macrophages are generated from macrophages as classically done in the field, in the presence of an anti-BTN2A antibody, notably an anti-BTN2A1 antibody as previously defined, or in the presence of a negative control such as its control isotype. GM-CSF (Granulocyte-macrophage colony-stimulating factor) and IFN-γ can be added to monocytes during M-CSF (macrophage colony-stimulating factor)-induced M2 polarization as a control for M2 differentiation inhibition. At the opposite, M1 macrophages polarized in the presence of GM-CSF can also typically be used as phenotype control. After polarization, the expression of M1 and M2-related markers at the plasma membrane can be assessed in the resulting macrophages by flow cytometry.

M1 markers that can be conveniently detected as per the present disclosure non-limitatively include PDL1, CD86, CD40, CD80, and/or SOCS3. PDL1 and/or CD86 are typically detected. M2 markers that can be conveniently detected as per the present disclosure non-limitatively include CD14, CD163, CD206 and CD209, CD14 and/or CD163 are typically detected.

Typically, inhibition of the polarization of monocytes towards M2 macrophages is induced by an anti-BTN2A of the present disclosure when:
  a significant increase in at least one M1 marker is observed, when M2 macrophages are generated in the presence of an anti-BTN2A antibody of the present disclosure, as compared to its control isotype; and/or
  a significant decrease in at least one M2 marker is observed, when M2 macrophages are generated in the presence of the anti-BTN2A antibody, as compared to its negative control such as its control isotype.

Furthermore, the cytokine secretion profile (including notably the M2-related anti-inflammatory IL-10 cytokine and the pro-inflammatory M1-related TNFα cytokine) that is a characteristic discriminating function between M1 and M2 macrophages can be quantified in culture supernatants, typically by using appropriate commercial kits (e.g., ELISA-like kits). Further cytokines that can also be easily detected to characterize the M1 or M2 macrophage phenotype include IL-1, IL-6, IL-12 and IL-23 for M1 related cytokines and TGFβ and IL-10 for M2-related cytokines.

Thus, in some embodiments, inhibition of the polarization of monocytes towards M2 macrophages can also be considered to result from the action of an anti-BTN2A antibody of the present disclosure when:
  a significant decrease of secretion of at least one M2-related cytokine is observed, when M2 macrophages are cultured in the presence of an anti-BTN2A antibody of the present disclosure, as compared to a negative control such as its control isotype and/or
  a significant increase of secretion of at least one M1-related cytokine is observed, when M2 macrophages are cultured in the presence of an anti-BTN2A antibody of the present disclosure, as compared to a negative control such as its control isotype.

Typically, an anti-BTN2A antibody as per the present disclosure can dose-dependently inhibit the polarization of monocytes towards M2 macrophages as assessed by the decreased expression of M2-related markers (such as CD14 and/or CD163) and/or the decreased secretion of M2-related cytokines (such as IL-10). Half maximum inhibitory concentration ($IC_{50}$) of such an antibody with regards to the secretion of said at least one M2-related cytokine or to the expression of said at least one M2-related marker can be determined in a dose-response curve as detailed in the Example Section. In some specific embodiments, an anti-BTN2A antibody of the present invention exhibits:
- an $IC_{50}$ for M2-related marker expression (typically CD14 and/or CD163) ranging from 0.05 µg/mL notably from 0.1 µg/mL to 100 µg/mL, notably to 50 µg/mL, and/or
- an $IC_{50}$ for M2 related cytokine secretion (typically IL-10) ranging from 0.01 µg/mL notably from 0.05 µg/mL to 100 µg/mL, notably to 50 µg/mL, most particularly from 0.1 to 20 µg/mL.

In addition, or alternatively, an anti-BTN2A antibody as per the present disclosure can dose-dependently skew the polarization of monocytes towards M1 macrophages in spite of M2-promoting stimulations, as assessed by the increased expression of M1 related markers (such as CD86 and/or PDL1) and/or decreased secretion of M2-related cytokines (such as IL-10). Half maximum effective concentration ($EC_{50}$) of such an antibody with regards to the secretion of said at least one M1-related cytokine or to the expression of said at least one M1-related marker can be determined in a dose-response curve as detailed in the Example Section. In some specific embodiments, an anti-BTN2A antibody of the present invention exhibits:
- an $EC_{50}$ for M1-related marker expression (typically CD86 and/or PDL1) ranging from 0.01 µg/mL notably from 0.1 µg/mL to 100 µg/mL, notably to 50 µg/mL, most particularly from 1 to 50 µg/mL and/or
- an $EC_{50}$ for M1-related cytokine secretion (typically TNFα) ranging from 0.01 µg/mL notably from 0.05 µg/mL to 100 µg/mL, notably to 50 µg/mL, most particularly from 0.1 to 10 µg/mL.

In the M2 macrophage reversion assay, M2 macrophages, typically generated from monocytes in presence of M-CSF, can be cultured with or without lipopolysaccharide (LPS) in the presence of an anti-BTN2A antibody (most particularly an anti-BTN2A1 antibody as previously defined) or with a negative control such as its control isotype. GM-CSF (Granulocyte-macrophage colony-stimulating factor) and IFNγ can be added to the M2 culture as a positive control of M2 reversion. M1 macrophages polarized in the presence of GM-CSF can typically be used as a phenotype control. After the reversion experiment, macrophages reverted in the absence of LPS can be analysed by flow cytometry for expression of M1- or M2-related markers as described above. Cytokine secretion can also be quantified as above described.

Typically, the reversion of M2 macrophages towards M1 macrophages is induced by an anti-BTN2A antibody of the present disclosure when:
- a significant increase in M1 markers is observed when M2 macrophages are cultured in the presence of said anti-BTN2A antibody as compared to its control isotype and/or
- a significant decrease in M2 markers is observed when M2 macrophages are cultured in the presence of said anti-BTN2A antibody as compared to a negative control such as its control isotype.

Natural killer (NK) cell activation can be assessed by cultivating NK cells (typically from healthy donors) with an anti-BTN2A antibody as herein defined or with a control isotype for negative control, with or without addition of IL-2 and/or IL-15. After at least 48 hours, notably at least 4 days, NK cells can then be extracellularly phenotyped for their activation markers, such as CD69 and/or CD25. Typically NK cell activation is considered induced by an anti-BTN2A antibody of the present disclosure when a significant increase of NK cell activation markers, such as CD69 and/or CD25, is observed in the presence of said anti-BTN2A (with or without further activation with IL-2 and/or IL-15) as compared to a negative control, such as its isotype control. The results as provided herein clearly demonstrate that antibodies of the present invention trigger direct activation of NK cells.

Enhancement of NK cell cytotoxicity can further be assessed in vitro by assessing NK cell degranulation. In such functional assay, a cancer cell line, such as a leukemia cell line (myelogenous leukemia) or a carcinoma (e.g., colon carcinoma, breast or lung adenocarcinoma) cell line is co-cultivated in the presence of the above described NK cells (previously activated with an anti-BTN2A antibody or its negative control as above described) and in the presence or absence of IL-2 and/or IL-15. NK cell degranulation can be typically assessed by flow cytometry as the percentage of CD107 positive NK cells (in the presence or absence of IL-2 and/or IL-15).

Typically, NK cell cytotoxicity is considered induced by an anti-BTN2A antibody when NK cell degranulation (e.g., the percentage of CD107 positive NK cells) is significantly increased after NK cell activation with said anti-BTN2A antibody as compared to its negative control such as its control isotype. Typically also, an anti-BTN2A antibody of the present disclosure dose-dependently induces NK cell degranulation (notably against various cancer cell lines as previously described). Half effective concentration ($EC_{50}$) of such an antibody with regard to NK cell degranulation can be determined in a dose-response curve as detailed in the Example Section.

The reference antibody 101G5 and or 107G3 can be used as positive control in the functional assays as above described.

In some embodiments, the anti-BTN2A antibodies of the present disclosure inhibit the polarization of monocytes towards M2 macrophages, induce reversion of M2 macrophages towards anti-tumoral M1 macrophages, trigger direct NK cell activation, and/or enhance NK cell-mediated cytotoxicity to a level that is substantially equal or superior to the reference antibody mAb 101G5 or mAb 107G3 as fully described below. By "inhibit the polarization of monocytes towards M2 macrophages, induce reversion of M2 macrophages towards anti-tumoral M1 macrophages, trigger direct NK cell activation, and/or enhance NK cell-mediated cytotoxicity to a level that is substantially equal or superior to the reference antibody" it is herein intended that a variation of less than 20%, notably less than 15%, notably less than 10% and typically less than 5% of the tested functional activity, is observed with the tested anti-BTN2A1 antibody as compared to any one of the reference mAb 107G3 or 101G5.

The present disclosure also encompasses an antibody
1) having specificity for BTN2A, and notably BTN2A1, as previously defined, in particular an antibody having at least one of the following properties:
   it binds to human BTN2A1, as typically expressed in a cell line, for example HEK293T cell lines transfected with a plasmid encoding human BTN2A1, as described in the examples, more specifically with an $EC_{50}$ below 50 µg/mL and more specifically below 40 µg/mL or it binds to BTN2A1 with a $K_D$ of 10 nM or less and/or it has an about 10:1, about 20:1, about 50:1, about 100:1, 10.000:1 or greater ratio of affinity in binding BTN2A1 versus non-specific binding;
it does not cross-react with BTN3;
and,
2) which further, or alternatively, exhibits one or more of the functional properties:
it activates the production of cytolytic molecules (notably IFN-γ) by Vγ9/Vδ2 T cells, and/or
it activates the cytolytic function of Vγ9/Vδ2 T cells, and/or
it activates the proliferation of Vγ9/Vδ2 T cells.

It is noticed that, proliferation, cytolytic function, and production of cytolytic molecules (notably notably IFN-γ) by Vγ9/Vδ2 T cells is achieved by activated Vγ9/Vδ2 T cells, which is typically achieved by an antibody as herein disclosed.

The anti-BTN2A1 antibodies of the present disclosure having such advantageous properties can be screened from among anti-BTN2A1 antibodies using the cellular assays as described in the Examples and in particular, by ELISA-based assessment of IFNγ secretion by Vγ9/Vδ2 T cells, and/or the CD107 degranulation assay on various cancer cell lines such as Daudi cell line, Jurkat cell line, L-IPC cell line or MDA-MB-134 cell line.

Cytolytic molecules as per the present disclosure typically consist in IFNγ or TNFα cytokines.

As used herein, by "activating the production of cytolytic molecules" (typically in IFNγ an/or TNFα), it is meant that a significant increase of the production of at least IFNγ or TNFα by activated Vγ9/Vδ2 T cells is observed when compared to control activated Vγ9/Vδ2 T cells (with IgG1 or hybridoma culture medium as control), said Vγ9/Vδ2 T cells being activated either by co-culture with target cell line (Daudi, Jurkat, L-IPC or MDA-MB-134 cell lines) or by phosphoantigens (pAg). Typically, the activation of the production of IFNγ or TNFα by activated Vγ9/Vδ2 T cells may be measured in a cellular assay by intracellular labelling with antibodies against IFNγ or TNFα assessed on flow cytometry, or by an ELISA-based dosage of IFNγ or TNFα secreted by Vγ9/Vδ2 T cells in their culture medium. Such assay is described in more details in the examples (see Material and Methods section) below.

As used herein, by "activating the cytolytic function of activated Vγ9/Vδ2 T cells", it is meant that a significant increase of the cytolytic function of activated human Vγ9/Vδ2 T cells is observed when compared to control activated human Vγ9/Vδ2 T cells (with IgG1 or hybridoma culture medium as control), said human Vγ9/Vδ2 T cells being activated either by co-culture with target cell line (Daudi, Jurkat, L-IPC or MDA-MB-134 cell lines) or phosphoantigens (pAg). Typically, the activation of the cytolytic function of activated Vγ9/Vδ2 T cells may be measured according to the measurement of the activation of the induction of Vγ9/Vδ2 T cells degranulation against a standard cell line, using CD107a and CD107b jointly, as degranulation marker for detecting positive degranulated Vγ9/Vδ2 T cells. Phorbol 12-myristate 13-acetate (PMA) with ionomycine treatment of Vγ9/Vδ2 T cells can typically be used as a positive control for Vγ9/Vδ2 T cell activation. Such an assay is described in more details in the examples below.

As used herein, by "activating the proliferation of activated Vγ9/Vδ2 T cells", it is meant that a significant increase of the proliferation of activated Vγ9/Vδ2 T cells is observed when compared to the proliferation with Vγ9/Vδ2 T cells activated with IgG1 as control, said Vγ9/Vδ2 T cells being activated either by co-culture with target cell line (such as Daudi, Jurkat, L-IPC or MDA-MB-134 cell lines) or by phosphoantigens (pAg). Typically, the proliferation of activated Vγ9/Vδ2 T cells may be measured in a cellular assay by CFSE or Cell Trace violet staining and flow cytometry of purified Vγ9/Vδ2 T cells from peripheral blood and flow cytometry, or by monitoring the expansion of the Vγ9/Vδ2 T cell compartment within peripheral blood mononuclear cells with or without stimulus.

In some embodiments, the anti-BTN2A1 antibodies of the present disclosure activate the cytolytic function of activated Vγ9/Vδ2 T cells to a level that is substantially equal or superior to the reference antibody mAb 107G3 as described below. By "activating the cytolytic function of activated Vγ9/Vδ2 T cells to a level that is substantially equal to the reference antibody" it is herein intended that a variation of less than 15%, notably less than 10% and typically less than 5% of the cytolytic function of activated Vγ9/Vδ2 T cells, is observed with the tested anti-BTN2A1 antibody as compared to the reference mAb 107G3.

In some embodiments, the anti-BTN2A1 antibodies of the present disclosure activate the production of cytolytic molecules (i.e.: at least IFNγ or TNFα) by activated Vγ9/Vδ2 T cells to a level that is substantially equal or superior to the reference antibody mAb 107G3 as described below. By "activating the production of at least IFNγ or TNFα by activated Vδ9/Vδ2 T cells to a level that is substantially equal to the reference antibody" it is herein intended that a variation of less than 15%, notably less than 10% and typically less than 5% of the cytolytic molecule production of activated Vδ9/Vδ2 T cells, is observed with the tested anti-BTN2A1 antibody as compared to the reference mAb 107G3.

In some embodiments, the anti-BTN2A1 antibodies of the present disclosure activate the cytolytic function of activated Vδ9/Vδ2 T cells to a level that is substantially equal or superior to the reference antibody mAb 107G3 as described below. By "activating the cytolytic function of activated Vδ9/Vδ2 T cells to a level that is substantially equal to the reference antibody" it is herein intended that a variation of less than 15%, notably less than 10% and typically less than 5% of the cytolytic function of activated Vδ9/Vδ2 T cells, is observed with the tested anti-BTN2A1 antibody as compared to the reference mAb 107G3.

Reference Antibodies Mabs 101G5, 107G3 and Variants Thereof

Antibodies as herein disclosed include the reference monoclonal antibodies mAb 101G5, comprising the respective VH and VL regions as defined in SEQ ID NO:19 and 20 respectively, and mAb 107G3, comprising the respective VH and VL regions as defined in SEQ ID NO:1 and 2 respectively.

Other antibodies of the disclosure include those having at least 90%, notably at least, 95, 96, 97, 98, 99 or 100 percent identity with the VH and VL regions as defined in SEQ ID NO:1 and 2 respectively or as defined in SEQ ID 19 and 20 respectively.

In particular embodiments, an anti-BTN2A antibody according to the present disclosure, typically a humanized anti-BTN2A1, comprises a heavy chain variable region CDR1 comprising SEQ ID NO:3, a heavy chain variable region CDR2 comprising SEQ ID NO:4, a heavy chain variable region CDR3 comprising SEQ ID NO:5, a light chain variable region CDR1 comprising SEQ ID NO:6, a light chain variable region CDR2 comprising SEQ ID NO:7, and a light chain variable region CDR3 comprising SEQ ID NO:8. In specific embodiments of antibodies as herein disclosed, the 6 CDR regions are 100% identical to the 6 CDR regions of the reference mAb 107G3, defined in SEQ ID NO:3-8.

In other specific embodiments, an anti-BTN2A1 antibody according to the present disclosure, typically a humanized anti-BTN2A1, comprises a heavy chain variable region CDR1 comprising SEQ ID NO:21, a heavy chain variable region CDR2 comprising SEQ ID NO:22, a heavy chain variable region CDR3 comprising SEQ ID NO:23, a light chain variable region CDR1 comprising SEQ ID NO:24 a light chain variable region CDR2 comprising SEQ ID NO:25, and a light chain variable region CDR3 comprising SEQ ID NO:26.

In specific embodiments of antibodies as herein disclosed, the 6 CDR regions are 100% identical to the 6 CDR regions of the reference mAb 101G5 defined in SEQ ID NO:21-26. Other antibodies as disclosed herein include those having amino acids that have been mutated by amino acid deletion, insertion or substitution, yet have at least 60, 70, 80, 90, 95, 96, 97, 98, 99 or 100 percent identity in the CDR regions with the CDR regions of the reference mAb 101G5. Typically, as per the present disclosure, antibodies may have between 1, 2, 3 or 4 amino acid variations (including deletion, insertion or substitution) in one or more CDRs, as compared to the CDR sequences of the reference antibody mAb 107G3, defined in SEQ ID NO:21-26.

In other specific embodiments of antibodies as herein disclosed, the 6 CDR regions are 100% identical to the 6 CDR regions of the reference mAb 107G3, defined in SEQ ID NO:3-8. Other antibodies as disclosed herein include those having amino acids that have been mutated by amino acid deletion, insertion or substitution, yet have at least 60, 70, 80, 90, 95, 96, 97, 98, 99 or 100 percent identity in the CDR regions with the CDR regions of the reference mAb 107G3. Typically as per the present disclosure, antibodies may have between 1, 2, 3 or 4 amino acid variations (including deletion, insertion or substitution) in one or more CDRs, as compared to the CDR sequences of the reference antibody mAb 107G3, defined in SEQ ID NO:3-8.

In some embodiments, the antibody of the present disclosure is a mutant variant of mAb 101G5 or of mAb 107G3, having the 6 CDR regions 100% identical to the corresponding 6 CDR regions of the reference mAb 101G5 or 107G3 respectively, and wherein said mutant variant antibody include mutant amino acid sequences wherein no more than 1, 2, 3, 4 or 5 amino acids have been mutated by amino acid deletion, insertion or substitution in the FR1, FR2, FR3 and FR4 regions when compared with the corresponding framework regions of the corresponding reference antibody.

Functional Variant Antibodies

As shown by the experimental data provided in the examples, the reference mAb 107G3 binds residues on positions: 65, 68, 69, 72, 78; 84, 85, 95, 97, 100 of the human BTN2A1.

Thus the present disclosure encompasses mAbs that bind a conformational epitope comprising amino acid residues located in positions 60 to 100 of SEQ ID No 17, and most particularly, a conformational epitope comprising amino acid residues on positions: 65, 68, 69, 72, 78; 84, 85, 95, 97, 100 of SEQ ID No 17 and that have one or more of the functional properties as previously defined and as further reminded below, in particular that have one or more of the functional properties of the reference mAb 107G3.

As also shown by the experimental data provided in the examples, the reference mAb 101G5 binds residues on positions 212, 213, 218, 220, 224, 229 of BTN2A1. Thus the present disclosure encompasses mAbs that bind a conformational epitope comprising amino acid residues located in positions 210 to 230 of SEQ ID No 17, and most particularly a conformational epitope comprising residues on positions 212, 213, 218, 220, 224, 229 of SEQ ID No 17 and that have one or more of the functional properties as previously defined and as further reminded below, in particular that have one or more of the functional properties of the reference mAb 101G5.

In yet other embodiments, a functional variant antibody of the disclosure has full length heavy and light chain amino acid sequences; or variable region heavy and light chain amino acid sequences, or all 6 CDR regions amino acid sequences that are homologous or more specifically identical to the corresponding amino acid sequences of any one of the reference antibody mAb 101G5 or mAB 107G3 described above and wherein such functional variant antibodies retain the desired functional properties of said reference antibody.

A functional variant of the reference mAb 101G5 antibody or of the reference antibody mAb 107G3, notably a functional variant of a VL, VH, or CDR used in the context of a monoclonal antibody of the present disclosure still allows the antibody to retain at least a substantial proportion (at least about 50%, 60%, 70%, 80%, 90%, 95% or 100%) of the affinity (typically assessed by $K_D$ as measured by surface plasmon resonance (SPR), or by using the Octet® platform based on bio-layer interferometry (BLI) technology, typically performed at 25° C., and/or the selectivity of the parent antibody (e.g.: mAb 101G5 or 107G3) and in some cases such a monoclonal antibody of the present disclosure may be associated with greater affinity, selectivity and/or specificity than the parent Ab (e.g.: mAb 101G5 or 107G3).

Desired functional properties, of the reference mAb 101G5 or 107G3 or of a variant of said reference antibody as herein disclosed, may be selected from the group consisting of:

i. specificity for BTN2A1, in particular the property of binding to human BTN2A1 as expressed in a cell line, for example HEK-293T BTN2 KO cells transfected with a plasmid encoding human BTN2A1, as described in the examples, more specifically with an $EC_{50}$ below 50 µg/mL and more specifically below 40 µg/mL or with a $K_D$, as measured by surface plasmon resonance (SPR) (typically at 25° C.), or Luminex assay (as illustrated in the Examples) or Octet® (Abdiche et al. 2008) of 10 nM or less and/or it has an about 10:1, about 20:1, about 50:1, about 100:1, 10.000:1 or greater ratio of affinity in binding BTN2A1 versus non-specific binding; and/or ii. inhibition of the polarization of monocytes towards M2 macrophages, assessed as typically illustrated in the Example section, and/or iii. induction of reversion of M2 macrophages towards anti-tumoral M1 macrophages, assessed as typically illustrated in the Example section, and/or iv. direct triggering of NK cell activation, assessed as typically illustrated in the Example section, and/or v. enhancement of NK cell-mediated cytotoxicity, assessed as typically illustrated in the Example section.

In some more specific embodiments, desired functional properties, of the reference mAb 107G3 or of a variant of said reference antibody as herein disclosed, may further be selected from the group consisting of:

vi. activation of cytolytic molecules (e.g.: IFNγ or TNFα) production from Vγ9/Vδ2 T cells, typically assessed as illustrated in the Examples, vii. activation of the cytolytic function of Vγ9/Vδ2 T cells, typically assessed as illustrated in the Examples; and/or viii. activation of the proliferation of Vγ9/Vδ2 T cells, typically assessed as illustrated in the Examples.

Typically, functional properties according to points (ii) to (v) above of a functional variant of the reference mAb 101G5 or 107G3 are substantially equal or superior to the corresponding functional properties of the corresponding reference antibody mAb 101G5 or 107G3 as described above. By substantially equal it is herein intended that the functional variant retains at least about 50%, 60%, 70%, 80%, 90%, 95%, 96%, 97%, 98%, 99% or 100% of the corresponding functional property of the reference mAb 107G3.

Typically, functional properties according to points (vi) to (viii) above of a functional variant of the reference mAb 107G3 are substantially equal or superior to the corresponding functional properties of the reference antibody mAb 107G3 as described above. By substantially equal it is herein intended that the functional variant retains at least about 50%, 60%, 70%, 80%, 90%, 95%, 96%, 97%, 98%, 99% or 100% of the corresponding functional property of the reference mAb 107G3.

For example, the present disclosure relates to functional variant antibodies of the reference mAb 101G5, comprising a variable heavy chain ($V_H$) and a variable light chain ($V_L$) sequences where the CDR sequences, i.e., the 6 CDR regions; HCDR1, HCDR2, HCDR3, LCDR1, LCDR2, LCDR3 share at least 60, 70, 90, 95 or 100 percent sequence identity to the corresponding CDR sequences of the mAb 101G5 reference antibody, as defined in SEQ ID NO:21-26, wherein said functional variant antibody specifically binds to BTN2A, and the antibody exhibits at least one of the following functional properties i) to iv):

i. it inhibits the polarization of monocytes towards M2 macrophages,
ii. it induces reversion of M2 macrophages towards anti-tumoral M1 macrophages,
iii. it triggers direct NK cells activation,
iv. it enhances NK cell-mediated cytotoxicity.

Preferably it exhibits at least one of properties i) and ii) and at least one of properties iii and iv), most preferably it exhibits properties i)-iv).

The present disclosure also relates to functional variant antibodies of the reference mAb 107G3, comprising a variable heavy chain ($V_H$) and a variable light chain ($V_L$) sequences where the CDR sequences, i.e., the 6 CDR regions; HCDR1, HCDR2, HCDR3, LCDR1, LCDR2, LCDR3 share at least 60, 70, 90, 95 or 100 percent sequence identity to the corresponding CDR sequences of the mAb 107G3 reference antibody, as defined in SEQ ID NO:3-8, wherein said functional variant antibody specifically binds to BTN2A1, and the antibody exhibits at least one of the following functional properties:

i. it inhibits the polarization of monocytes towards M2 macrophages,
ii. it induces reversion of M2 macrophages towards anti-tumoral M1 macrophages,
iii. it triggers direct NK cell activation,
iv. it enhances NK cell-mediated cytotoxicity,
v. it activates production of IFNγ or TNFα of Vγ9/Vδ2 T cells,
vi. it activates the cytolytic function of Vγ9/Vδ2 T cells,
vii. it activates the proliferation of Vγ9/Vδ2 T cells.

Preferably said functional variants exhibit at least one of the functional activities i) to iv) (preferably at least activities i and/or ii, and iii and/or iv) and at least one of the functional activities v) to vii).

It further relates to functional variant antibodies of the mAb 101G5 reference antibody comprising a heavy chain variable region and a light chain variable region that are at least 80%, 90%, or at least 95, 96%, 97%, 98%, 99% or 100% identical to the corresponding heavy and light chain variable regions of said mAb 101G5 reference antibody, as defined respectively in SEQ ID NO: 19 and 20; the functional variant antibody specifically binds to BTN2, and exhibits at least one of the following functional properties:

i. it inhibits the polarization of monocytes towards M2 macrophages,
ii. it induces reversion of M2 macrophages towards anti-tumoral M1 macrophages,
iii. it triggers direct NK cell activation,
iv. it enhances NK cell-mediated cytotoxicity.

Preferably it exhibits at least one of properties i) and ii) and at least one of properties iii and iv), most preferably it exhibits properties i)-iv).

It further relates to functional variant antibodies of the mAb 107G3 reference antibody comprising a heavy chain variable region and a light chain variable region that are at least 80%, 90%, or at least 95, 96%, 97%, 98%, 99% or 100% identical to the corresponding heavy and light chain variable regions of said mAb 107G3 reference antibody, as defined respectively in SEQ ID NO: 1 and 2; the functional variant antibody specifically binds to BTN2A, and exhibits at least one of the following functional properties:

i. it inhibits the polarization of monocytes towards M2 macrophages,
ii. it induces reversion of M2 macrophages towards anti-tumoral M1 macrophages,
iii. it triggers direct NK cell activation, and/or
iv. it enhances NK cell-mediated cytotoxicity.
v. it activates production of cytolytic molecules (IFNγ or TNFα) by Vγ9/Vδ2 T cells,
vi. it activates the cytolytic function of Vγ9/Vδ2 T cells, and/or,
vii. it activates the proliferation of Vγ9/Vδ2 T cells.

In some embodiments, said functional variants exhibit at least one of the functional activities i) to iv) (notably at least activities i and/or ii, and iii and/or iv) and at least one of the functional activities v) to vii).

In some embodiments, said functional variants exhibit one or more of the functional activities i to iv or one or more of the functional activities v to vii.

Typically, functional properties according to points (i) to (iv) above of a functional variant of the reference mAb 101G5 or 107G3 are substantially equal or superior to the corresponding functional properties of the corresponding reference antibody mAb 101G5 or 107G3 as described above. By substantially equal it is herein intended that the functional variant retains at least about 50%, 60%, 70%, 80%, 90%, 95%, 96%, 97%, 98%, 99% or 100% of the corresponding functional property of the reference mAb 107G3.

In various embodiments, the antibody may exhibit one or more of the desired functional properties discussed above.

The antibody can be, for example, a human antibody, a humanized antibody or a chimeric antibody. Typically, the antibody or protein is a humanized antibody, more specifically a humanized silent antibody.

As used herein, the term "silent" antibody refers to an antibody that exhibits no or low ADCC activity as measured in an in vitro ADCC activity assay measuring cell lysis of target cells.

In one embodiment, the term "no or low ADCC activity" means that the silent antibody exhibits an ADCC activity that is at below 50%, for example below 10% of the ADCC activity that is observed with the corresponding wild type (non silent) antibody for example with a wild type human IgG1 antibody. Typically, no detectable ADCC activity is observed in an in vitro ADCC activity assay with a silent antibody as compared to a control Fab antibody.

Silenced effector functions can be obtained by mutation in the Fc constant part of the antibodies and have been described in the Art: Strohl 2009 (LALA & N297A); Baudino 2008, D265A (Baudino et al., J. Immunol. 2008, Strohl), CO Biotechnology 20 2009). Examples of silent IgG1 antibodies comprise mutations reducing ADCC at positions 234, 235 and/or 331 in the IgG1 Fc amino acid sequence (EU numbering). Another silent IgG1 antibody comprises the N297A mutation, which results in a glycosylated or non-glycosylated antibody.

The sequences of CDR variants may differ from the sequence of the CDRs of the parent antibody sequences through mostly conservative substitutions; for instance, at least 10, such as at least 9, 8, 7, 6, 5, 4, 3, 2 or 1 of the substitutions in the variant are conservative amino acid residue replacements. In the context of the present disclosure, conservative substitutions may be defined by substitutions within the classes of amino acids reflected as follows:

Aliphatic residues I, L, V, and M
Cycloalkenyl-associated residues F, H, W, and Y
Hydrophobic residues A, C, F, G, H, I, L, M, R, T, V, W, and Y
Negatively charged residues D and E
Polar residues C, D, E, H, K, N, Q, R, S, and T
Positively charged residues H, K, and R
Small residues A, C, D, G, N, P, S, T, and V
Very small residues A, G, and S
Residues involved in turn A, C, D, E, G, H, K, N, Q, R, S, P, and formation T
Flexible residues Q, T, K, S, G, P, D, E, and R More conservative substitutions groupings include: valine-leucine-isoleucine, phenylalanine-tyrosine, lysine-arginine, alanine-valine, and asparagine-glutamine. Conservation in terms of hydropathic/hydrophilic properties and residue weight/size also is substantially retained in a variant CDR as compared to a CDR of the any one of mAbs 1-6. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophane (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). The retention of similar residues may also or alternatively be measured by a similarity score, as determined by use of a BLAST program (e.g., BLAST 2.2.8 available through the NCBI using standard settings BLOSUM62, Open Gap=I I and Extended Gap=I). Suitable variants typically exhibit at least about 80% of identity to the parent peptide. According to the present disclosure a first amino acid sequence having at least 70% of identity with a second amino acid sequence means that the first sequence has 70; 71; 72; 73; 74; 75; 76; 77; 78; 79; 80; 81; 82; 83; 84; 85; 86; 87; 88; 89; 90; 91; 92; 93; 94; 95; 96; 97; 98; 99; or 100% of identity with the second amino acid sequence. According to the present disclosure a first amino acid sequence having at least 50% of identity with a second amino acid sequence means that the first sequence has 50; 51; 52; 53; 54; 55; 56; 57; 58; 59; 60; 61; 62; 63; 64; 65; 66; 67; 68; 69; 70; 71; 72; 73; 74; 75; 76; 77; 78; 79; 80; 81; 82; 83; 84; 85; 86; 87; 88; 89; 90; 91; 92; 93; 94; 95; 96; 97; 98; 99; or 100% of identity with the second amino acid sequence.

In some embodiments, the antibody of the present disclosure is a chimeric antibody, typically a chimeric mouse/human antibody. The term "chimeric antibody" refers to a monoclonal antibody, which comprises a VH domain and a VL domain of an antibody derived from a non-human animal, a CH domain and a CL domain of a human antibody. As the non-human animal, any animal such as mouse, rat, hamster, rabbit or the like can be used. In particular, said mouse/human chimeric antibody may comprise the VH and the VL domains of any one of the mAb 101G5 or the mAb 107G3 reference antibodies.

In some embodiments, the antibody of the present disclosure is a humanized antibody. In specific embodiments, the antibody of the present disclosure is a humanized antibody, which comprises the 6 CDRs of any one of the mAb 101G5 or mAb 107G3 reference antibodies. As used herein the term "humanized antibody" refers to antibodies in which the framework regions (FRs) have been modified to comprise the FRs from a donor immunoglobulin of different species (for example human species) as compared to that of the parent immunoglobulin (for example murine CDRs).

In some embodiments, the antibody of the present disclosure is selected from the group consisting of Fab, F(ab')2, Fab' and scFv. As used herein, the term "Fab" denotes an antibody fragment having a molecular weight of about 50,000 and antigen binding activity, in which about a half of the N-terminal side of H chain and the entire L chain, among fragments obtained by treating IgG with a protease, papaine, are bound together through a disulfide bond. The term "F(ab')2" refers to an antibody fragment having a molecular weight of about 100,000 and antigen binding activity, which is slightly larger than the Fab bound via a disulfide bond of the hinge region, among fragments obtained by treating IgG with a protease, pepsin. The term "Fab'" refers to an antibody fragment having a molecular weight of about 50,000 and antigen binding activity, which is obtained by cutting a disulfide bond of the hinge region of the F(ab')2. A single chain Fv ("scFv") polypeptide is a covalently linked VH:VL heterodimer which is usually expressed from a gene fusion including VH and VL encoding genes linked by a peptide-encoding linker. The human scFv fragment of the disclosure includes CDRs that are held in appropriate conformation, typically by using gene recombination techniques.

Functional variant antibodies with mutant amino acid sequences can be obtained by mutagenesis (e.g., site-directed or PCR-mediated mutagenesis) of the coding nucleic acid molecules, followed by testing of the encoded altered antibody for retained function (i.e., the functions set forth above) using the functional assays described herein.

Antibodies that Cross-Compete the Reference 101G5 or 107G3 mAbs

Additional antibodies with similar advantageous properties of the reference mAb 101G5 or the reference mAb 107G3 as disclosed herein can be identified based on their ability to cross-compete with (e.g., to competitively inhibit the binding of), in a statistically significant manner, said reference mAb 107G3 as described above, in standard BTN2A1 binding assays.

Test antibodies may first be screened for their binding affinity to BTN2A1, for example from human recombinant antibody libraries using for example phage display technologies or from transgenic mouse expressing human variable region antibodies immunized with BTN2A1 antigens as assessed typically in the Examples (see Material and Methods section).

In another embodiment, the disclosure provides antibodies that bind to the same epitope as do at least the reference mAb 107G3 or the reference mAb 101G5 as described above. As illustrated in the Example section, the reference mAbs 101G5 and 107G3 do not bind the same epitope on BTN2A1.

The ability of a test antibody to cross-compete with, or inhibit the binding of antibodies of the present disclosure to human BTN2A1, demonstrates that the test antibody can compete with that antibody for binding to human BTN2A1; such an antibody may, according to non-limiting theory, bind to the same or a related (e.g., a structurally similar or spatially proximal) epitope on human BTN2A1 as the antibody with which it competes.

For example, the following test can be used to screen an anti-BTN2A1 antibody for its ability to cross-compete with mAb 107G3 reference antibody and/or to screen an anti-BTN2A1 antibody for its ability to binds to the same epitope as said reference antibody: BTN2KO cells transfected with human BTN2A1 (typically HEK293T as described in the examples) can be stained with saturing concentration (e.g., 10 μg/mL) of the reference antibody mAb 107G3. Different doses of a test anti-BTN2A1 mAbs can then be tested for their competitive potential with the mAb 107G3 reference antibody. The mAbs that do compete with the reference antibody will not be able to recognize BTN2A1 in the presence of such reference antibody. The data can be expressed as mean fluorescence intensity. Alternatively, competition assay can be performed in a binning assay as described in the Example section. Typically, binning experiment can be performed by immobilizing recombinant human BTN2A1 on a Biosensor and by presenting the reference antibody followed by the competing antibody.

The selected antibodies can be further tested for the advantageous properties of mAb 101G5 or mAb 107G3 in particular as previously detailed.

Accordingly, in one embodiment, the present disclosure provides an isolated antibody which compete for binding to the reference mAb 101G5 or the reference mAb 107G3, from binding to BTN2A1, wherein
said antibody:
  i. has specificity for BTN2A1, in particular it binds to human BTN2A1 as expressed in a cell line, for example HEK-293T BTN2 KO cells transfected with human BTN2A1, as described in the examples, more specifically with an $EC_{50}$ below 50 μg/mL and more specifically below 40 μg/mL or with a $K_D$ as measured by surface plasmon resonance (SPR), or Luminex assay (as illustrated in the Examples) or Octet® assay, of 10 nM or less and/or it has an about 10:1, about 20:1, about 50:1, about 100:1, 10.000:1 or greater ratio of affinity in binding BTN2A1 versus non-specific binding (see also above for more details); and/or
  ii. it inhibits the polarization of monocytes towards M2 macrophages,
  iii. it induces reversion of M2 macrophages towards anti-tumoral M1 macrophages,
  iv. it triggers direct NK cell activation, and/or
  v. it enhances NK cell-mediated cytotoxicity.
Alternatively, or Further, Said Antibody:
  vi. activates production of cytolytic molecules (e.g.: IFNγ or TNFα) by Vδ9/Vδ2 T cells, typically assessed as illustrated in the Examples; and/or
  vii. activates the cytolytic function of Vδ9/Vδ2 T cells, typically assessed as illustrated in the Examples; and/or
  viii. activates the proliferation of Vδ9/Vδ2 T cells, typically assessed as illustrated in the Examples.

More specifically in such embodiments, said antibody does not cross-react with BTN3.

Typically, functional properties according to points (iii) to (v) above of an antibody that compete for binding to BTN2A1 with the reference mAb 101G5 or 107G3 are substantially equal or superior to the corresponding functional properties of the reference antibody mAb 101G5 or 107G3 as described above. By substantially equal it is herein intended that the functional variant retains at least about 50%, 60%, 70%, 80%, 90%, 95% or 100% of the corresponding functional property of the reference mAb 101G5 or mAb 107G3.

Typically, an antibody that compete for binding to BTN2A1 with the reference mAb 107G3 according to the present disclosure still to retain at least a substantial proportion (at least about 50%, 60%, 70%, 80%, 90%, 95% or 100%) of the affinity and/or the selectivity of the reference antibody (e.g.: mAb 107G3) and in some cases may be associated with greater affinity, selectivity and/or specificity than the reference antibody (e.g.: mAb 107G3).

In a certain embodiment, the cross-blocking antibodies or antibody that competes for binding to BTN2A1 with the reference mAb 101G5 or 107G3, is a chimeric, humanized or human recombinant antibody.

Generation of Transfectomas Producing Monoclonal Antibodies

The antibodies of the present disclosure are produced by any techniques known in the art, such as, without limitation, any chemical, biological, genetic or enzymatic technique, either alone or in combination. Typically, knowing the amino acid sequence of the desired sequence, one skilled in the art can readily produce said antibodies, by standard techniques for production of polypeptides. For instance, they can be synthesized using well-known solid phase method, typically using a commercially available peptide synthesis apparatus (such as that made by Applied Biosystems, Foster City, Calif.) and following the manufacturer's instructions. Alternatively, antibodies of the present disclosure can be synthesized by recombinant DNA techniques well-known in the art. For example, antibodies can be obtained as DNA expression products after incorporation of DNA sequences encoding the antibodies into expression vectors and introduction of such vectors into suitable eukaryotic or prokaryotic hosts that will express the desired antibodies, from which they can be later isolated using well-known techniques.

Accordingly, a further object of the present disclosure relates to a nucleic acid molecule encoding an antibody as herein disclosed. More particularly the nucleic acid molecule encodes a heavy chain or a light chain of an antibody of the present disclosure. More particularly the nucleic acid molecule comprises a VH or VL coding region having at least 70%, 80%, 90%, 95% or 100% of identity to the corresponding nucleic acid encoding heavy chain variable region (VH region) or light chain variable region (VL) of any one of the reference antibody mAb 107G3.

Typically, said nucleic acid is a DNA or RNA molecule, which may be included in any suitable vector, such as a plasmid, cosmid, episome, artificial chromosome, phage or a viral vector. As used herein, the terms "vector", "cloning vector" and "expression vector" mean the vehicle by which a DNA or RNA sequence (e.g. a foreign gene) can be introduced into a host cell, to transform the host and promote expression (e.g. transcription and translation) of the introduced sequence. Thus, a further object of the present disclosure relates to a vector comprising a nucleic acid as herein disclosed. Such vectors may comprise regulatory elements, such as a promoter, enhancer, terminator and the like, to cause or direct expression of said antibody upon administration to a subject. Examples of promoters and enhancers used in the expression vector for animal cell include early promoter and enhancer of SV40, LTR promoter and enhancer of Moloney mouse leukemia virus, promoter and enhancer of immunoglobulin H chain and the like. Any expression vector for an animal cell can be used, so long as a gene encoding the human antibody C region can be inserted and expressed. Examples of suitable vectors include pAGE107, pAGE103, pHSG274, pKCR, pSG1 beta d2-4 and the like. Other examples of plasmids include replicating plasmids comprising an origin of replication, or integrative plasmids, such as for instance pUC, pcDNA, pBR, and the like. Other examples of viral vector include adenoviral, retroviral, herpes virus and AAV vectors. Such recombinant viruses may be produced by techniques known in the art, such as by transfecting packaging cells or by transient transfection with helper plasmids or viruses.

Typical examples of virus packaging cells include PA317 cells, PsiCRIP cells, GPenv+ cells, 293 cells, etc. Detailed protocols for producing such replication-defective recombinant viruses may be found for instance in WO 95/14785, WO 96/22378, U.S. Pat. Nos. 5,882,877, 6,013,516, 4,861,719, 5,278,056 and WO 94/19478.

A further object of the present disclosure relates to a host cell, which has been transfected, infected or transformed by a nucleic acid and/or a vector as described above. As used herein, the term "transformation" means the introduction of a "foreign" (i.e. extrinsic or extracellular) gene, DNA or RNA sequence into a host cell, so that the host cell will express the introduced gene or sequence to produce a desired substance, typically a protein or enzyme coded by the introduced gene or sequence. A host cell that receives and expresses introduced DNA or RNA has been "transformed".

The nucleic acids as herein disclosed may be used to produce an antibody of the present disclosure in a suitable expression system. The term "expression system" means a host cell and compatible vector under suitable conditions, e.g. for the expression of a protein coded for by foreign DNA carried by the vector and introduced to the host cell. Common expression systems include *E. coli* host cells and plasmid vectors, insect host cells and Baculovirus vectors, and mammalian host cells and vectors. Other examples of host cells include, without limitation, prokaryotic cells (such as bacteria) and eukaryotic cells (such as yeast cells, mammalian cells, insect cells, plant cells, etc.). Specific examples include *E. coli, Kluyveromyces* or *Saccharomyces* yeasts, mammalian cell lines (e.g., HEK-293 cells, Vero cells, CHO cells, 3T3 cells, COS cells, etc.) as well as primary or established mammalian cell cultures (e.g., produced from lymphoblasts, fibroblasts, embryonic cells, epithelial cells, nervous cells, adipocytes, etc.). Examples also include mouse SP2/0-Ag14 cell (ATCC CRL1581), mouse P3X63-Ag8.653 cell (ATCC CRL1580), CHO cell in which a dihydrofolate reductase gene (hereinafter referred to as "DHFR gene") is defective (Urlaub G et al; 1980), rat YB2/3HL.P2.G11.16Ag.20 cell (ATCC CRL1662, hereinafter referred to as "YB2/0 cell"), and the like.

The present disclosure also relates to a method of producing a recombinant host cell expressing an antibody as herein disclosed, said method comprising the steps of: (i) introducing in vitro or ex vivo a recombinant nucleic acid or a vector as described above into a competent host cell, (ii) culturing in vitro or ex vivo the recombinant host cell obtained and (iii), optionally, selecting the cells which express and/or secrete said antibody. Such recombinant host cells can be used to produce antibodies of the present disclosure.

Antibodies of the present disclosure are suitably separated from the culture medium by conventional immunoglobulin purification procedures such as, for example, protein A-Sepharose, hydroxylapatite chromatography, gel electrophoresis, dialysis, or affinity chromatography.

In some embodiments, the human chimeric antibody of the present disclosure can be produced by obtaining nucleic sequences encoding VL and VH domains as previously described, constructing a human chimeric antibody expression vector by inserting them into an expression vector for animal cell having genes encoding human antibody CH and human antibody CL, and expressing the coding sequence by introducing the expression vector into an animal cell. As the CH domain of a human chimeric antibody, it may be any region, which belongs to human immunoglobulin, but those of IgG class are suitable and any one of subclasses belonging to IgG class, such as IgG1, IgG2, IgG3 and IgG4, can also be used. Also, as the CL of a human chimeric antibody, it may be any region, which belongs to Ig, and those of kappa class or lambda class can be used. Methods for producing chimeric antibodies involve conventional recombinant DNA and gene transfection techniques are well known in the art (See Morrison S L. et al. (1984) and patent documents U.S. Pat. Nos. 5,202,238 and 5,204,244).

The humanized antibody of the present disclosure may be produced by obtaining nucleic acid sequences encoding CDR domains, as previously described, constructing a humanized antibody expression vector by inserting them into an expression vector having genes encoding (i) a heavy chain constant region and heavy chain variable framework regions identical to that of a human antibody and (ii) a light chain constant region and light chain variable framework regions identical to that of a human antibody, and expressing the genes by introducing the expression vector into suitable cell line. The humanized antibody expression vector may be either of a type in which a gene encoding an antibody heavy chain and a gene encoding an antibody light chain exists on separate vectors or of a type in which both genes exist on the same vector (tandem type). In respect of easiness of construction of a humanized antibody expression vector, easiness of introduction into cell lines, and balance between the expression levels of antibody H and L chains in cell lines, humanized antibody expression vector of the tandem type is preferred. Examples of tandem type humanized antibody expression vector include pKANTEX93 (WO 97/10354), pEE18 and the like.

Methods for humanizing antibodies based on conventional recombinant DNA and gene transfection techniques are well known in the art (See, e. g., Riechmann L. et al. 1988; Neuberger M S. et al. 1985). Antibodies can be humanized using a variety of techniques known in the art including, for example, CDR-grafting (EP 239,400; PCT publication WO91/09967; U.S. Pat. Nos. 5,225,539; 5,530, 101; and 5,585,089), veneering or resurfacing (EP 592,106; EP 519,596; Padlan E A (1991); Studnicka G M et al. (1994); Roguska M A. et al. (1994)), and chain shuffling (U.S. Pat. No. 5,565,332). The general recombinant DNA technology for preparation of such antibodies is also known (see European Patent Application EP 125023 and International Patent Application WO 96/02576).

The Fab of the present disclosure can be obtained by treating an antibody which specifically reacts with AMH with a protease, papaine. Also, the Fab can be produced by inserting DNA encoding Fab of the antibody into a vector for prokaryotic expression system, or for eukaryotic expression system, and introducing the vector into a procaryote or eucaryote (as appropriate) to express the Fab.

The F(ab')2 of the present disclosure can be obtained treating an antibody which specifically reacts with AMH with a protease, pepsin. Also, the F(ab')2 can be produced by binding Fab' described below via a thioether bond or a disulfide bond.

The Fab' of the present disclosure can be obtained treating F(ab')2 which specifically reacts with AMH with a reducing agent, dithiothreitol. Also, the Fab' can be produced by inserting DNA encoding Fab' fragment of the antibody into an expression vector for prokaryote, or an expression vector for eukaryote, and introducing the vector into a prokaryote or eukaryote (as appropriate) to perform its expression.

The scFv of the present disclosure can be produced by obtaining cDNA encoding the VH and VL domains as previously described, constructing DNA encoding scFv, inserting the DNA into an expression vector for prokaryote, or an expression vector for eukaryote, and then introducing the expression vector into a prokaryote or eukaryote (as appropriate) to express the scFv.

To generate a humanized scFv fragment, the well-known technology called CDR grafting may be used, which involves selecting the complementary determining regions (CDRs) from a donor scFv fragment, and grafting them onto a human scFv fragment framework of known three dimensional structure (see, e. g., WO98/45322; WO 87/02671; U.S. Pat. Nos. 5,859,205; 5,585,089; 4,816,567; EP0173494).

Engineered antibodies of the present disclosure further include those in which modifications have been made to framework residues within VH and/or VL, e.g. to improve the properties of the antibody. Typically, such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis or PCR-mediated mutagenesis. Such "backmutated" antibodies are also intended to be encompassed by the present disclosure. Another type of framework modification involves mutating one or more residues within the framework region, or even within one or more CDR regions, to remove T cell-epitopes to thereby reduce the potential immunogenicity of the antibody. This approach is also referred to as "deimmunization" and is described in further detail in U.S. Patent Publication No. 20030153043 by Carr et al.

Fc Engineering

The antibody as herein disclosed can be characterized by one or more of the functional or structural features of the aspects described above, or by any combination of selected functional and structural features.

The antibody as herein disclosed may be of any isotype. The choice of isotype typically will be guided by the desired effector functions, such as ADCC silencing. Exemplary isotypes are IgGI, IgG2, IgG3, and IgG4. Either of the human light chain constant regions, kappa or lambda, may be used. If desired, the class of an antibody of the present disclosure may be switched by known methods. Typical, class switching techniques may be used to convert one IgG subclass to another, for instance from IgG1 to IgG2. Thus, the effector function of the antibodies of the present disclosure may be changed by isotype switching to, e.g., an IgGI, IgG2, IgG3, IgG4, IgD, IgA, IgE, or IgM antibody for various therapeutic uses. In some embodiments, the antibody as herein disclosed is a full-length antibody. In some embodiments, the full-length antibody is an IgG1 antibody. In some embodiments, the full-length antibody is an IgG4 antibody. In some embodiments, the BTN2A-specific IgG4 antibody is a stabilized IgG4 antibody. Examples of suitable stabilized IgG4 antibodies are antibodies wherein arginine at position 409 in a heavy chain constant region of human IgG4, which is indicated in the EU index as in Kabat et al. supra, is substituted with lysine, threonine, methionine, or leucine, typically lysine (described in WO2006033386) and/or wherein the hinge region comprises a Cys-Pro-Pro-Cys sequence. Other suitable stabilized IgG4 antibodies are disclosed in WO2008145142.

In some embodiments, the antibody of the present disclosure does not comprise a Fc portion that induces antibody dependent cellular cytotoxicity (ADCC). The terms "Fc domain," "Fc portion," and "Fc region" refer to a C-terminal fragment of an antibody heavy chain, e.g., from about amino acid (aa) 230 to about aa 450 of human gamma heavy chain or its counterpart sequence in other types of antibody heavy chains (e.g., α, δ, ε and p for human antibodies), or a naturally occurring allotype thereof. Unless otherwise specified, the commonly accepted Kabat amino acid numbering for immunoglobulins is used throughout this disclosure (see Kabat et al. (1991) Sequences of Protein of Immunological Interest, 5th ed., United States Public Health Service, National Institute of Health, Bethesda, Md.). In some embodiments, the antibody of the present disclosure does not comprise an Fc domain capable of substantially binding to a FcgRIIIA (CD16) polypeptide. In some embodiments, the antibody of the present disclosure lacks an Fc domain (e.g. lacks a CH2 and/or CH3 domain) or comprises an Fc domain of IgG2 or IgG4 isotype. In some embodiments, the antibody of the present disclosure consists of or comprises a Fab, Fab', Fab'-SH, F(ab')2, Fv, a diabody, single-chain antibody fragment, or a multispecific antibody comprising multiple different antibody fragments. In some embodiments, the antibody of the present disclosure is not linked to a toxic moiety. In some embodiments, one or more amino acids selected from amino acid residues can be replaced with a different amino acid residue such that the antibody has altered C2q binding and/or reduced or abolished complement dependent cytotoxicity (CDC). This approach is described in further detail in U.S. Pat. No. 6,194,551.

Another modification of the antibodies herein that is herein contemplated is pegylation. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. The pegylation can be carried out by an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (Cl—ClO) alkoxy- or aryloxy-poly ethylene glycol or polyethylene glycol-maleimide. In some embodiments, the antibody to be pegylated is an aglycosylated antibody. Methods for pegylating proteins are known in the art and can be applied to the antibodies of the present disclosure. See for example, EP 0154 316 by Nishimura et al. and EP 0 401 384 by Ishikawa et al.

Another modification of the antibodies that is herein contemplated is a conjugate or a protein fusion of at least the antigen-binding region of the antibody of the present disclosure to serum protein, such as human serum albumin or a fragment thereof to increase half-life of the resulting molecule.

In some embodiments, the present disclosure also provides a multispecific antibody. Exemplary formats for the multispecific antibody molecules of the present disclosure include, but are not limited to (i) two antibodies cross-linked by chemical heteroconjugation, one with a specificity to BTN2A and another with a specificity to a second antigen; (ii) a single antibody that comprises two different antigen-binding regions; (iii) a single-chain antibody that comprises two different antigen-binding regions, e.g., two scFvs linked in tandem by an extra peptide linker; (iv) a dual-variable-domain antibody (DVD-Ig), where each light chain and heavy chain contains two variable domains in tandem through a short peptide linkage (Wu et al., Generation and Characterization of a Dual Variable Domain Immunoglobulin (DVD-Ig™) Molecule, In: Antibody Engineering, Springer Berlin Heidelberg 2010); (v) a chemically-linked bispecific (Fab')2 fragment; (vi) a Tandab, which is a fusion of two single chain diabodies resulting in a tetravalent bispecific antibody that has two binding sites for each of the target antigens; (vii) a flexibody, which is a combination of scFvs with a diabody resulting in a multivalent molecule; (viii) a so called "dock and lock" molecule, based on the "dimerization and docking domain" in Protein Kinase A, which, when applied to Fabs, can yield a trivaient bispecific binding protein consisting of two identical Fab fragments linked to a different Fab fragment; (ix) a so-called Scorpion molecule, comprising, e.g., two scFvs fused to both termini of a human Fab-arm; and (x) a diabody. Another exemplary format for bispecific antibodies is IgG-like molecules with complementary CH3 domains to force heterodimerization. Such molecules can be prepared using known technologies, such as, e.g., those known as Triomab/Quadroma (Trion Pharma/Fresenius Biotech), Knob-into-Hole (Genentech), CrossMAb (Roche) and electrostatically-matched (Amgen), LUZ-Y (Genentech), Strand Exchange Engineered Domain body (SEEDbody)(EMD Serono), Biclonic (Merus) and DuoBody (Genmab A/S) technologies. In some embodiments, the bispecific antibody is obtained or obtainable via a controlled Fab-arm exchange, typically using DuoBody technology. In vitro methods for producing bispecific antibodies by controlled Fab-arm exchange have been described in WO2008119353 and WO 2011131746 (both by Genmab A/S). In one exemplary method, described in WO 2008119353, a bispecific antibody is formed by "Fab-arm" or "half-molecule" exchange (swapping of a heavy chain and attached light chain) between two monospecific antibodies, both comprising IgG4-like CH3 regions, upon incubation under reducing conditions. The resulting product is a bispecific antibody having two Fab arms which may comprise different sequences. In another exemplary method, described in WO 2011131746, bispecific antibodies of the present disclosure are prepared by a method comprising the following steps, wherein at least one of the first and second antibodies is the antibody of the present disclosure: a) providing a first antibody comprising an Fc region of an immunoglobulin, said Fc region comprising a first CH3 region; b) providing a second antibody comprising an Fc region of an immunoglobulin, said Fc region comprising a second CH3 region; wherein the sequences of said first and second CH3 regions are different and are such that the heterodimeric interaction between said first and second CH3 regions is stronger than each of the homodimeric interactions of said first and second CH3 regions; c) incubating said first antibody together with said second antibody under reducing conditions; and d) obtaining said bispecific antibody, wherein the first antibody is the antibody of the present disclosure and the second antibody has a different binding specificity, or vice versa. The reducing conditions may, for example, be provided by adding a reducing agent, e.g. selected from 2-mercaptoethylamine, dithiothreitol and tris(2-carboxyethyl)phosphine. Step d) may further comprise restoring the conditions to become non-reducing or less reducing, for example by removal of a reducing agent, e.g. by desalting. Typically, the sequences of the first and second CH3 regions are different, comprising only a few, fairly conservative, asymmetrical mutations, such that the heterodimeric interaction between said first and second CH3 regions is stronger than each of the homodimeric interactions of said first and second CH3 regions. More details on these interactions and how they can be achieved are provided in WO 2011131746, which is hereby incorporated by reference in its entirety. The following are exemplary embodiments of combinations of such assymetrical mutations, optionally wherein one or both Fc-regions are of the IgGI isotype.

Thus, the present disclosure proposes bispecific or multispecific antibodies (also named bi- or multispecific molecules) comprising an anti-BTN2A antibody as herein described. Accordingly, the present disclosure includes bispecific molecules comprising at least one first binding specificity for BTN2A, for example, one antigen-binding portion of an antibody as herein disclosed and a second binding specificity for a second target epitope. For example, a bispecific molecule according to the present disclosure may include one antigen binding portion comprising at least:

a heavy chain variable region CDR1 comprising SEQ ID NO:3, a heavy chain variable region CDR2 comprising SEQ ID NO:4, a heavy chain variable region CDR3 comprising SEQ ID NO:5, a light chain variable region CDR1 comprising SEQ ID NO:6, a light chain variable region CDR2 comprising SEQ ID NO:7, and a light chain variable region CDR3 comprising SEQ ID NO:8, or a heavy chain variable region CDR1 comprising SEQ ID NO:21, a heavy chain variable region CDR2 comprising SEQ ID NO:22, a heavy chain variable region CDR3 comprising SEQ ID NO:23, a light chain variable region CDR1 comprising SEQ ID NO:24 a light chain variable region CDR2 comprising SEQ ID NO:25, and a light chain variable region CDR3 comprising SEQ ID NO:26.

In one embodiment, the bispecific molecule comprises a second binding specificity for BTN3. More specifically the bispecific molecule can further include an antigen binding portion of an anti-BTN3A activating antibodies that specifically bind to BTN3A and activate the cytolytic function of Vδ9/Vδ2 T cells.

Additionally, for the embodiment in which the bispecific molecule is multi-specific, the molecule can further include a third binding specificity, in addition to the first and second target epitope.

In one embodiment, the bispecific molecules as disclosed herein comprise as a binding specificity at least one antibody, or an antibody fragment thereof, including, e.g., an Fab, Fab', F(ab')2, Fv, Unibody or a single chain Fv. The antibody may also be a light chain or heavy chain dimer, or any minimal fragment thereof such as a Fv or a single chain construct as described in Ladner et al. U.S. Pat. No. 4,946,778.

Other antibodies which can be employed in the bispecific molecules disclosed herein are murine, chimeric and humanized monoclonal antibodies.

Pharmaceutical Compositions

In another aspect, the present disclosure provides a composition, e.g., a pharmaceutical composition, containing at least one antibody as disclosed herein, formulated together with a pharmaceutically acceptable carrier. Such compositions may include one or a combination of (e.g., two or more different) antibodies as described above. Pharmaceutical compositions disclosed herein also can be administered in combination therapy, i.e., combined with other agents.

For example, an antibody of the present invention may typically be combined with at least one anti-viral, anti-inflammatory or another antiproliferative agent. Examples of therapeutic agents that can be used in combination therapy are described in greater detail below in the section on uses of the antibodies of the disclosure.

As used herein, "pharmaceutically acceptable carrier" includes any and all solvents, dispersion media, coatings, antibacterial and antifungal agents, isotonic and absorption delaying agents, and the like that are physiologically compatible. The carrier should be suitable for intravenous, intramuscular, subcutaneous, parenteral, spinal or epidermal administration (e.g., by injection or infusion). In one embodiment, the carrier should be suitable for subcutaneous route.

Depending on the route of administration, the active compound, i.e., the antibody, may be coated in a material to protect the compound from the action of acids and other natural conditions that may inactivate the compound. The form of the pharmaceutical compositions, the route of administration, the dosage and the regimen naturally depend upon the condition to be treated, the severity of the illness, the age, weight, and sex of the patient, etc.

The pharmaceutical compositions of the disclosure can be formulated for a topical, oral, parenteral, intranasal, intravenous, intramuscular, subcutaneous or intraocular administration and the like.

Uses and Methods of the Invention

The antibodies of the present disclosure have in vitro and in vivo diagnostic and therapeutic utilities. For example, these molecules can be administered to cells in culture, e.g. in vitro, ex vivo or in vivo, or in a subject, e.g., in vivo, to treat, prevent or diagnose a variety of disorders.

The antibodies of the disclosure are anti-BTN2A1 antibodies that inhibit monocyte differentiation towards pro-tumoral M2 macrophages in terms of phenotype, cytokine secretion and/or T-cell inhibitory properties.

Alternatively, or preferably in addition, the antibodies of the present disclosure bind directly to BTN2A (notably BTN2A1) at the plasma membrane of NK cells and trigger their activation and cytotoxicity against cancer cells.

In some embodiments, antibodies of the present disclosure can further activate the cytolytic function, cytokine production and proliferation of Vγ9/Vδ2 T cells.

Thereby the presently disclosed antibodies may be used to overcome the immunosuppressive mechanisms observed in cancer patients and during chronic infections.

In some embodiments, antibodies of the present disclosure, can be used to reduce immunosuppressive effect of tumor environment.

Anti-BTN2A antibodies as herein disclosed can also potentiate cytotoxic effects of both NK and/or Th1 cells by acting both on the tumor microenvironment (via M1 polarization and/or M2 inhibition) and directly on the NK cell compartment.

In some embodiments, antibodies of the present disclosure (such as the 107G3 antibody and its variants as herein described) further activate the cytolytic function, cytokine production and proliferation of Vγ9/Vδ2 T cells. Such antibodies have therefore the possibility to act in conjunction on the 3 cellular compartments of immunity: NK cells, macrophages and γδ T cells, therefore representing powerfull tools for cancer treatment, notably for solid tumor treatment.

Preclinical studies have firmly demonstrated that NK cells can kill leukemic cells of the myeloid lineage. However, in CML for example, the NK cells decrease in number along disease progression, respond less to stimuli, and exhibit reduced cytolytic activity. In AML, higher cytolytic activity of NK cells also predicts a better long-term outcome of patients at both diagnosis and in remission (Carlsten M, Järås M. Natural Killer Cells in Myeloid Malignancies: Immune Surveillance, NK Cell Dysfunction, and Pharmacological Opportunities to Bolster the Endogenous NK Cells. Front Immunol. 2019). Thus in some embodiments, antibodies of the present invention that present NK cell activating properties may be used in combination with NK cell therapies such as adoptively transferred NK cell therapy to restore NK Cell function and/or trigger or improve their cytotoxicity. In particular, antibodies of the present application may be used in the treatment of solid tumors, which are usually resistant to NK cell killing. As used herein, the terms "cancer", "hyperproliferative" and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness.

The terms "cancer" or "neoplasms" include malignancies of the various organ systems, such as affecting lung, breast, thyroid, lymphoid, gastrointestinal, and genito-urinary tract, as well as adenocarcinomas which include malignancies such as most colon cancers, squamous cell carcinoma of the lung, the skin or the vagina, renal-cell carcinoma, prostate cancer and/or testicular tumors, non-small cell carcinoma of the lung, small cell carcinoma of the lung, endometrial carcinoma, ovarian carcinoma, endocervical adenocarcinoma, pancreatic cancer, cancer of the small intestine and cancer of the esophagus and more generally any cancer that can be treated by in vivo stimulation of the activation and/or proliferation of γδT cells in a subject suffering from said cancer.

Examples of cancers include, but are not limited to, hematological malignancies such as B-cell lymphoid neoplasm, T-cell lymphoid neoplasm, non-Hodgkin lymphoma (NHL), B-NHL, T-NHL, chronic lymphocytic leukemia (CLL), small lymphocytic lymphoma (SLL), mantle cell lymphoma (MCL), NK-cell lymphoid neoplasm and myeloid cell lineage neoplasm including acute myeloid leukemia.

Examples of non-hematological cancers include, but are not limited to, colon cancer, breast cancer, lung cancer, ovarian cancer, brain cancer, prostate cancer, head and neck cancer, pancreatic cancer, bladder cancer, colorectal cancer, bone cancer, cervical cancer, liver cancer, oral cancer, esophageal cancer, thyroid cancer, kidney cancer, stomach cancer, testicular cancer and skin cancer.

Examples of chronic infections include, but are not limited to, viral, bacterial, parasitic or fungal infections such as chronic hepatitis, lung infections, lower respiratory tract infections, bronchitis, influenza, *pneumoniae* and sexually transmitted diseases.

According, the disclosure relates to a method for treating one of the disorders disclosed above, in a subject in need thereof, said method comprising a therapeutically efficient amount of an anti-BTN2A1 antibodies as disclosed above.

The antibodies for use as disclosed above may be administered as the sole active ingredient or in conjunction with, e.g. as an adjuvant to or in combination to, other drugs e.g., cytokines, anti-viral, anti-inflammatory agents or cytotoxic, anti-proliferative, chemotherapy or anti-tumor agents, cell therapy product (e.g. γδ T cell composition or NK cell composition) e.g., for the treatment or prevention of diseases mentioned above.

For example, the antibodies for use as disclosed above may be used in combination with cell therapy, in particular γδ T cell therapy, NK cell therapy, chemotherapy, antineoplastic agents, or immunotherapeutic agents.

As used herein, the term "cell therapy" refers to a therapy comprising the in vivo administration of at least a therapeutically efficient amount of a cell composition to a subject in need thereof. The cells administered to the patient may be allogenic or autologous. The term "γδ T cell therapy" refers to a cell therapy wherein the cell composition includes, as the active principle, γδ T cells, in particular Vγ9/Vδ2 T cells (such as adoptive γδ T cell transfer or chimeric antigen receptor-expressing γδ T cells). The term "NK cell therapy" refers to a cell therapy wherein the cell composition includes, as the active component, NK cells such as adoptive NK cell transfer or chimeric antigen receptor-expressing NK cells (CAR-NKs).

A cell therapy product refers to the cell composition, which is administered to said patient for therapeutic purposes. Said cell therapy product include a therapeutically efficient dose of cells and optionally, additional excipients, adjuvants or other pharmaceutically acceptable carriers.

Suitable antineoplastic agents may include without limitation, alkylating agents (such as cyclophosphamide, mechloretamine, chlorambucil, melphalan, nitrosureas, temozolomide), anthracyclines (such as daunorubicin, doxorubicin, epirubicin, idarubicin, mitoxantrone, valrubicin), taxanes (such as Paclitaxel, Docetaxel), epothilones, inhibitors of Topoisomerase I (such as Irinotecan or Topotecan), inhibitors of Topoisomerase II (such as Etoposide, teniposide, or Tafluposide), nucleotide analogs and precursor analogs (such as azacitidine, azathioprine, capecitabine, cytarabine, flurouracil, gemcitabine, hydroxyurea, mercaptopurine, methotrexate, or Tioguanine), peptide antibiotics (such as carboplatin, cisplatin and oxaliplatin), retinoids (such as tretinoin, alitretinoin, bexarotene), *vinca* alkaloids and derivatives (such as vinblastine, vincristine, vindesine, vinorelbine), targeted therapies such as kinase inhibitors (such as Ibrutinib, Idelalisib, Erlotinib, Gefitinib, Imatinib, Vemurafenib, Vismodegib), proteasome inhibitors (such as bortezomib, carfilzomib), histone deacetylase inhibitors (such as Vorinostat or Romidepsin).

Examples of immunotherapeutic agents include without limitation phosphoantigens (e.g. zoledronic acid or other bisphosphonates), anti-PD-1 antibodies, anti-PD-L1 antibodies, anti-CTLA-4 antibodies and cytokines (such as interleukin 2 (IL-2) (Choudhry H et al. 2018, Biomed Res Int.), interleukin 15 (IL-15) (Patidar M et al. Cytokine Growth Factor Rev. 2016), interleukin 21 (IL-21) (Caccamo N. et al. PLoS One. 2012), or interleukin 33 (IL-33) (Duault C et al. J Immunol. 2016), or their recombinant forms and their derivatives, or any cytokines capable of inducing lymphocyte activity (e.g. proliferation or cytokines production or metabolic changes). The term derivative is used for any cytokine modifications that can rely on PEGylation (e.g. conjugation to polyethylene glycol (PEG) chains), mutation such as amino acid deletion, substitution or insertion, or association with potentiating agents (for example IL15/IL15Ra complexes fused to an IgG1 Fc, in which IL-15 is additionally mutated (asn72asp) that further increase biological activity making this complex an IL-2 and IL-15Rβγ superagonist (Rhode P R et al, Cancer Immunol Res. 2016) (Barroso-Sousa R et al, Curr Oncol Rep. 2018).

The term "IL-2" has its general meaning and refers to the human interleukin-2. IL-2 mainly regulates lymphocyte activity by binding to IL-2 receptors.

The term "IL-15" has its general meaning and refers to the human interleukin-15. Like IL-2, IL-15 binds to and signals through a complex composed of IL-2/IL-15 receptor beta chain (CD122) and the common gamma chain (gamma-C, CD132). IL-15 regulates the activation and proliferation of T and natural killer (NK) cells.

The term "IL-21" has its general meaning and refers to the human interleukin-21. IL-21 has been ascribed to pleiotropic properties, including, but not limited to, enhancing NK cell and CD8+ T cell cytotoxicity, modulating plasma cell differentiation and inhibiting Treg cells.

The term "IL-33" has its general meaning and refers to the human interleukin-33. IL-33, considered as an alarmin released upon tissue stress or damage, is a member of the IL-1 family and binds the ST2 receptor. IL-33 is known as an effective stimulator of $T_H1$ immune cells, natural killer (NK) cells, iNKT cells, and CD8 T lymphocytes.

The term "PD-1" has its general meaning in the art and refers to the programmed death-1 receptor. The term "PD-1" also refers to a type I transmembrane protein, belonging to the CD28-B7 signalling family of receptors that includes CD28, cytotoxic T-lymphocyte-associated antigen 4 (CTLA-4), inducible costimulator (ICOS), and B- and T-lymphocyte attenuator (BTLA) (Greenwald R J et al., 2005, Riley J L et al. 2005).

The term "anti-PD-1 antibody" or "anti-PD-L1" has its general meaning in the art and refers to an antibody with binding affinity to PD-1 or PD-L1 respectively, and antagonist activity to PD-1, i.e., it inhibits the signal transduction cascade related to the PD-1 and inhibits PD-1 ligand binding (PD-L1; PD-L2). Such anti-PD-1 antibody or anti-PD-L1 antibody preferentially inactivates PD-1 with a greater affinity and potency, respectively, than its interaction with the other sub-types or isoforms of the CD28-B7 signalling family of receptors (CD28; CTLA-4; ICOS; BTLA). Tests and assays for determining whether a compound is a PD-1 antagonist are well known by the skilled person in the art such as described in Greenwald et al., 2005; Riley et al., 2005.

Examples of such anti-PD1 antibody includes without limitation, nivolumab, pembrolizumab, avelumab, durvalumab, cemiplimab, or atezolizumab.

In accordance with the foregoing the present disclosure provides in a yet further aspect:

A method as defined above comprising co-administration, e.g., concomitantly or in sequence, of a therapeutically effective amount of an anti-BTN2A1 antibody of the disclosure, and at least one second drug substance, said second drug substance being an anti-viral or anti-proliferative agent or immunotherapeutic agents, or cytokines or a cell therapy product (such as γδ T cells), e.g. as indicated above.

In one embodiment, the antibodies of the disclosure can be used to detect levels of soluble BTN2A1, or levels of cells that express BTN2A1. This can be achieved, for example, by contacting a sample (such as an in vitro sample) and a control sample with the anti-BTN2A1 antibody under conditions that allow for the formation of a complex between the antibody and BTN2A1 (as expressed at the surface of the cells or soluble BTN2A1, for example in a blood sample). Any complexes formed between the antibody and BTN2A1 are detected and compared in the sample and the control. For example, standard detection methods, well known in the art, such as ELISA and flow cytometric assays, can be performed using the compositions of the disclosure.

Accordingly, in one aspect, the disclosure further provides methods for detecting the presence of BTN2A1 (e.g., human BTN2A1 antigen) in a sample, or measuring the amount of BTN2A1, comprising contacting the sample, and a control sample, with an antibody or protein of the disclosure, or an antigen binding region thereof, which specifically binds to BTN2A1, under conditions that allow for formation of a complex between the antibody or portion thereof and BTN2A1. The formation of a complex is then detected, wherein a difference in complex formation between the sample compared to the control sample is indicative of the presence of BTN2A1 in the sample.

Also within the scope of the present disclosure are kits consisting of the compositions (e.g., humanized antibodies, conjugated antibodies and multispecific molecules) disclosed herein and instructions for use. The kit can further contain a least one additional reagent, or one or more additional antibodies or proteins. Kits typically include a label indicating the intended use of the contents of the kit. The term label includes any writing, or recorded material supplied on or with the kit, or which otherwise accompanies the kit. The kit may further comprise tools for diagnosing whether a patient belongs to a group that will respond to an anti-BTN2A1 antibody treatment, as defined above.

Another therapeutic strategy is based on the use of a humanized antibody as disclosed herein as agents, which selectively activate NK cells isolated from a sample of a human subject.

The disclosure thus relates to a method for treating a subject in need thereof, comprising:
(a) isolating blood cells comprising NK cells, for example PBMCs from a blood sample of a subject,
(b) expanding in vitro NK cells in the presence of an anti-BTN2A1 as herein disclosed and, optionally, other tumor or accessory cells,
(c) collecting the expanded NK cells,
(d) optionally, formulating the expanded NK cells and administering a therapeutically efficient amount of said NK cells to the subject.

The disclosure further relates to the use of a humanized antibody as herein disclosed as agents, which selectively activates chimeric Antigen Receptor (CAR) NK cells. CAR NK cells and their use in adoptive NK cell cancer immunotherapy are described for example in Rezvani, K et al. "Adoptive cell therapy using engineered natural killer cells" (Bone Marrow Transplant 2019).

The disclosure also relates an anti-BTN2A1 antibody as herein disclosed for use in vivo as potentiating agent in an NK cell therapy in a subject in need thereof, typically suffering from cancer.

As used herein, the term NK cell therapy refers to a therapy, which comprises the administration to a subject in need thereof of at least an efficient amount of NK cells. Such NK cells may be allogeneic or autologous. In specific embodiments, the NK cells can be genetically engineered by deletion or knockout or insertion or knock-in of specific genes. In specific embodiments, said NK cells include NK cells expressing chimeric antigen receptor. The NK cells may have been expanded and/or purified ex vivo. Alternatively, the NK cells may also be comprised in a cell composition comprising other blood cells, and for example other cells of the immune system. For references regarding γδ T cell therapy, please see Rezvani, K. Bone Marrow Transplant 2019.

The disclosure thus relates to a method of treatment of a subject suffering from cancer, e.g. hematological malignancies, in particular, leukemias such as acute myeloid leukemia, and having tumor cells, for example blood tumor cells, said method comprising:
(i) administering in said subject an efficient amount of an anti-BTN2A1 antibody as disclosed herein, and,
(ii) administering an efficient amount of NK cell composition in said subject,
wherein said efficient amount of anti-BTN2A1 antibody has the capacity to potentiate antitumor cytolysis mediated by said NK cell composition against said tumor cells. The disclosure also pertains to a method for treating a subject in need thereof, said method comprising the combined (simultaneous or sequential) administration of NK cells, for example CAR NK cells, and a humanized antibody as disclosed herein.

In alternative or additional embodiments, the therapeutic strategy can be also based on the use of a humanized antibody as disclosed herein as agents, which selectively expand and/or activate Vγ9/Vδ2 T cells isolated from a sample of a human subject.

The disclosure thus relates to a method for treating a subject in need thereof, comprising:
(a) isolating blood cells comprising Vγ9/Vδ2 T cells, for example PBMCs from a blood sample of a subject,
(b) expanding in vitro Vγ9/Vδ2 T cells in the presence of an anti-BTN2A1 as herein disclosed and, optionally, other tumor or accessory cells,
(c) collecting the expanded Vγ9/Vδ2 T cells, (d) optionally, formulating the expanded Vγ9/Vδ2 T cells and administering a therapeutically efficient amount of said Vγ9/Vδ2 T cells to the subject.

The disclosure further relates to the use of a humanized antibody as herein disclosed as agents, which selectively expand Chimeric Antigen Receptor (CAR) Vγ9Vδ2 T cells. CAR γδ T cells and their use in adoptive T cell cancer immunotherapy are described for example in Mirzaei et al, Cancer Lett 2016.

The antibodies of the present disclosure may also be used to prepare artificial T cell receptor (also known as chimeric T cell receptors, or chimeric antigen receptors (CARs)). For example, the variable regions of antibodies may be used to form a Fab or scFv which is linked via a spacer to a transmembrane domain and a signaling endodomain of a TCR and may be produced at the surface of T cells. Such CARs may be used in adoptive transfer therapy, for example for treating proliferative disorders.

The disclosure also relates an anti-BTN2A1 antibody for use in vivo as potentiating agent of tumor cells in a γδ T cell therapy in a subject in need thereof, typically suffering from cancer.

As used herein, the term γδ T cell therapy refers to a therapy, which comprises the administration to a subject in need thereof of at least an efficient amount of γδ T cells. Such γδ T cells may be allogeneic or autologous. In specific embodiments, the γδ T cells can be genetically engineered by deletion or knockout or insertion or knock-in of specific genes. In specific embodiments, said γδ T cells include γδ T cells expressing chimeric antigen receptor. The γδ T cells may have been expanded and/or purified ex vivo. Alternatively, the γδ T cells may also be comprised in a cell composition comprising other blood cells, and for example other cells of the immune system. For references regarding γδ T cell therapy, please see Pauza C D. et al, Front Immunol. 2018 J Saudemont A. et al, Frontiers Immunol 2018.

Indeed, without being bound by any particular theory, a proposed mode of action of an anti-BTN2A1 antibody of the present disclosure is that its binding to BTN2A1 expressed at the surface of a tumour cell triggers a conformational change that allows its signalling to its counter-receptor on Vγ9Vδ2 T cells.

The disclosure thus relates to a method of treatment of a subject suffering from cancer, e.g. hematological malignancies, in particular, leukemias such as acute myeloid leukemia, and having tumor cells, for example blood tumor cells, said method comprising:
  (i) administering in said subject an efficient amount of an anti-BTN2A1 antibody as disclosed herein, and,
  (ii) administering an efficient amount of γδ T cell composition in said subject, wherein said efficient amount of anti-BTN2A1 antibody has the capacity to potentiate antitumor cytolysis mediated by said γδ T cell composition against said tumor cells. The disclosure also pertains to a method for treating a subject in need thereof, said method comprising the combined (simultaneous or sequential) administration of CAR T cells, for example CAR γδ T cells, and an humanized antibody as disclosed herein.

The invention will be further illustrated by the following figures and examples. However, these examples and figures should not be interpreted in any way as limiting the scope of the present disclosure.

LEGENDS OF THE FIGURES

FIG. 1. Identification of anti-BTN2A1 107G3 mAb. A. Screening cascade of anti-BTN2A1 mAbs from mice immunization to mAb sequencing. B. Bar chart shows the number of clones per affinity ($K_D$) range as measured on Luminex during primary hit selection. C. Stacked bar chart shows the number of clones classified as neutral (grey), antagonist (white) or agonist (black) according to their ability to modulate IFN-γ production by Vγ9/Vδ2 T cells during primary (1rst round) and secondary (2nd round) hit screening.

Figure 2:
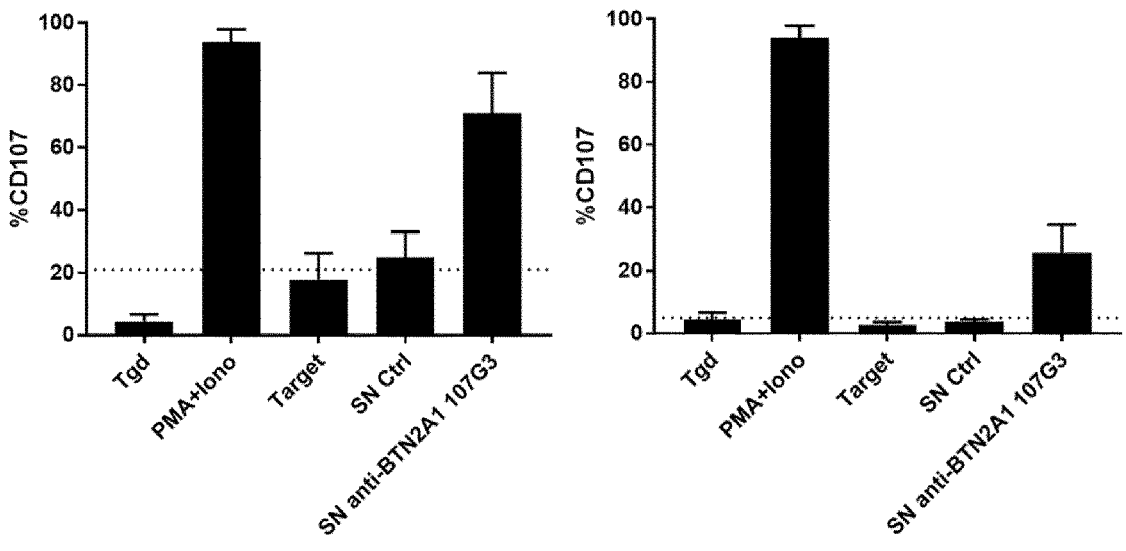
Figure 2:
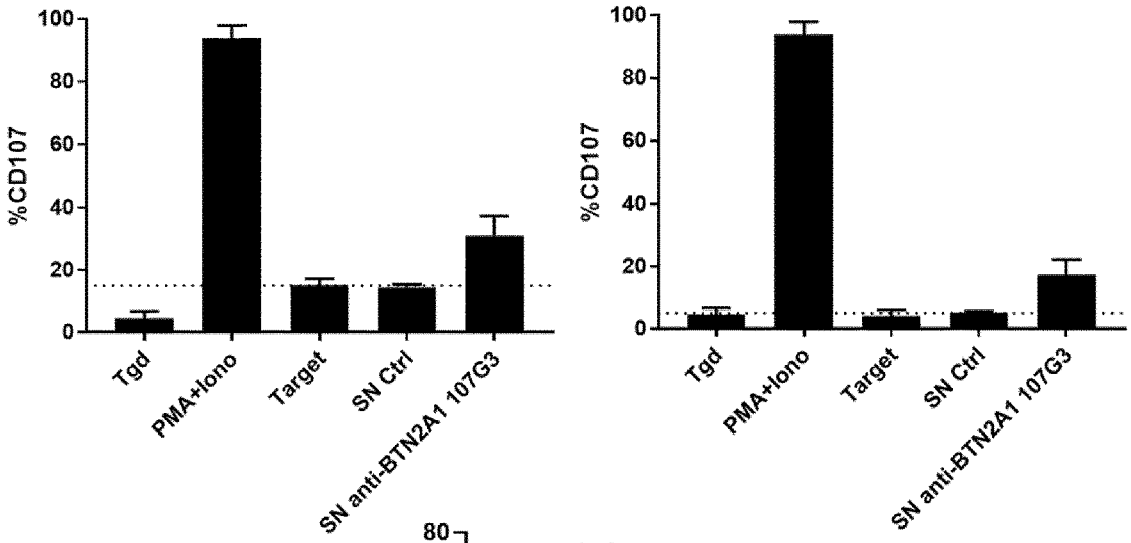
Figure 2:
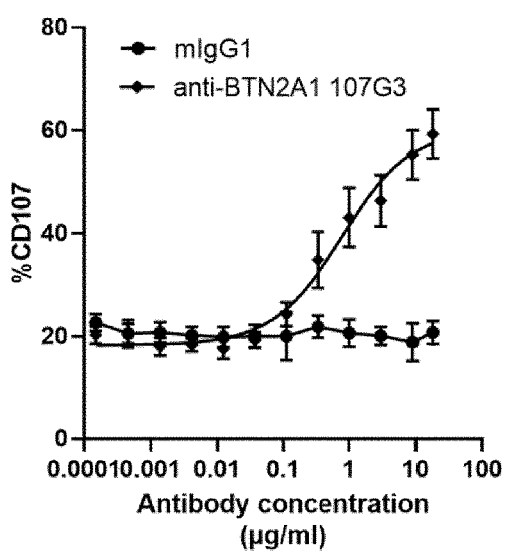

FIG. 2. Anti-BTN2A1 107G3 mAb enhances the cytolytic function of Vγ9/Vδ2 T cells. Vγ9/Vδ2 T cells were expanded from PBMCs of 3 healthy donors (see Material and Methods), and co-cultured at 37° C. with target cells using and effector: target (E:T) ratio of 1:1, in presence of anti-CD107a/b antibodies and Golgi stop, with or without the indicated antibodies. After 4 h, cells were collected, fixed and analyzed on flow cytometry. In A, different target cell lines were used including Daudi (Burkitt's lymphoma), Jurkat (acute T cell leukemia), L-IPC (pancreatic adenocarcinoma) and MDA-MB-134 (breast carcinoma), with or without anti-BTN2A1 107G3 supernatant or control hybridoma culture medium. Bar charts show the percentage of CD107+ cells depicting Vγ9/Vδ2 T cell degranulation. In B Daudi cells were used as target cells, in the presence of the indicated concentrations of purified anti-BTN2A1 107G3 mAb or irrelevant mouse IgG1, as isotype control. Graph shows dose-response curve allowing for $EC_{50}$ calculation.

Figure 3:
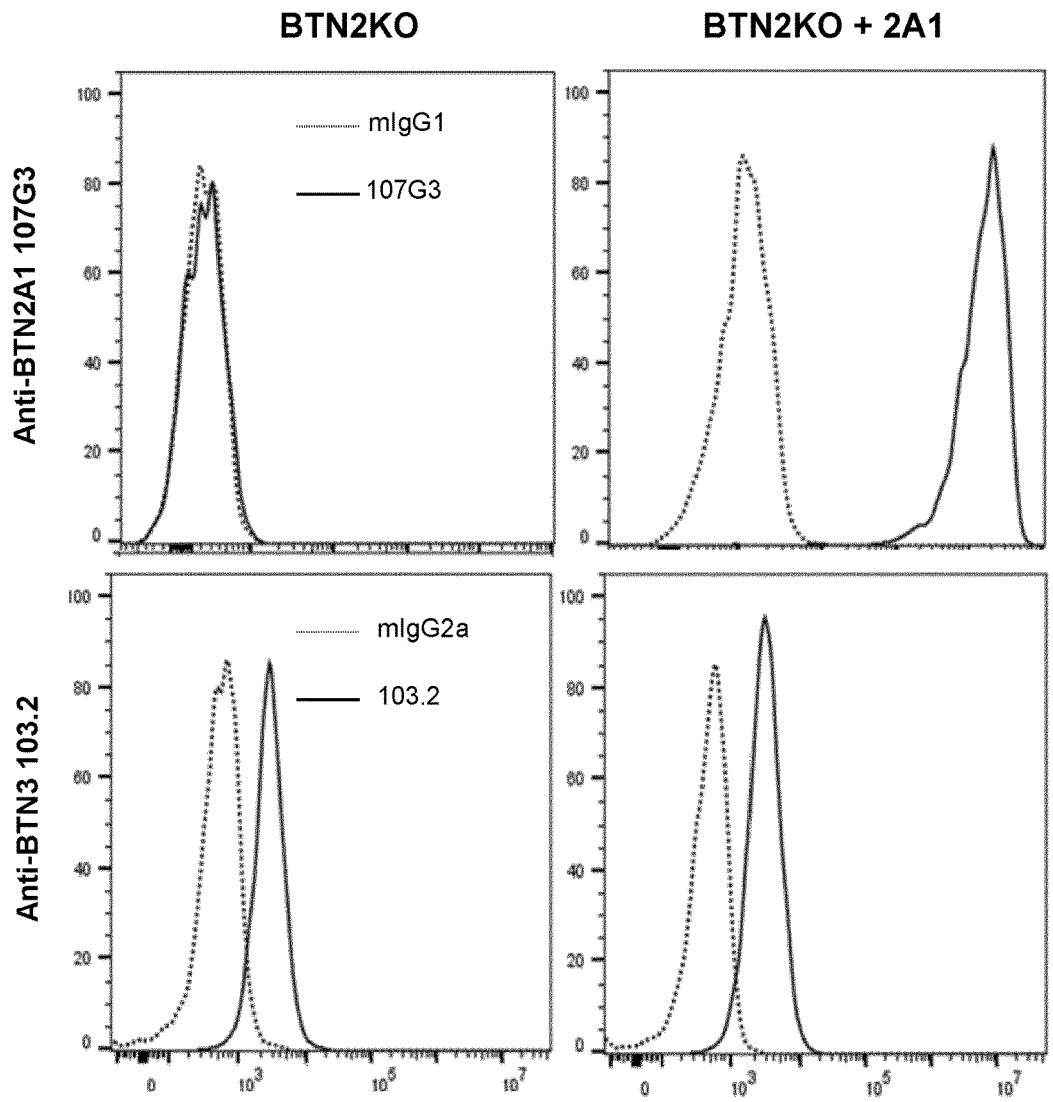
Figure 3:
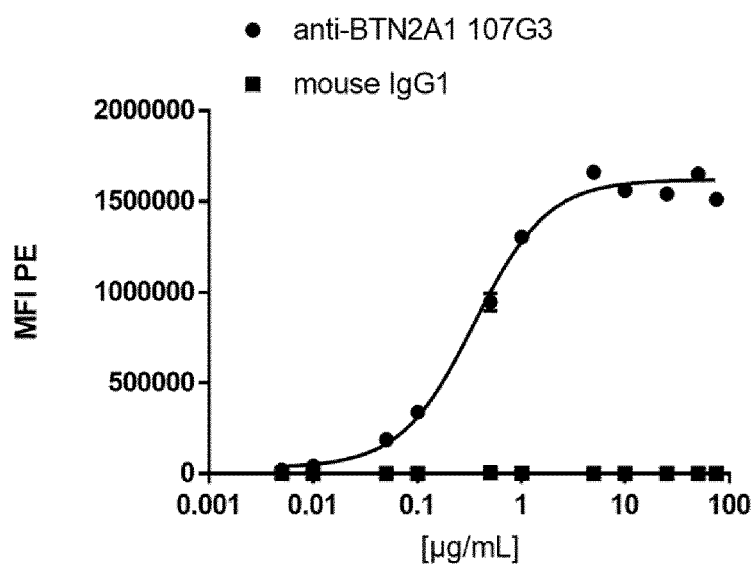

FIG. 3. Anti-BTN2A1 107G3 mAb recognizes BTN2A1 but not BTN3. HEK-293T BTN2 KO cells were transiently transfected with a plasmid encoding BTN2A1-CFP fusion protein. A. Histograms show overlays of the indicated cells and cell transfectants stained with purified anti-BTN2A1 107G3 mAb (top, black line), anti-BTN3 103.2 mAb (bottom, black line), or mIgG1 or IgG2a (dashed lines) controls. For transfected cells, stainings are shown after gating on CFP+ cells. B. Graph shows dose-response curves for purified anti-BTN2A1 107G3 mAb binding on HEK-293T BTN2 KO cells transfected with plasmids encoding BTN2A1-CFP. All stainings were analyzed after gating on CFP+ cells.

Figure 4:
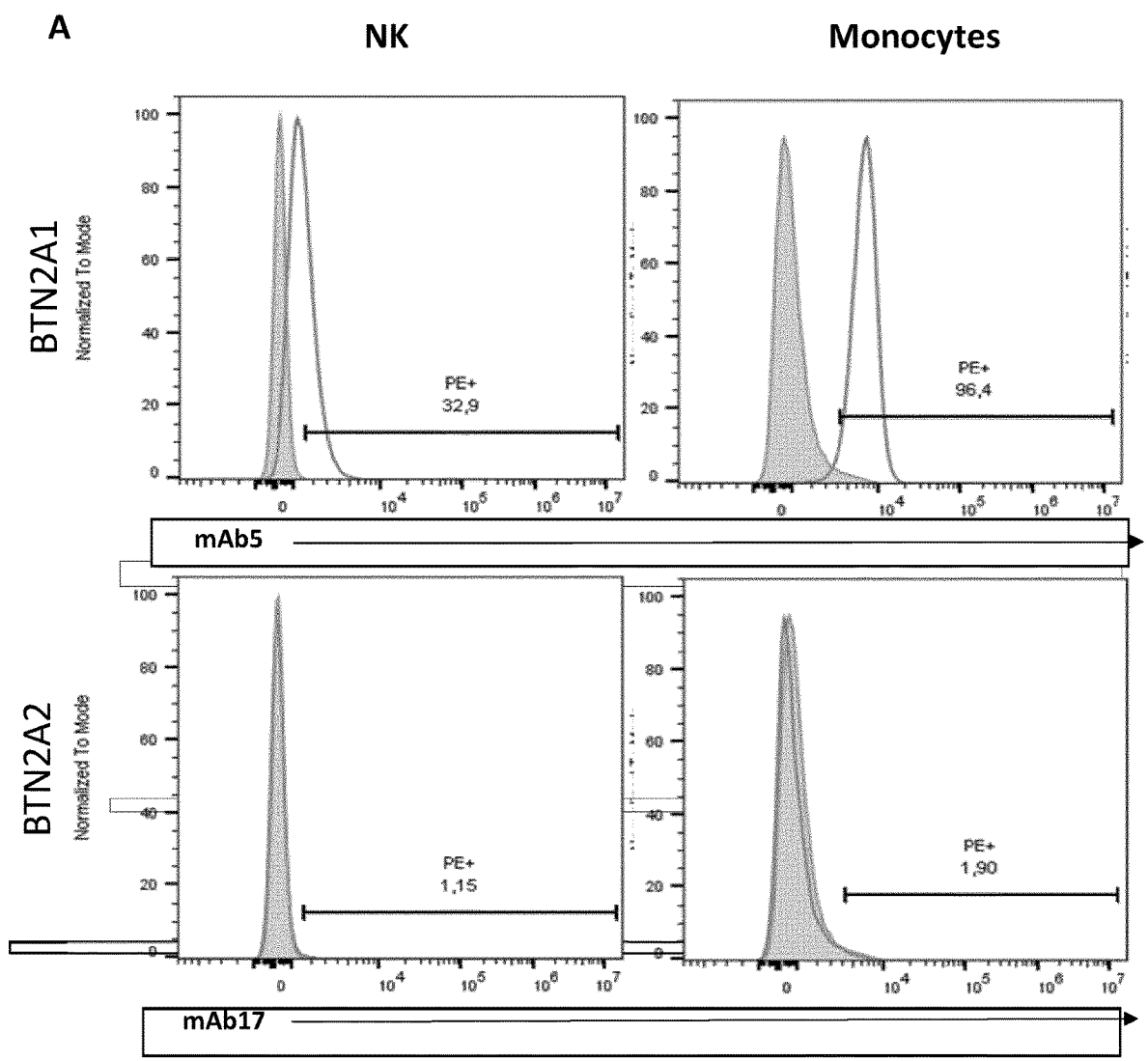

FIG. 4: NK cells and monocytes BTN2A expression and impact on monocyte to M2 macrophage polarization of the reference anti-BTN2A 101G5 and 107G3 mAbs. (A) Representative histograms for BTN2A1 and BTN2A2 expression (in white) versus control isotype (in gray) on NK cell and monocytes from unstimulated HD-PBMCs assessed by flow cytometry. (B) Representative CD14/CD163 dot plots profile of in vitro M1/M2 macrophages or macrophages 101G5 and 107G3 mAbs induced in presence of M-CSF. After 5 days of differentiation, CD14 and CD163 dot plots are generated by flow cytometry analysis.

Figure 5:
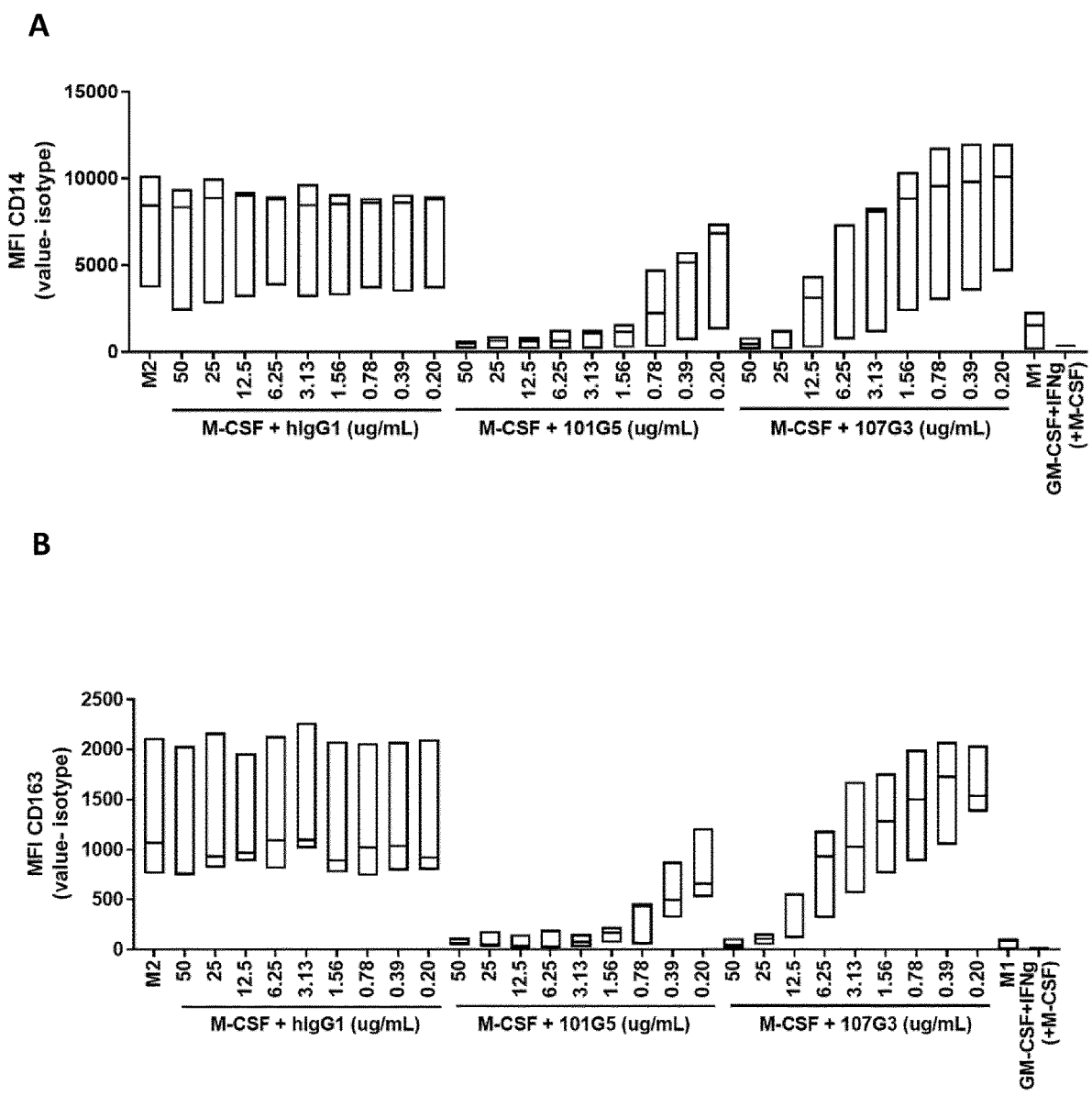
Figure 5:
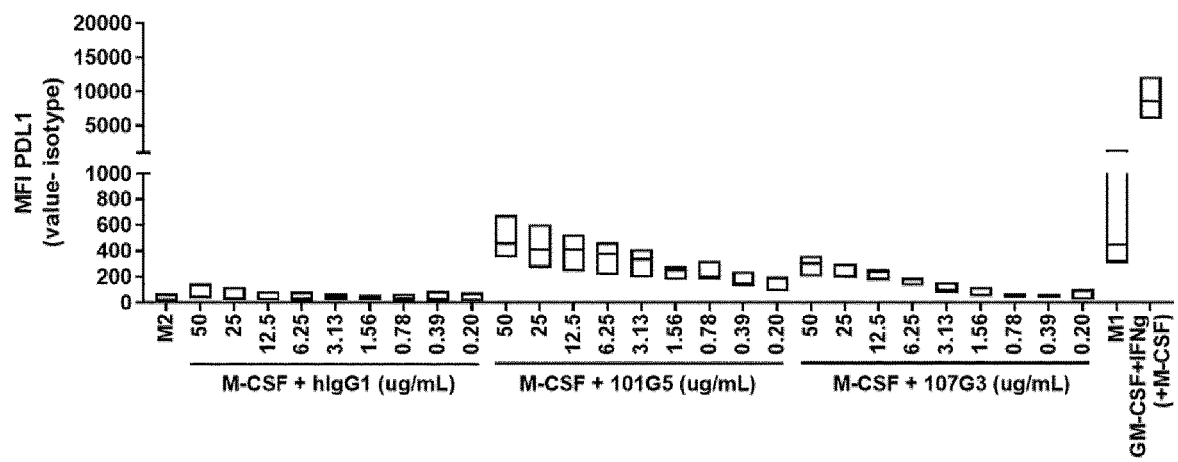
Figure 5:
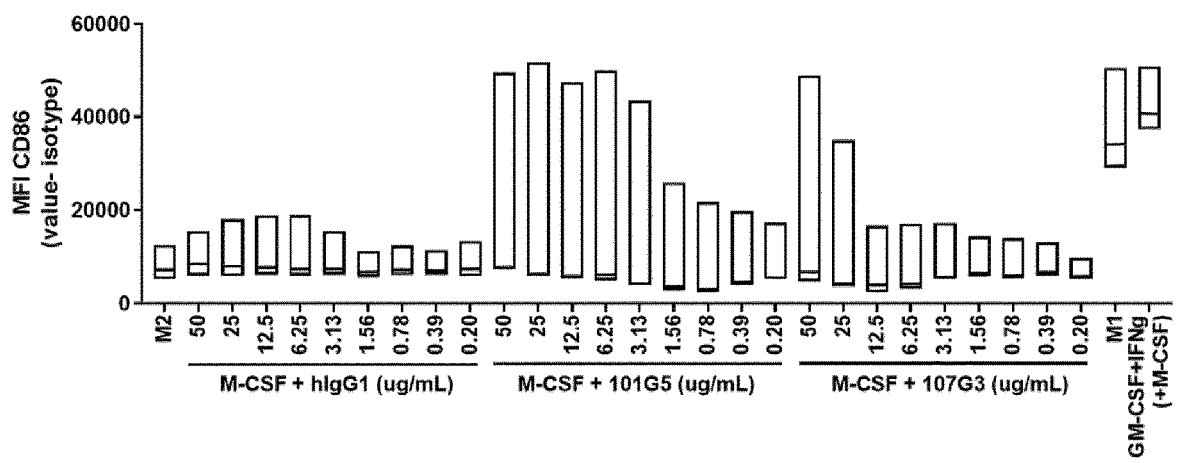
Figure 5:
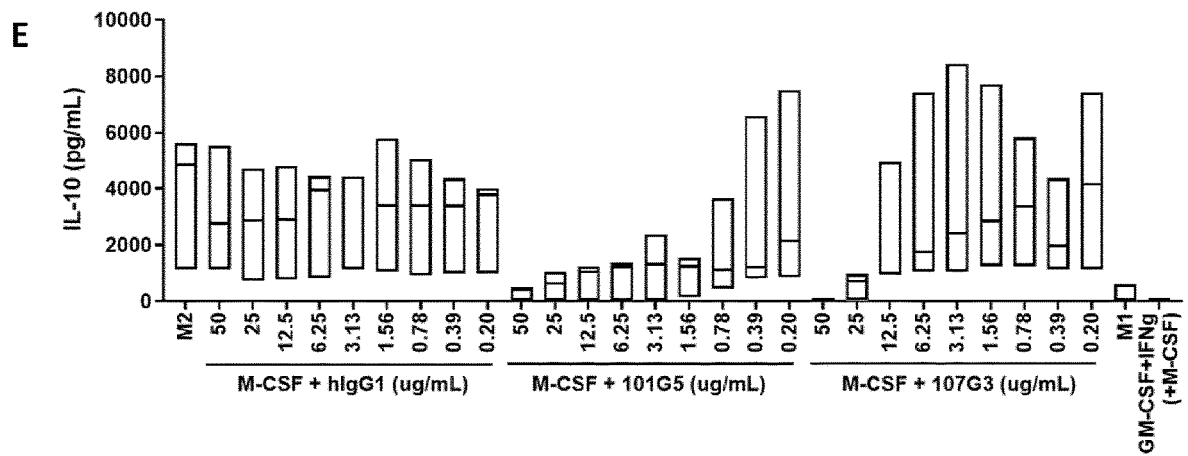
Figure 5:
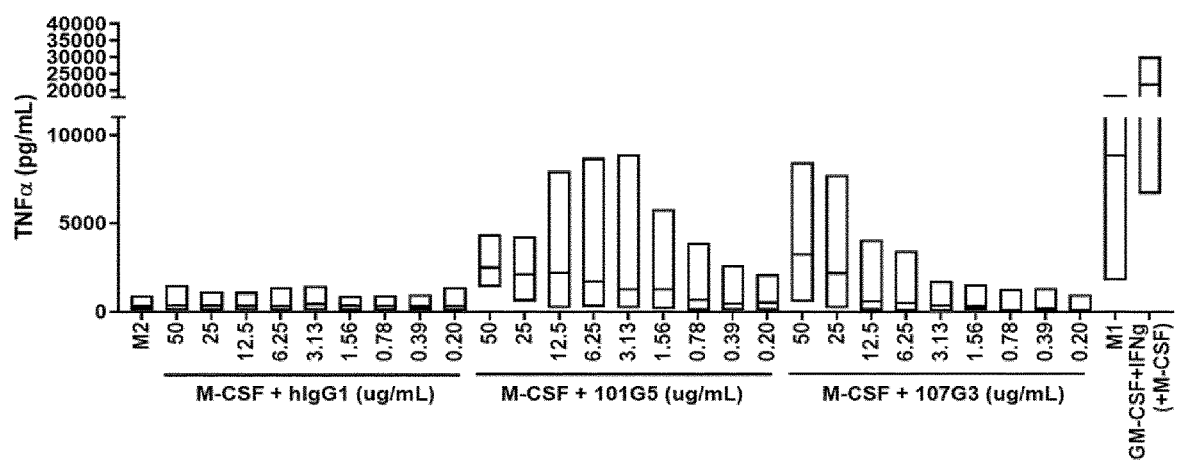

FIG. 5: The reference anti-BTN2A 101G5 and 107G3 mAbs inhibit M2 macrophage polarization in a dose-dependent manner. M1, M2, M2 reverted with GM-CSF and IFNγ, and M-CSF-induced macrophages in presence of different concentrations 101G5 or 107G3 mAbs (or their isotype control), were polarized for 5 days, and stimulated or not with LPS for 2 additional days. The expression of CD14 (A), CD163 (B), PDL1 (C) and CD86 (D), was analyzed by flow cytometry on unstimulated cells (A-C) or LPS stimulated cells (D). Results are expressed in Median Fluorescence Intensity values (MFI) subtracted by their corresponding isotype controls. IL-10 (E) and TNFα (F) were quantified in LPS stimulated macrophage supernatants by ELISA. Results are expressed in μg/mL.

Figure 6:
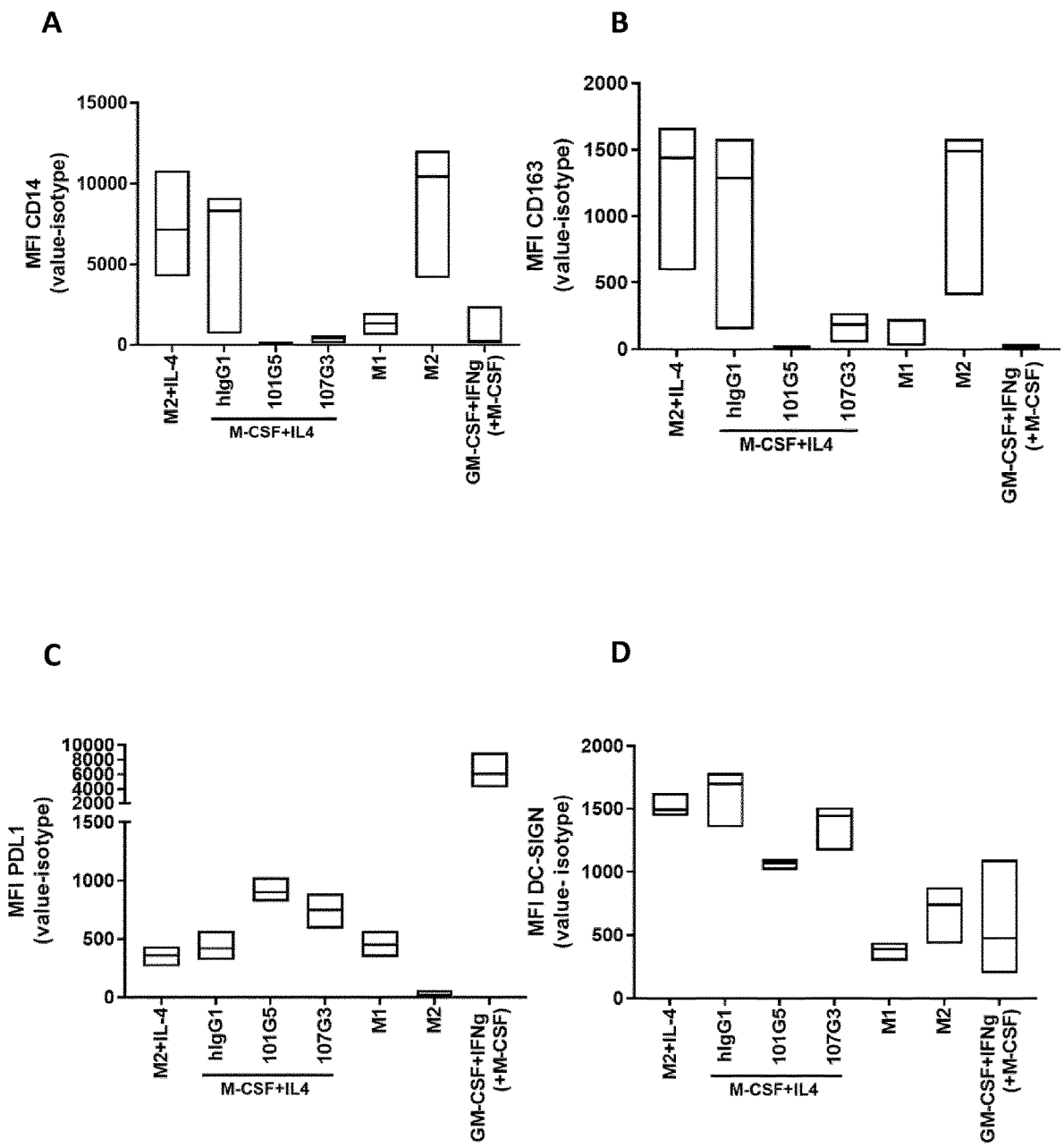
Figure 6:
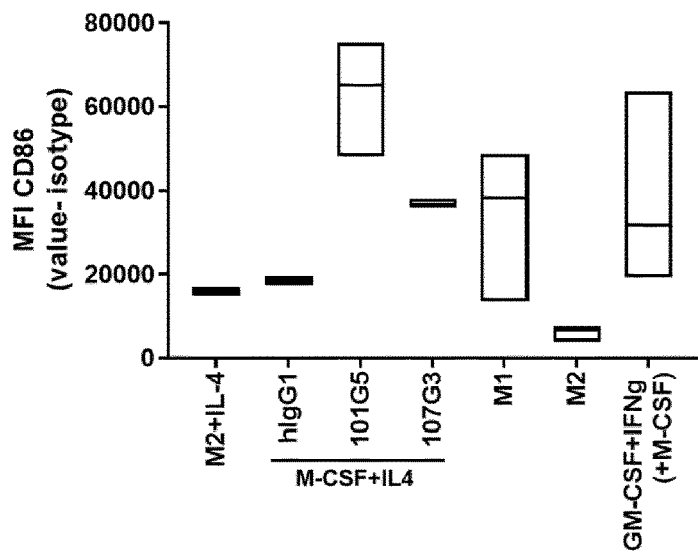
Figure 6:
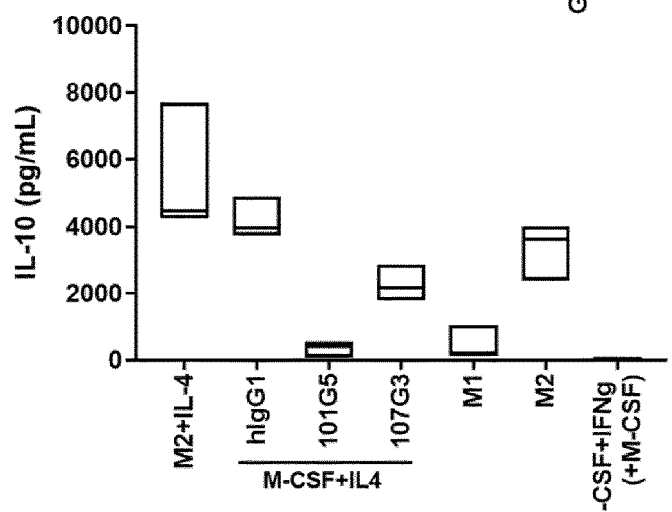
Figure 6:
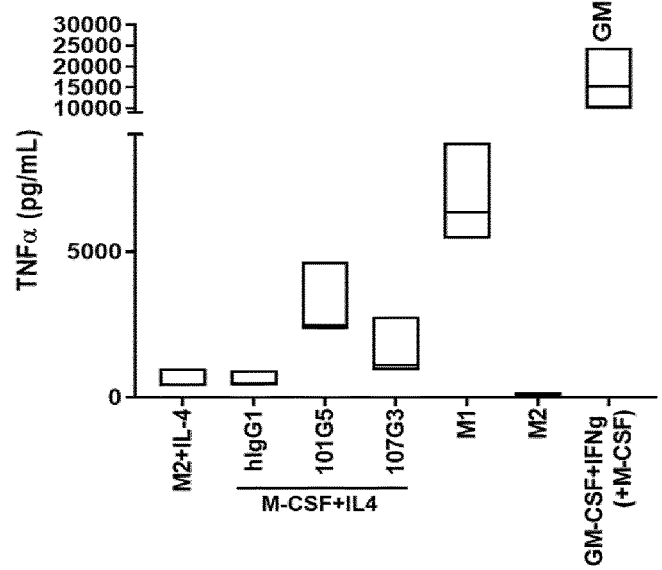

FIG. 6: The reference anti-BTN2A 101G5 and 107G3 mAbs inhibit "M2+IL-4"-induced polarization from monocytes. M1, M2, "M2+IL4", M2 reverted with GM-CSF and IFNγ, and macrophages induced with M-CSF+IL-4 and 101G5 or 107G3 mAbs (or their isotype control) at 10 µg/mL were generated for 5 days, and stimulated or not with LPS for 2 additional days. The expression of CD14 (A), CD163 (B), PDL1 (C), DC-SIGN (D) and CD86 (E), was analyzed by flow cytometry on non-stimulated cells (A-D) or LPS stimulated cells (E). Results are expressed in Median Fluorescence Intensity values (MFI) subtracted by their corresponding isotype controls. IL-10 (F) and TNFα (G) were quantified in LPS-stimulated macrophage supernatants by ELISA. Results are expressed in µg/mL.

Figure 7:
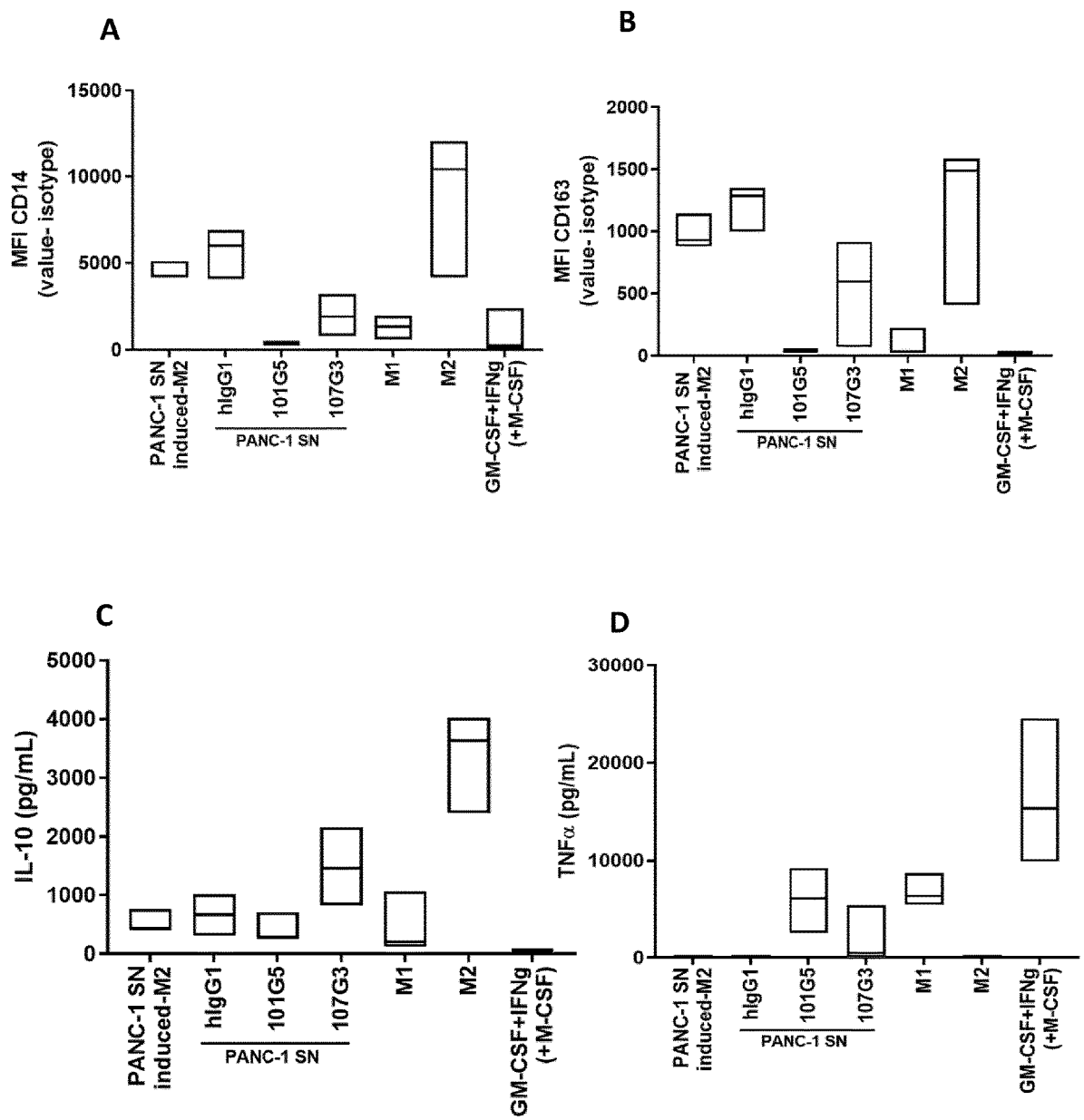

FIG. 7: The reference anti-BTN2A 101G5 and 107G3 mAbs inhibit cancer cell-induced M2 polarization. M1, M2, PANC-1 conditioned medium-induced M2, M2 reverted with GM-CSF and IFNγ, and macrophages induced with PANC-1 conditioned medium and 101G5 or 107G3 mAbs (or their isotype control) at 10 µg/mL were generated for 5, and stimulated or not with LPS for 2 additional days. The expression of CD14 (A), CD163 (B), was analyzed by flow cytometry on non-stimulated cells. Results are expressed in Median Fluorescence Intensity values (MFI) subtracted by their corresponding isotype controls. IL-10 (C) and TNFα (D) were quantified in LPS-stimulated macrophage supernatants by ELISA. Results are expressed in µg/mL.

Figure 8:
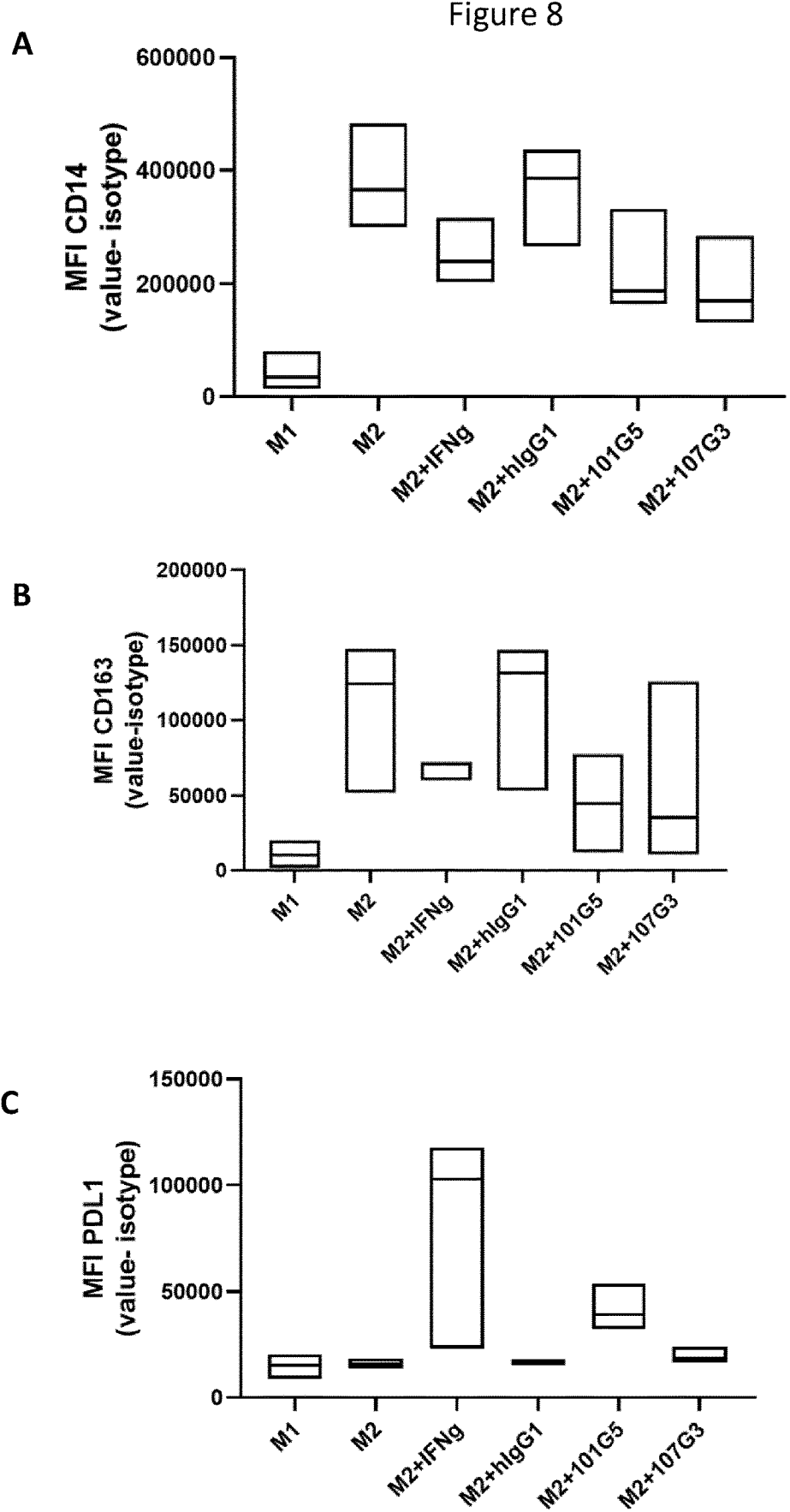
Figure 8:
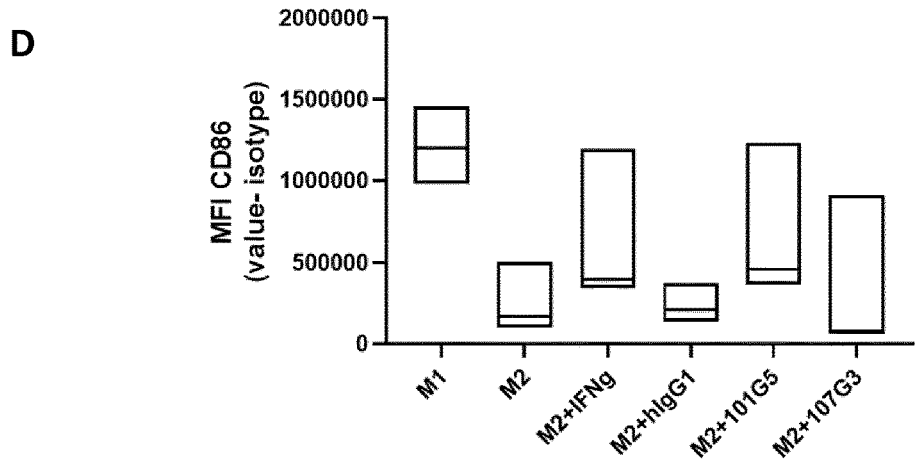
Figure 8:
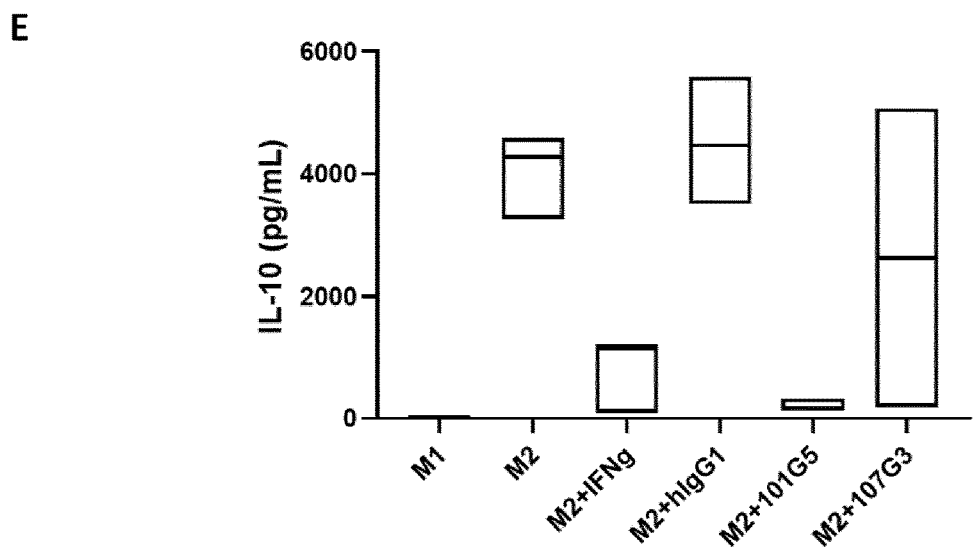
Figure 8:
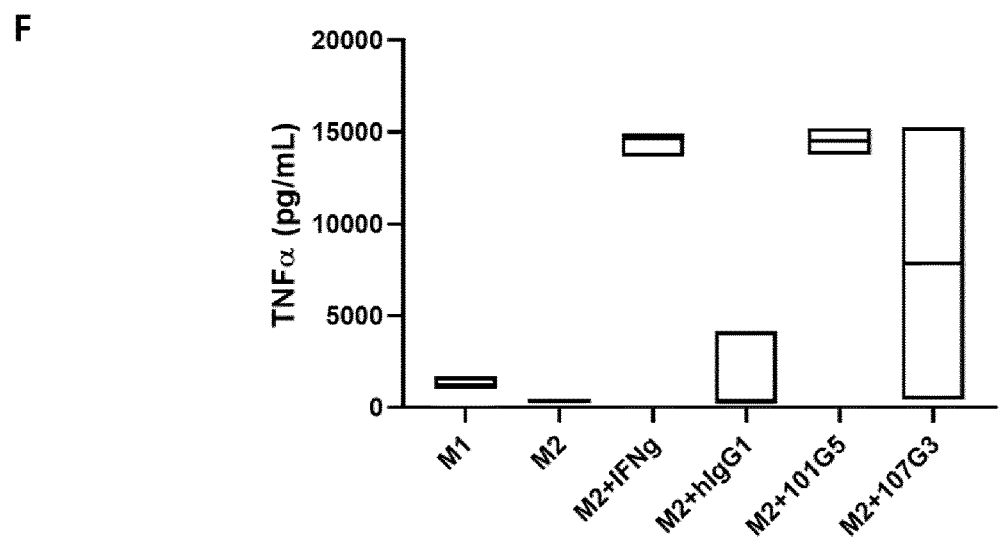
Figure 8:
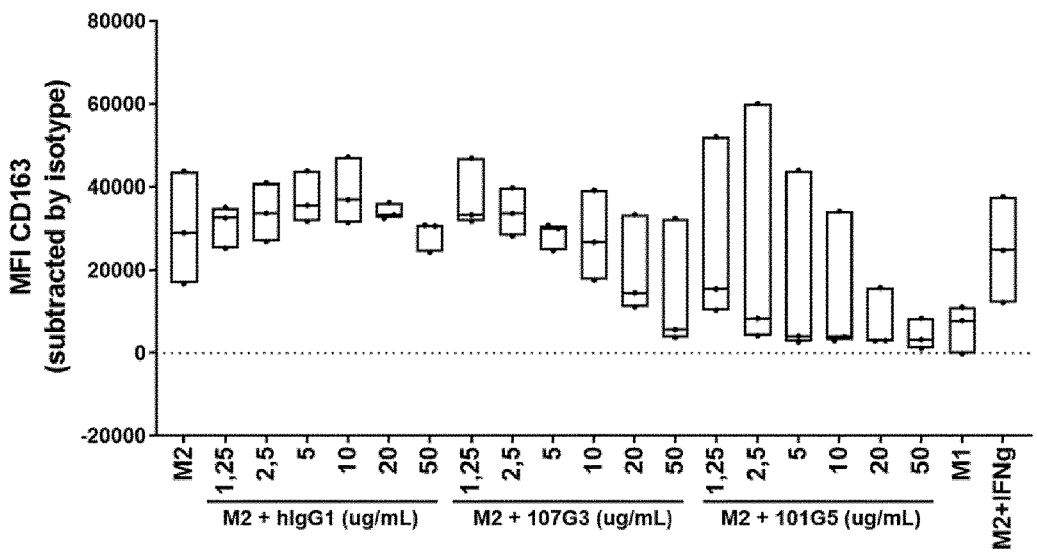
Figure 8:
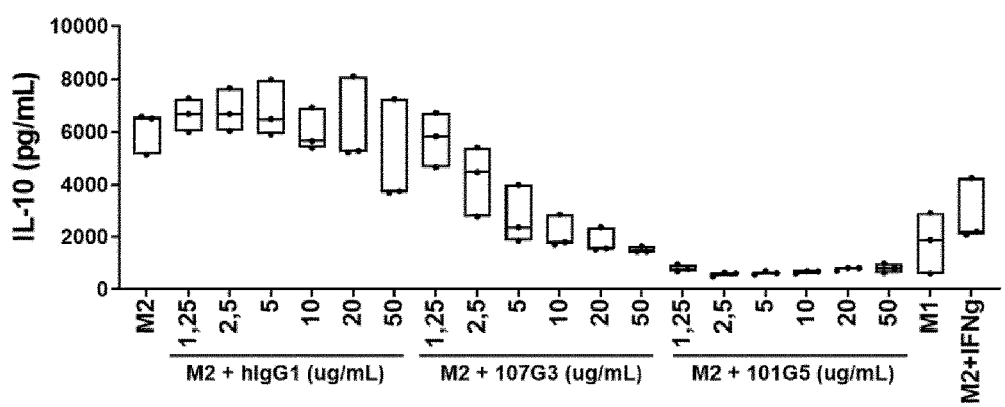
Figure 8:
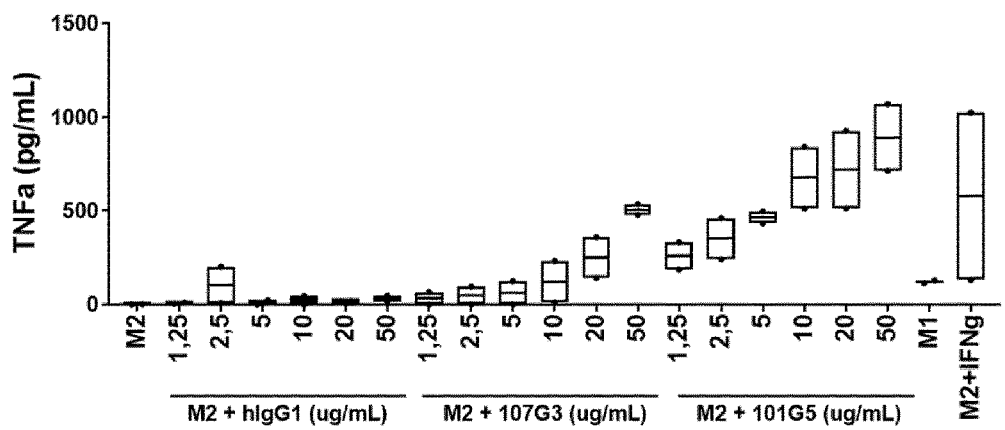

FIG. 8: The reference anti-BTN2A 101G5 and 107G3 mAbs revert M2 macrophages towards pro-inflammatory M1 macrophages: phenotype and cytokine secretion. M1, M2 were generated from monocytes for 5 days. After 5 days, 101G5 or 107G3 mAbs (or the isotype control) at 10 µg/mL or IFNγ were added on M2 macrophages for 2 days, and stimulated or not with LPS for 2 additional days. The expression of CD14 (A), CD163 (B), PDL1 (C) and CD86 (D), was analyzed by flow cytometry on non-stimulated cells (A-C) or LPS stimulated cells (D). Results are expressed in Median Fluorescence Intensity values (MFI) subtracted by their corresponding isotype controls. IL-10 (E) and TNFα (F) were quantified in LPS-stimulated macrophage supernatants by ELISA. Results are expressed in µg/mL.

Figure 9:
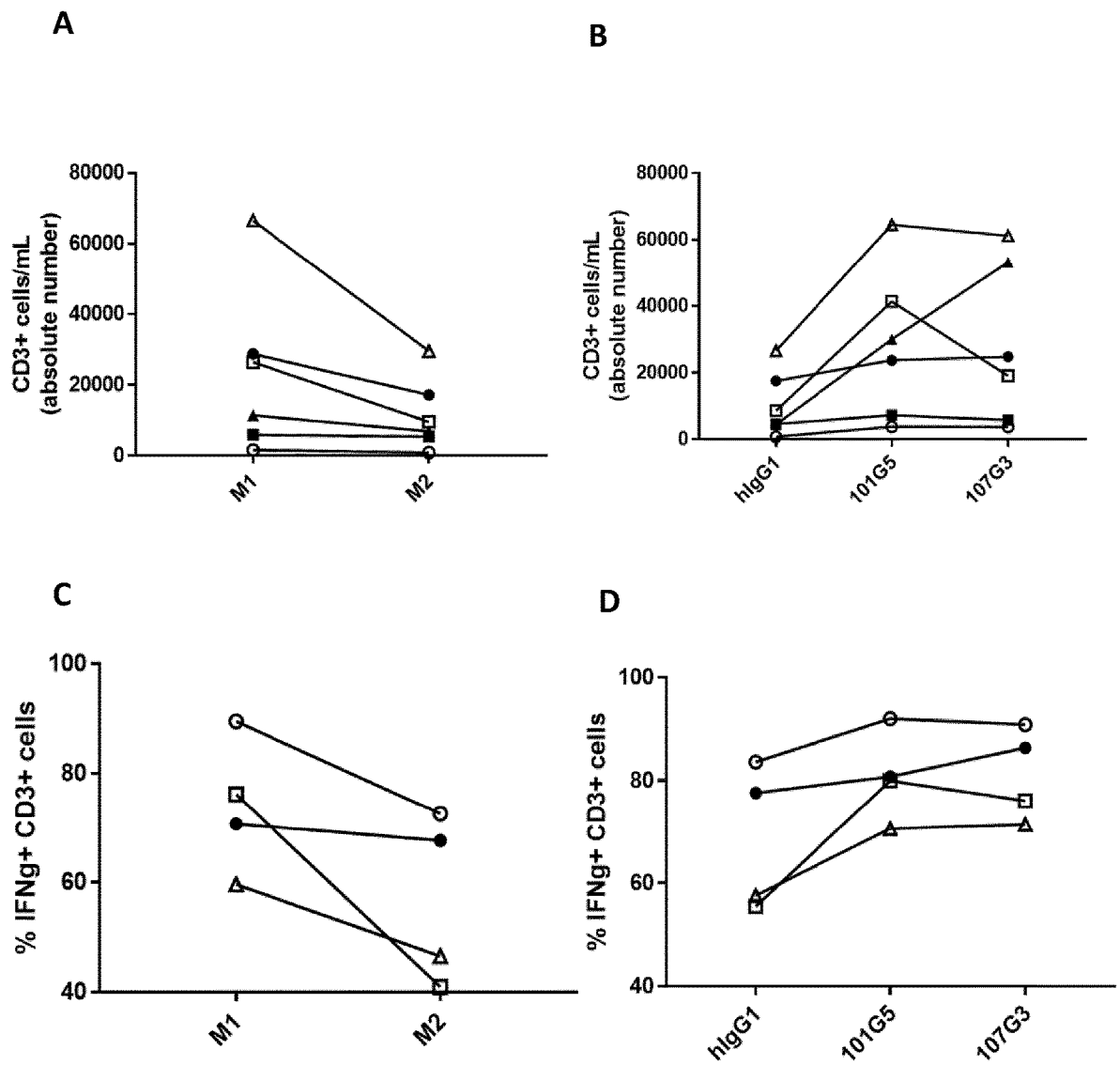
Figure 9:
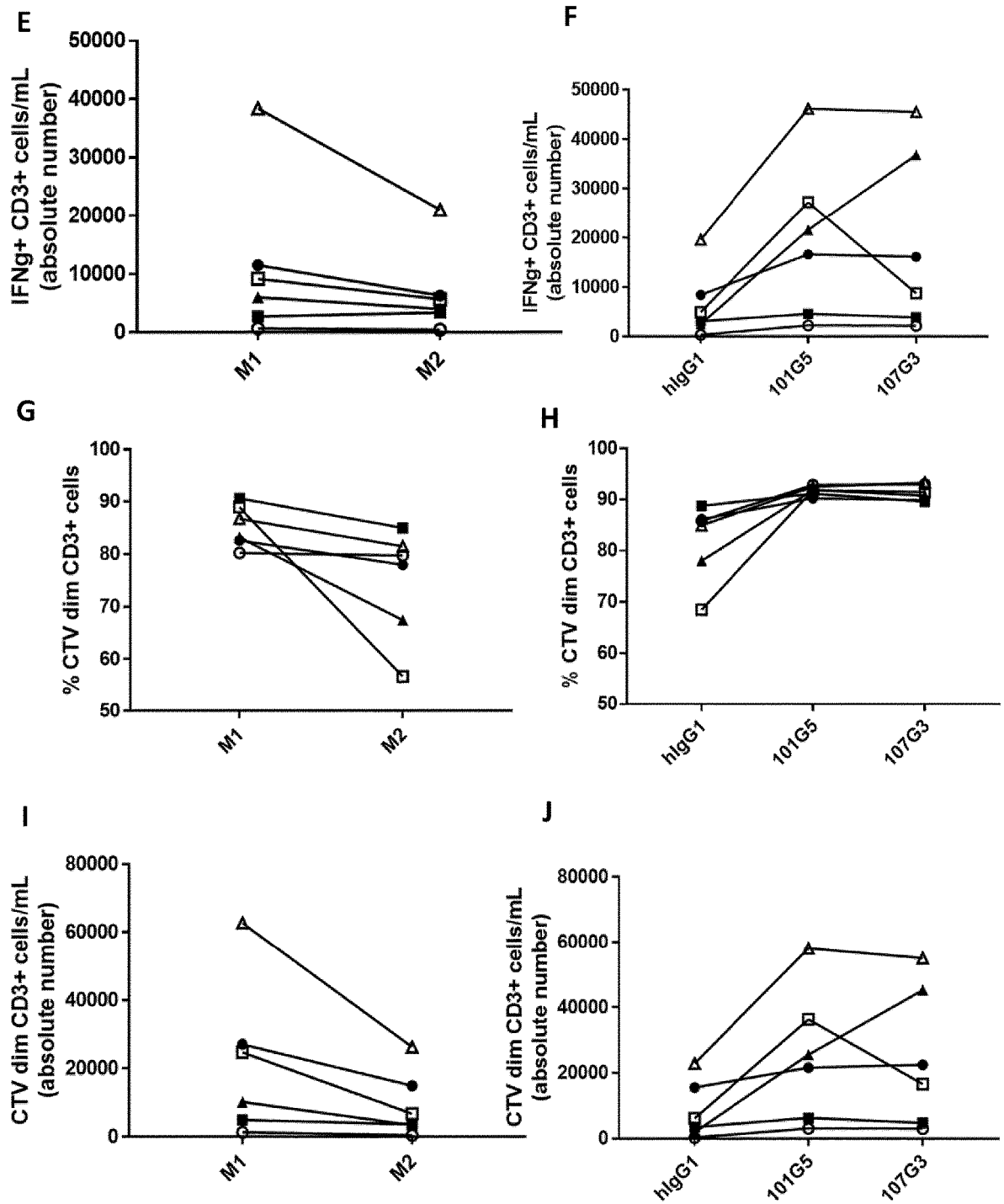

FIG. 9: The reference anti-BTN2A 101G5 and 107G3 mAbs release M2-mediated inhibition of T cell proliferation and IFNγ secretion. Differentiated M1, M2 or macrophages induced in presence of 101G5 and 107G3 mAbs (or their isotype control)-were co-cultured with allogeneic OKT3-activated CTV-labelled CD3+ T cells for 5 days. Following co-culture, cells are stimulated with PMA/ionomycine and GolgiStop protein inhibitor for 5 hours and the number of CD3+ T cells (A and B), the intracellular IFNγ production (C-F) and the proliferation (CellTrace Violet, CTV dim) (G-J) were quantified by flow cytometry. The proliferation was quantified by dilution of the CTV dye (CTV signal at day 0 as baseline). Results are in absolute numbers of CD3+ T cells, calibrated on CountBright absolute counting beads (B, E, F, I and J) or in percentage of CD3+ T cells (C, D, G and H).

Figure 10:
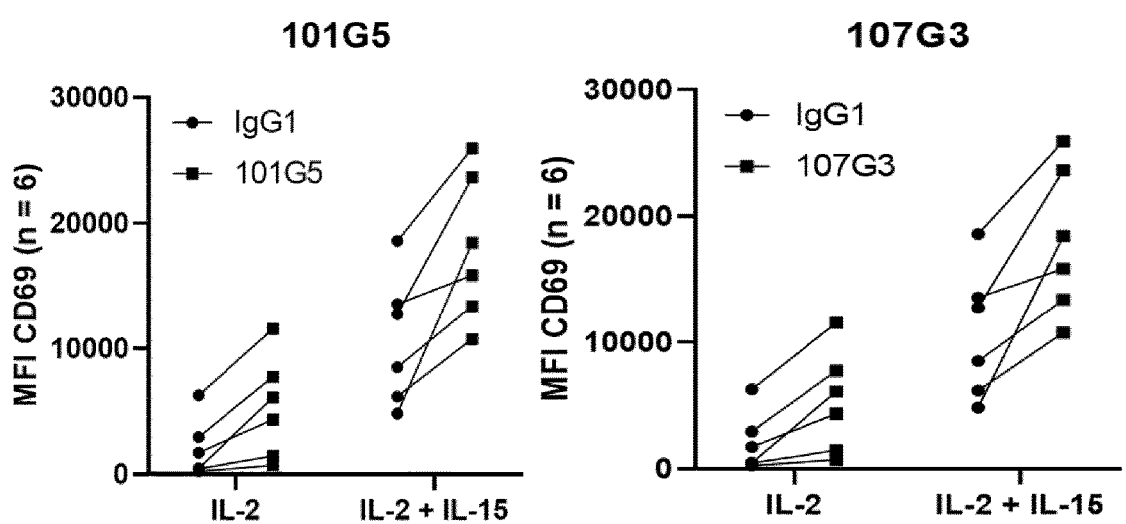
Figure 10:
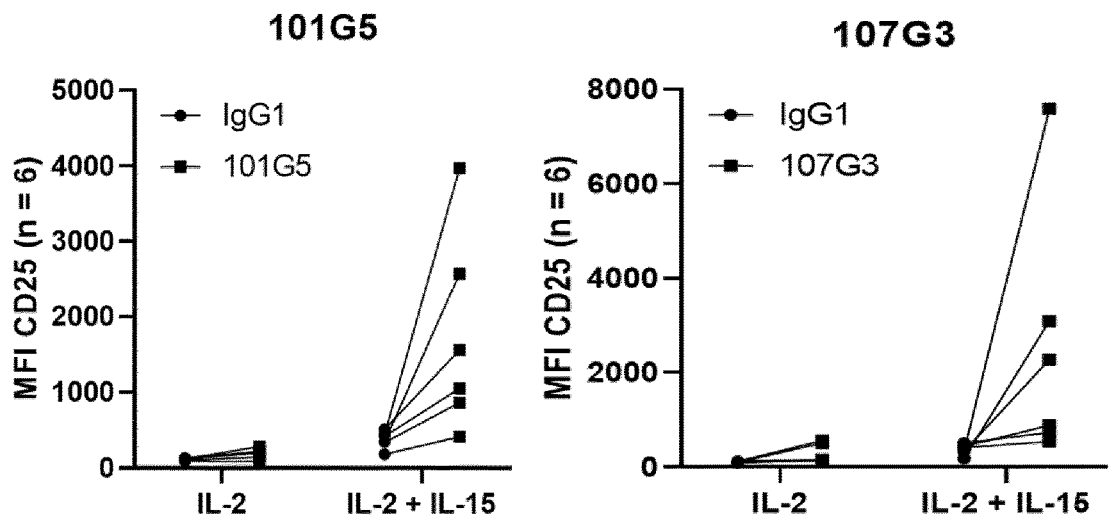
Figure 10:
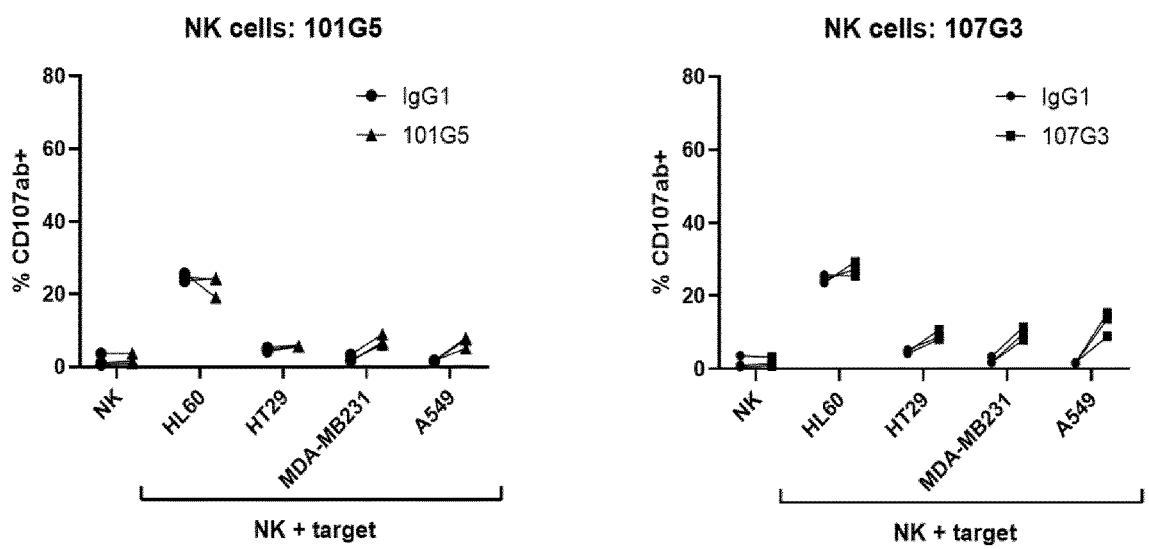
Figure 10:
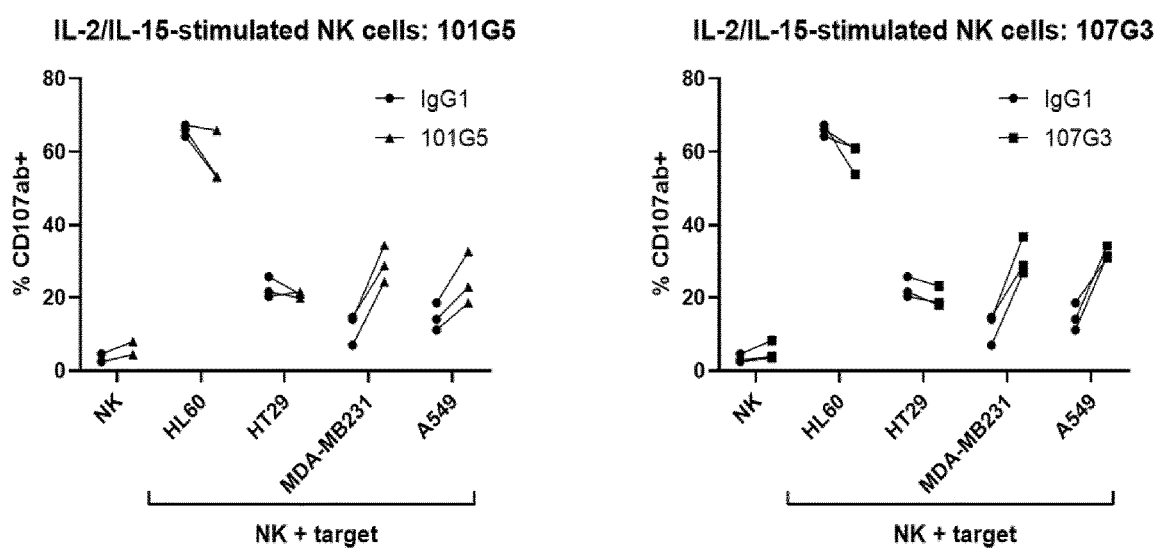
Figure 10:
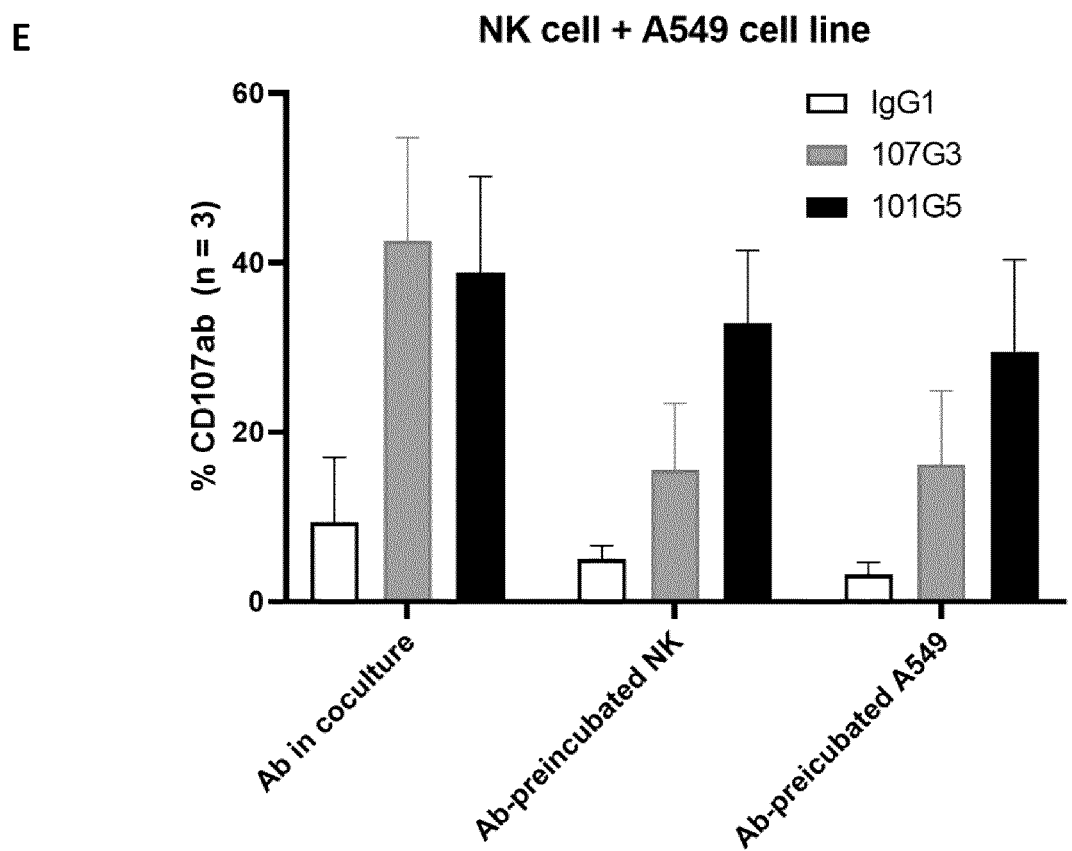

FIG. 10: Effect of the reference anti-BTN2A 101G5 and 107G3 mAbs on activation and cytotoxicity of purified NK cells. (A-B) Purified NK cells were cultured with the reference anti-BTN2A 101G5 and 107G3 mAbs (or the control isotype) for 5 days with IL-2 or IL-2/IL-15 stimulation. NK cell activation was evaluated by accessing the CD69 (A) and CD25 (B) expression (MFI) within non-stimulated and IL-2/IL-15-stimulated NK cell in presence of the indicated mAb or control isotype. (C-D) Purified NK cells were pre-incubated overnight with the reference anti-BTN2A 101G5 and 107G3 mAbs (or the control isotype) in presence or not of IL-2/IL-15 stimulation and were then cocultured with human tumor cell lines for 4 hours. NK cell degranulation was accessed by flow cytometry as the percentage of CD107αβ within non-stimulated (C) and IL-2/IL-15-stimulated NK cells (D) against each tumor cells line in presence of the indicated mAb or control isotype. (E) NK cell degranulation against A549 cell line when the reference anti-BTN2A 101G5 and 107G3 mAbs (or the control isotype) were previously pre-incubated on NK cells or target cells prior to 4 hours of co-culture, compared to mAbs added to the co-culture without pre-incubation.

Figure 11:
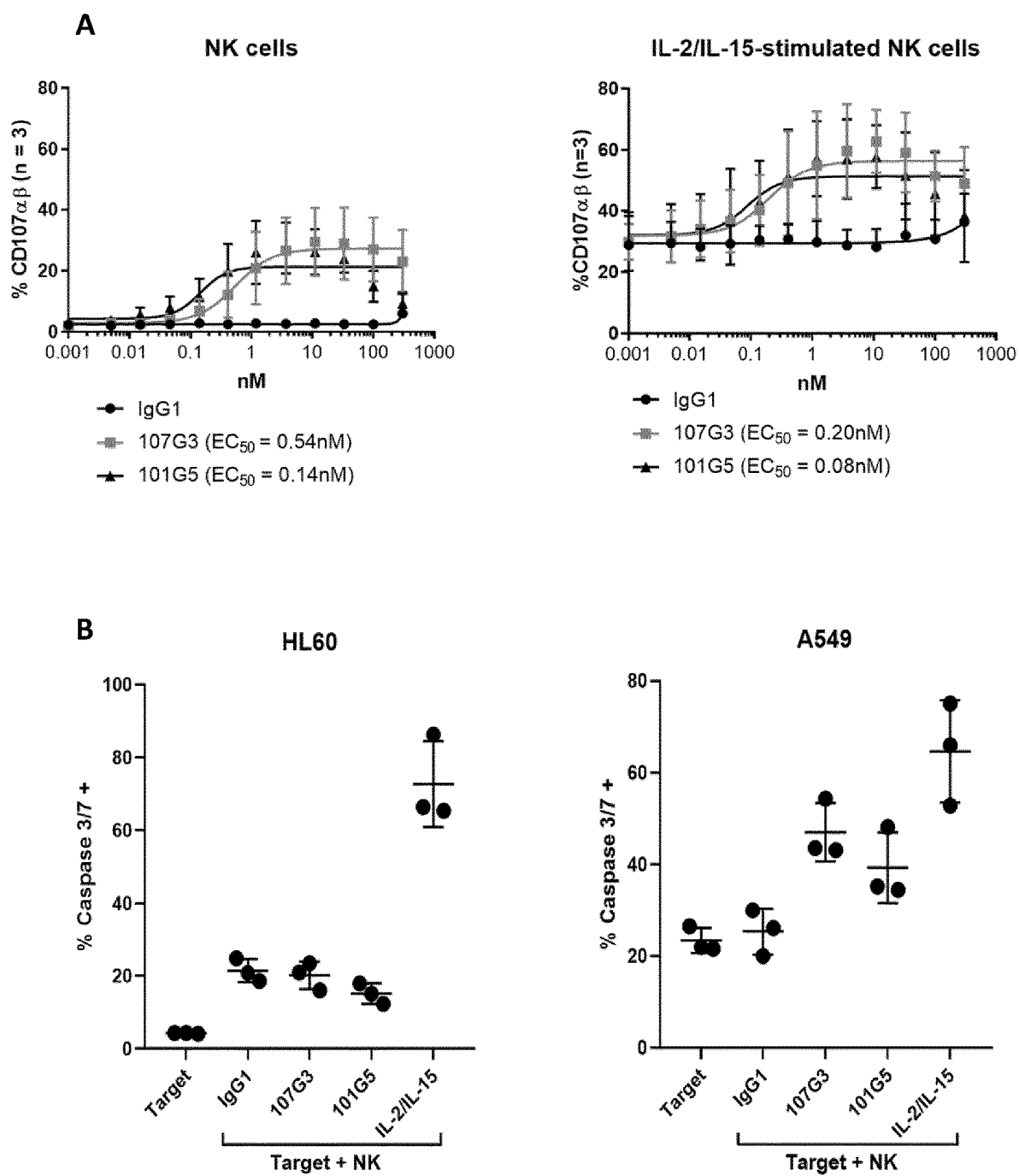

FIG. 11: The reference anti-BTN2A 101G5 and 107G3 mAbs enhance on NK cell degranulation and killing against adenocarcinoma cell lines. (A) Purified NK cells were pre-incubated overnight with the reference anti-BTN2A 101G5 and 107G3 mAbs (or the control isotype) in presence or not of IL-2/IL-15 stimulation and were then cocultured with DU-145 cell line for 4 hours. NK cell degranulation was assessed by flow cytometry as the percentage of CD107αβ+ cells. The $EC_{50}$ of NK cell degranulation enhancement was calculated for the indicated mAb using a four-parameter dose-response curve on Prism software. (B) Purified NK cells were preincubated overnight with the reference anti-BTN2A 101G5 and 107G3 mAbs (or the control isotype or IL-2/IL-15 stimulation) and were then co-cultured with HL-60 and A549 cell line for 4 hours. NK cell-mediated cancer cell death was evaluated by accessing the percentage of caspase 3/7+ cells in presence of the indicated mAb or control isotype.

Figure 12:
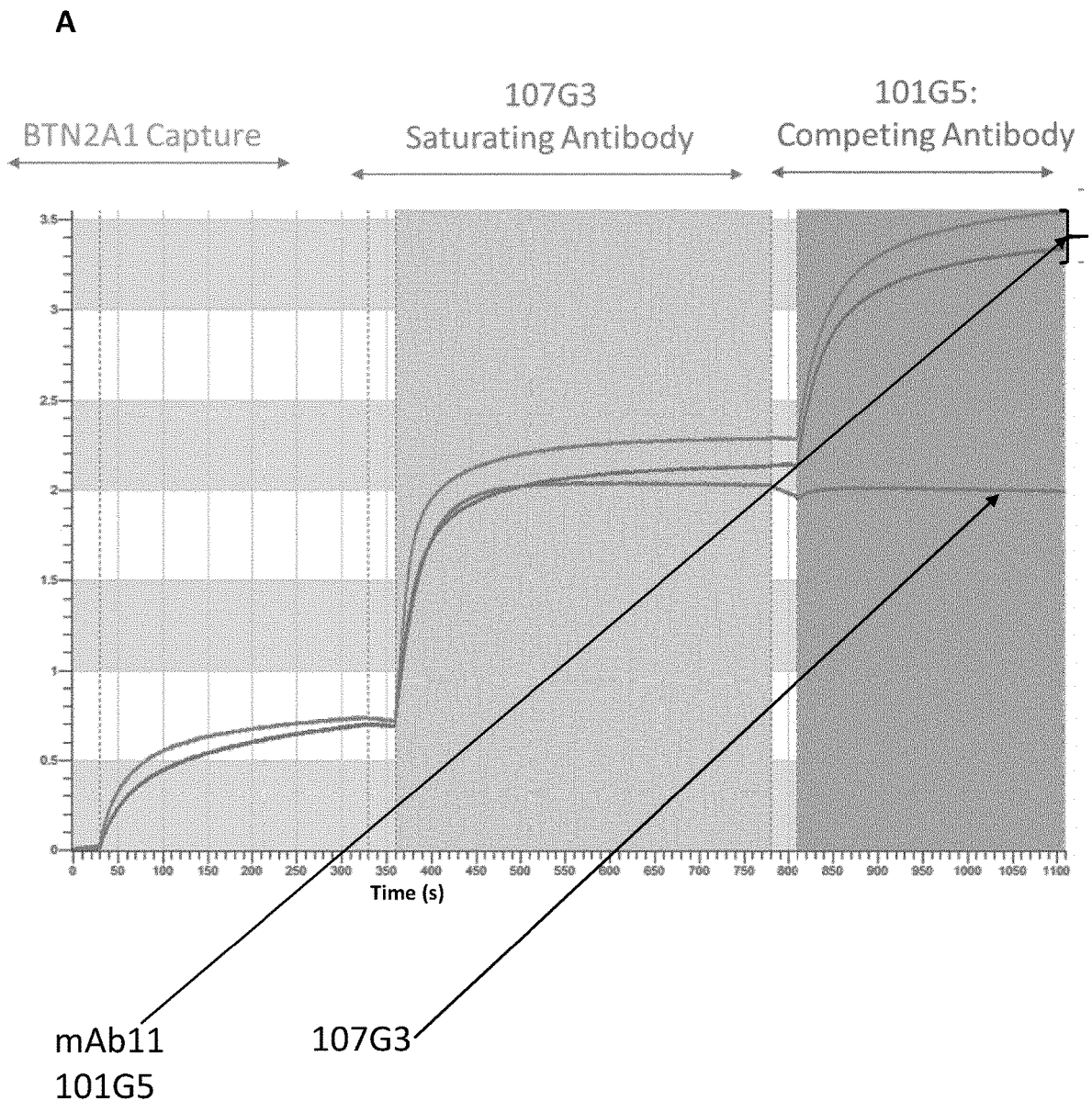
Figure 12:
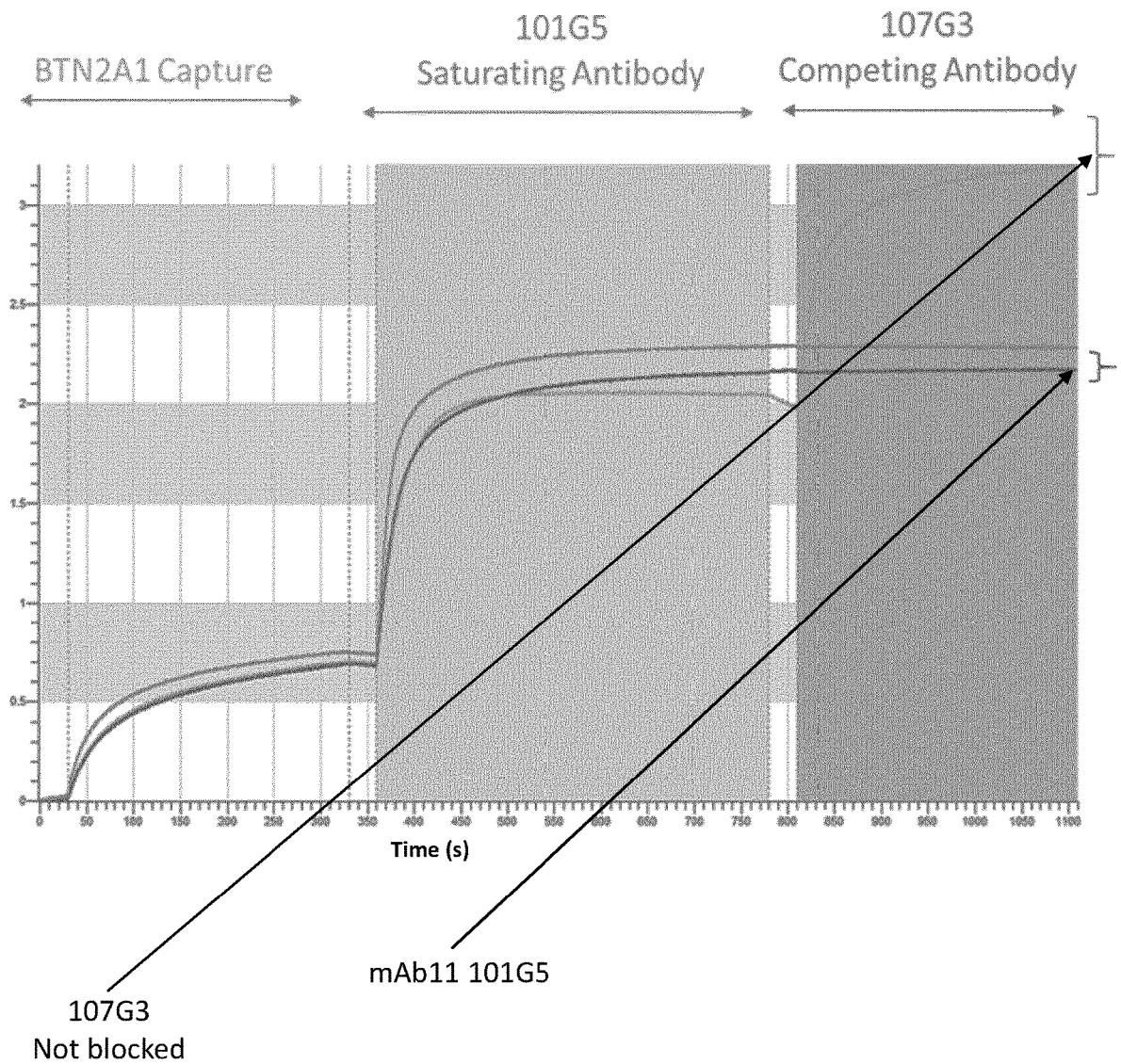

FIG. 12: Binning experiments of the reference anti-BTN2A1 101G5 and 107G3 mAbs against BTN2A1. Binning experiments were performed on an Octet Red96 platform, system based on Bio-layer interferometry (BLI) technology. 107G3 and 101G5 were tested in a pairwise combinatorial manner against rhBTN2A1-His protein. A. 107G3 is saturating and 101G5 is competitor; B: 101G5 is saturating and 107G3 is competitor; C: measurements in arbitrary units binding and self-blocking pairs of mAbs.

Figure 13:
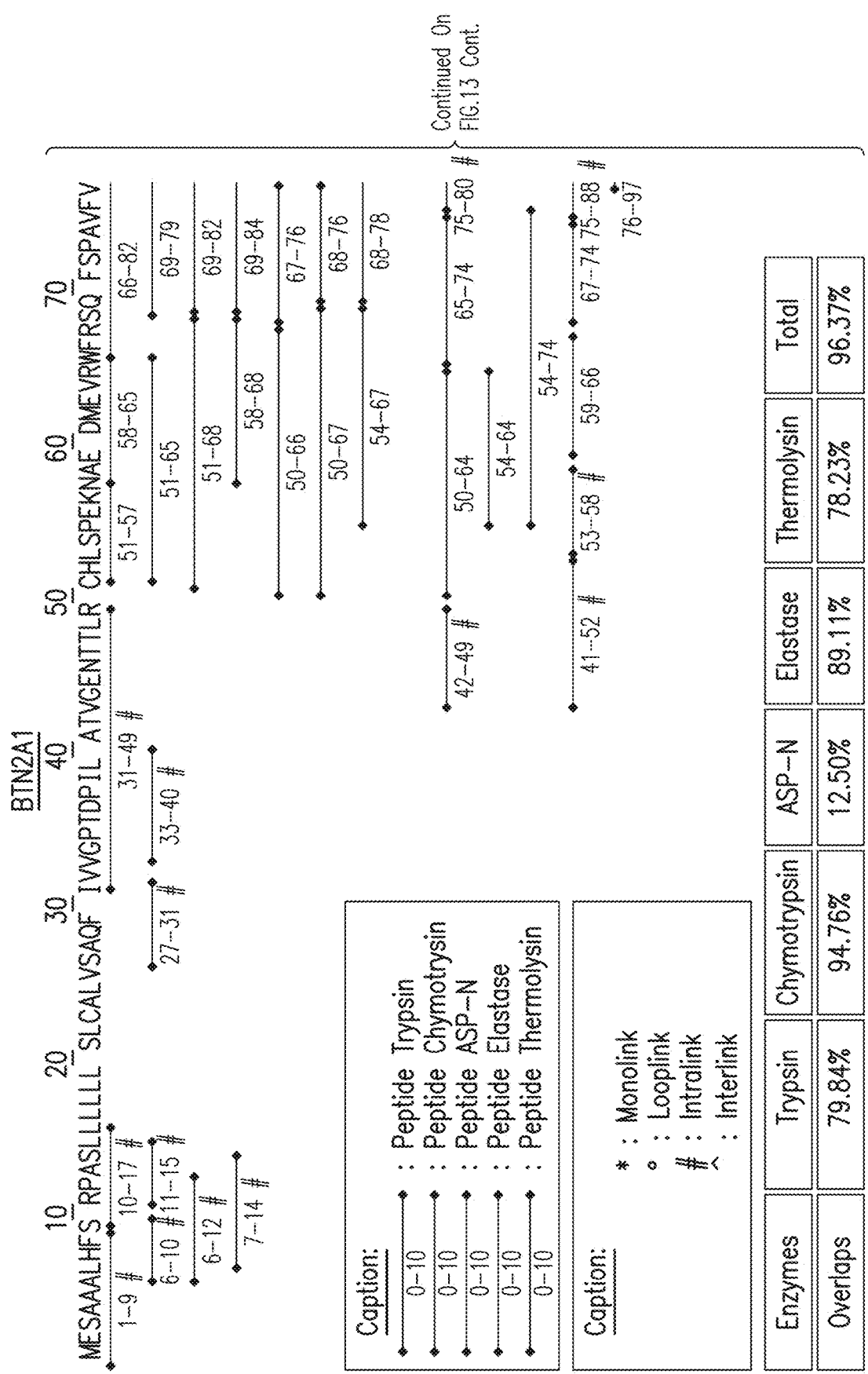
Figure 13:
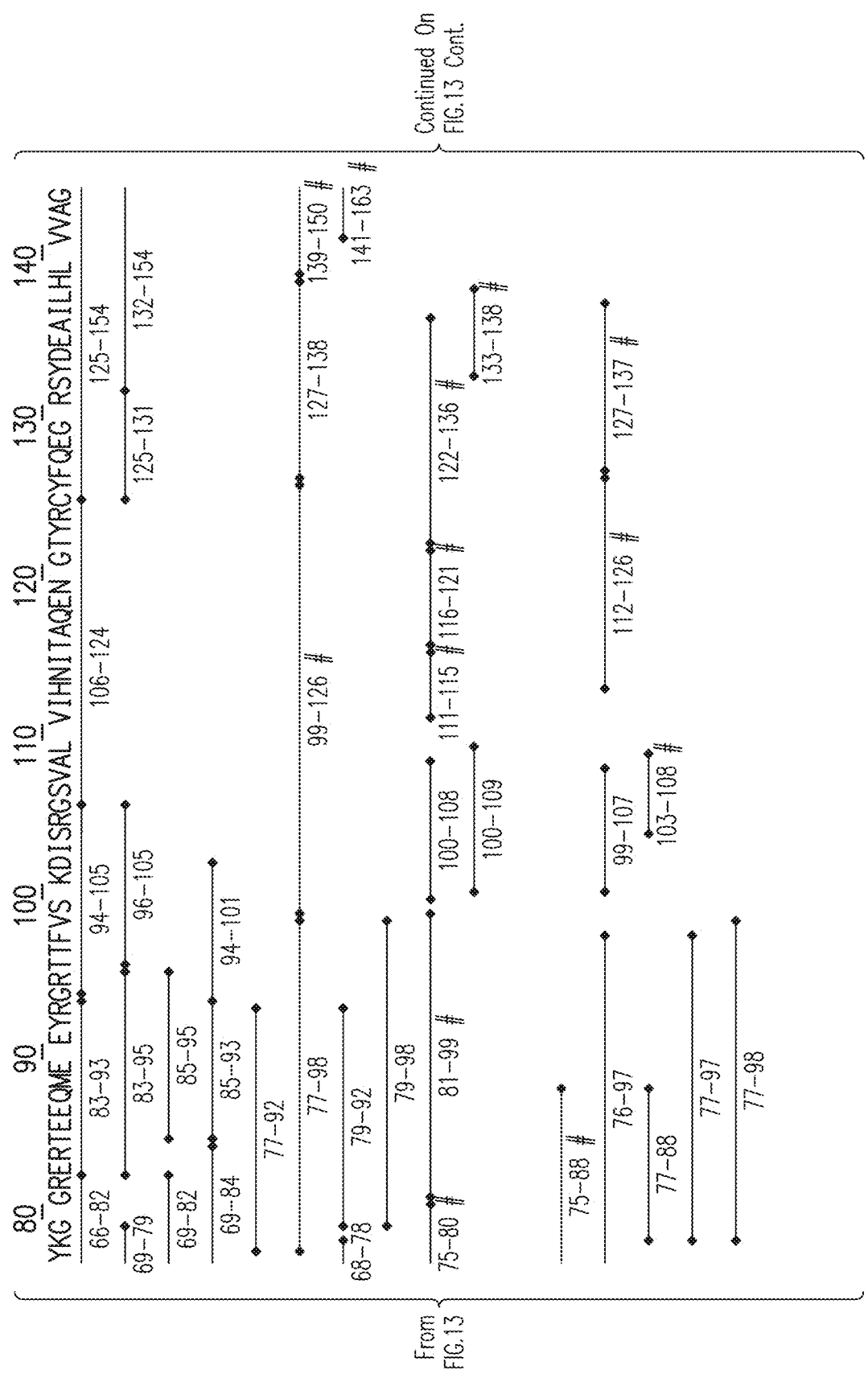
Figure 13:
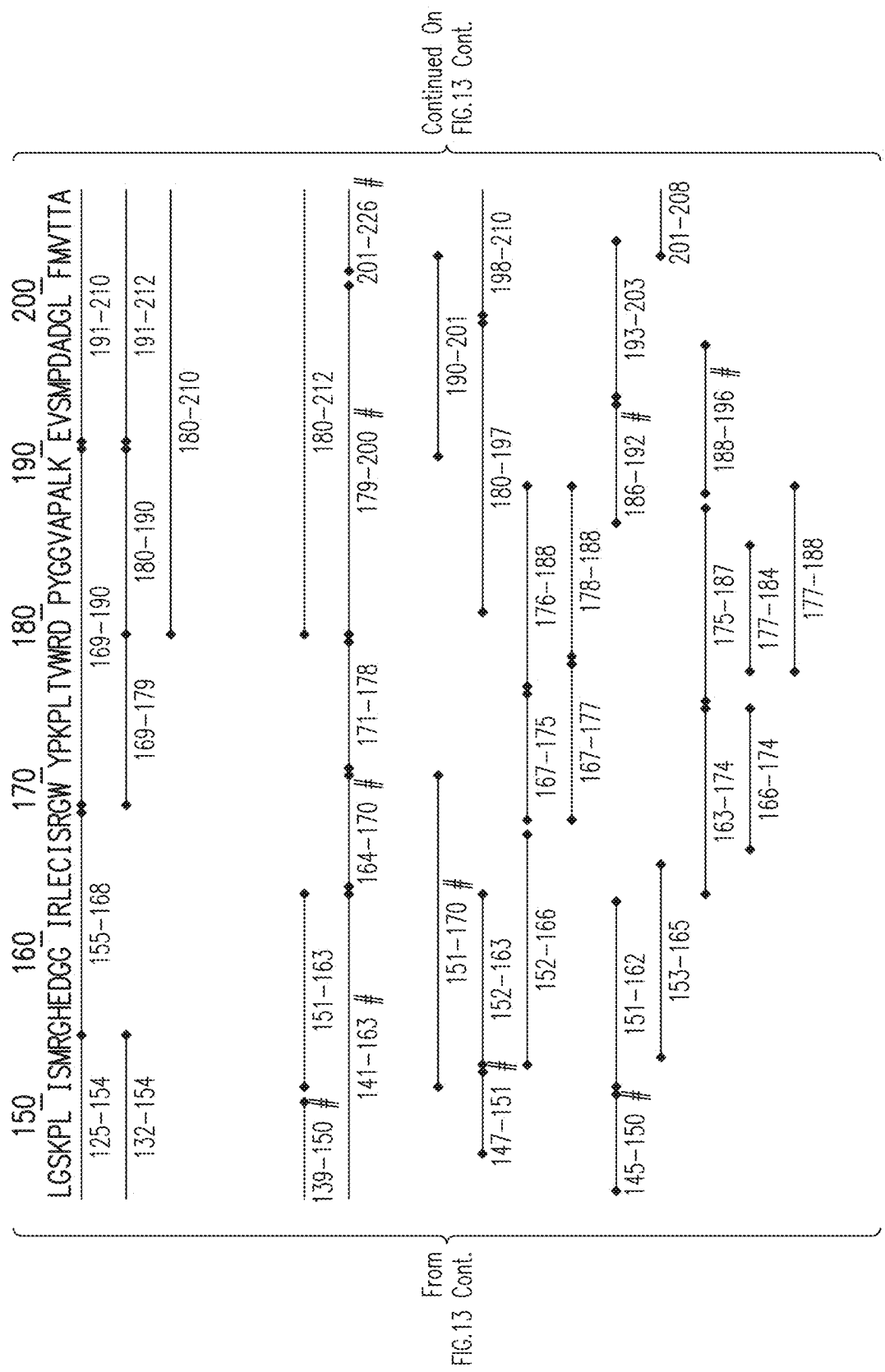
Figure 13:
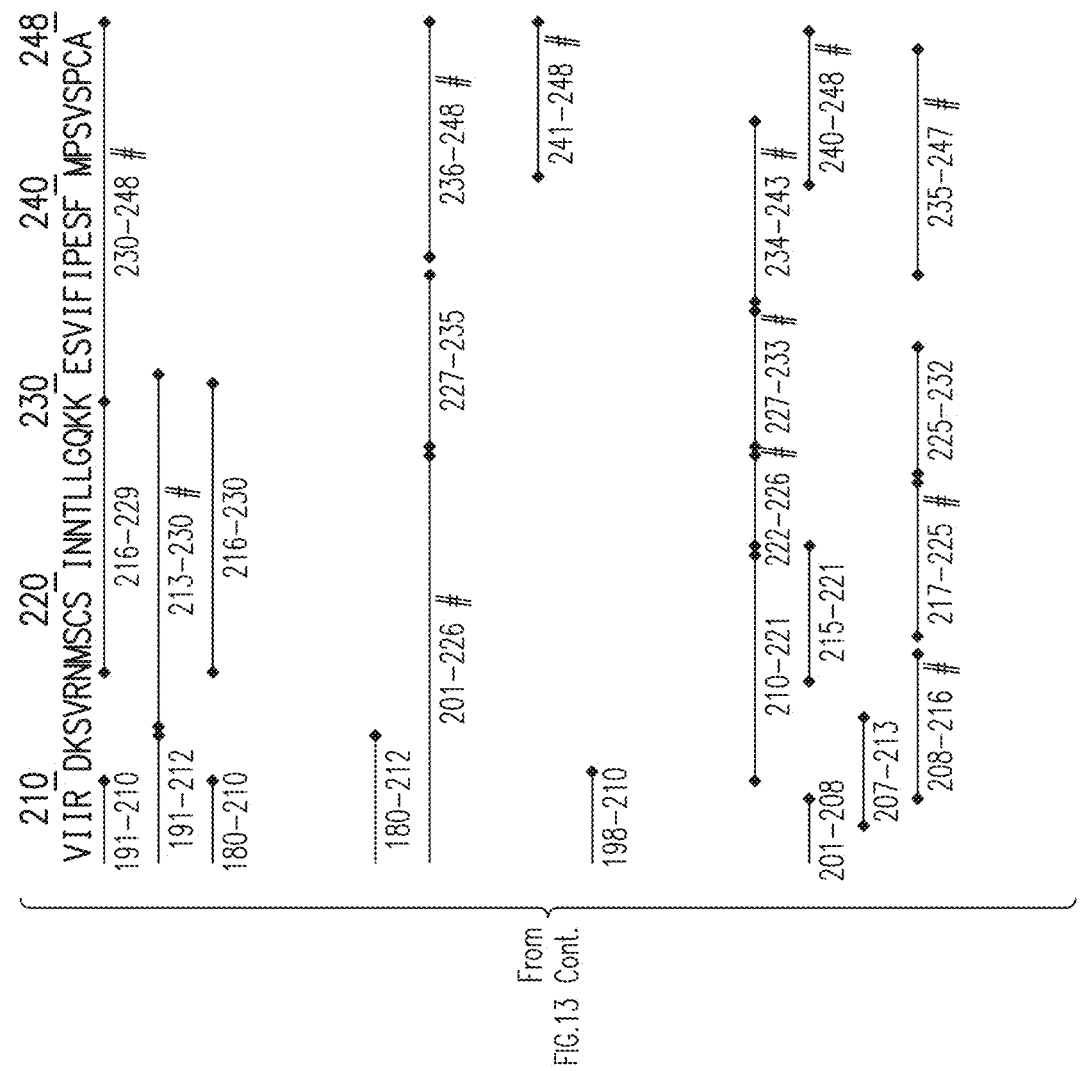

FIG. 13: Trypsin, Chymotrypsin, ASP-N, Elastase and Thermolysin peptides of BTN2A1. 96.37% of the sequence is covered by the peptides identified.

Figure 14:
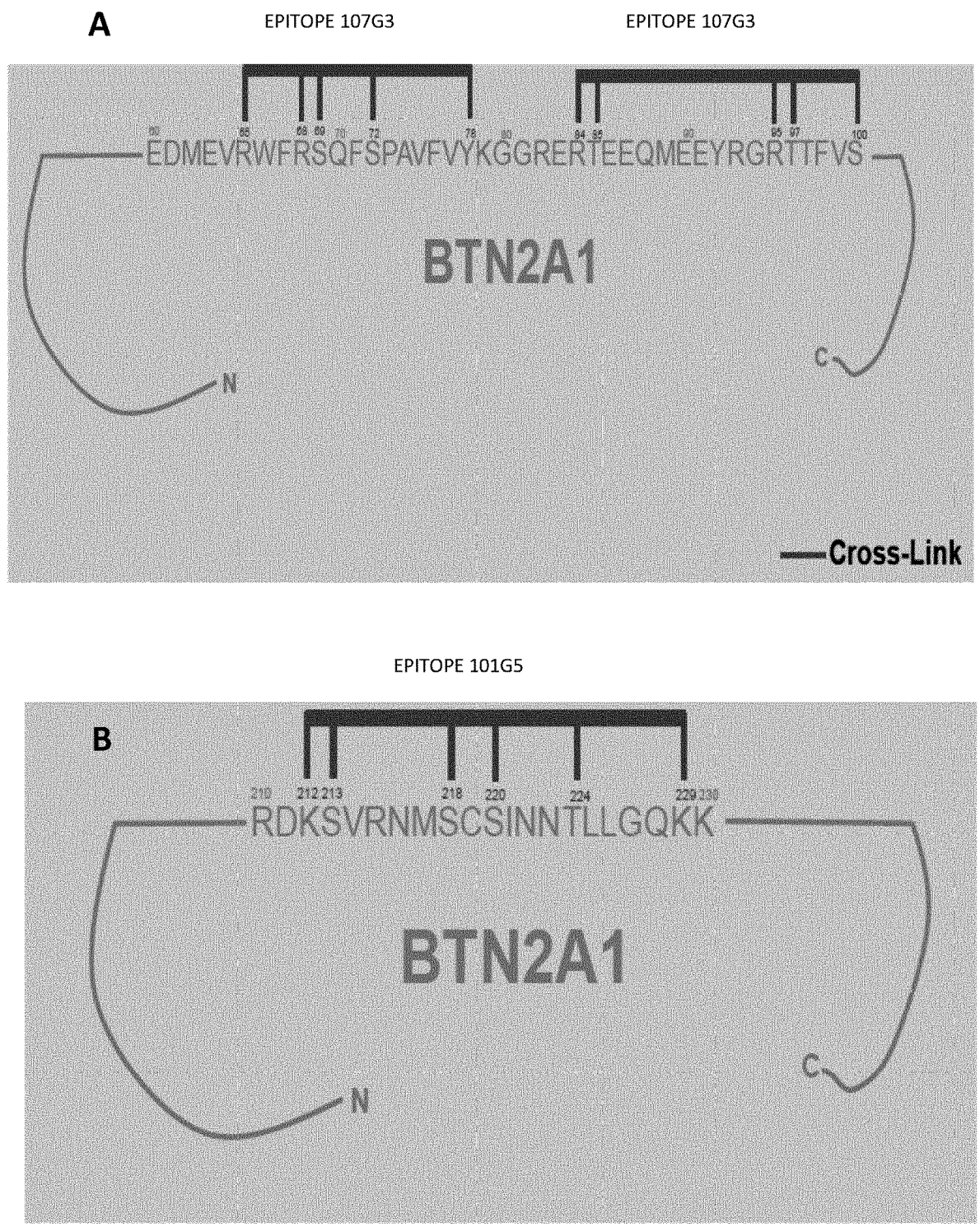

FIG. 14: Interection between the reference mAbs 107G3 and 101G5 with human BTN2A1. A. 107G3/BTN2A1. B. 101G5/BTN2A1.

Figure 15:
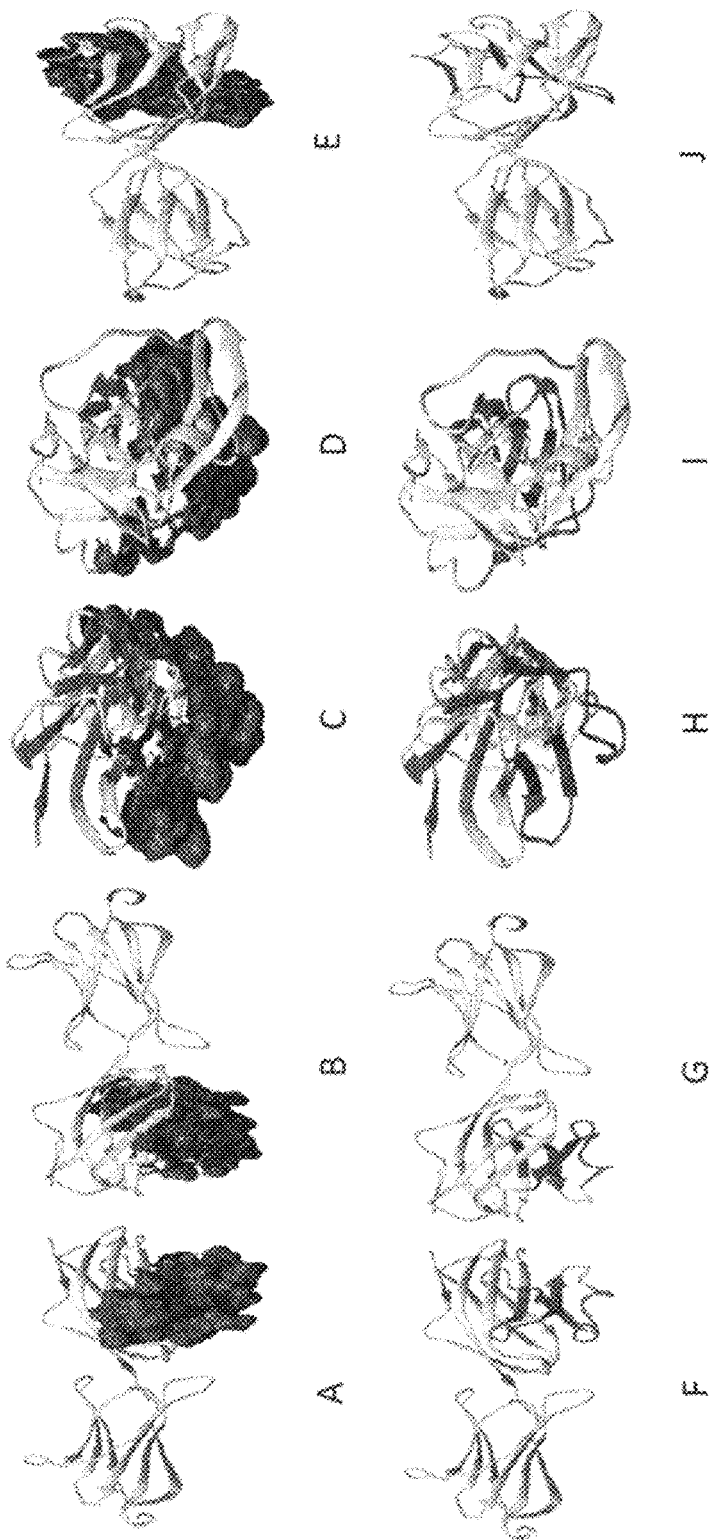

FIG. 15: Interaction BTN2A1/107G3. BTN2A1 PDB structure 4F9P was colored in grey on the epitope site. BTN2A1 amino acids colored in blue are corresponding to 65-78 (RWFRSQFSPAVFVY) and 84-100 (RTEEQMEEYRGRTTFVS) of BTN2A1 sequence provided. A, B, C, D, E: ribbon/surface representation of front view (A); back view (B), side view 1 (C), side view 2 (D) and top view (E). F, G, H, I, J: ribbon representation of front view (F); back view (G), side view 1 (H), side view 2 (I) and top view (J).

Figure 16:
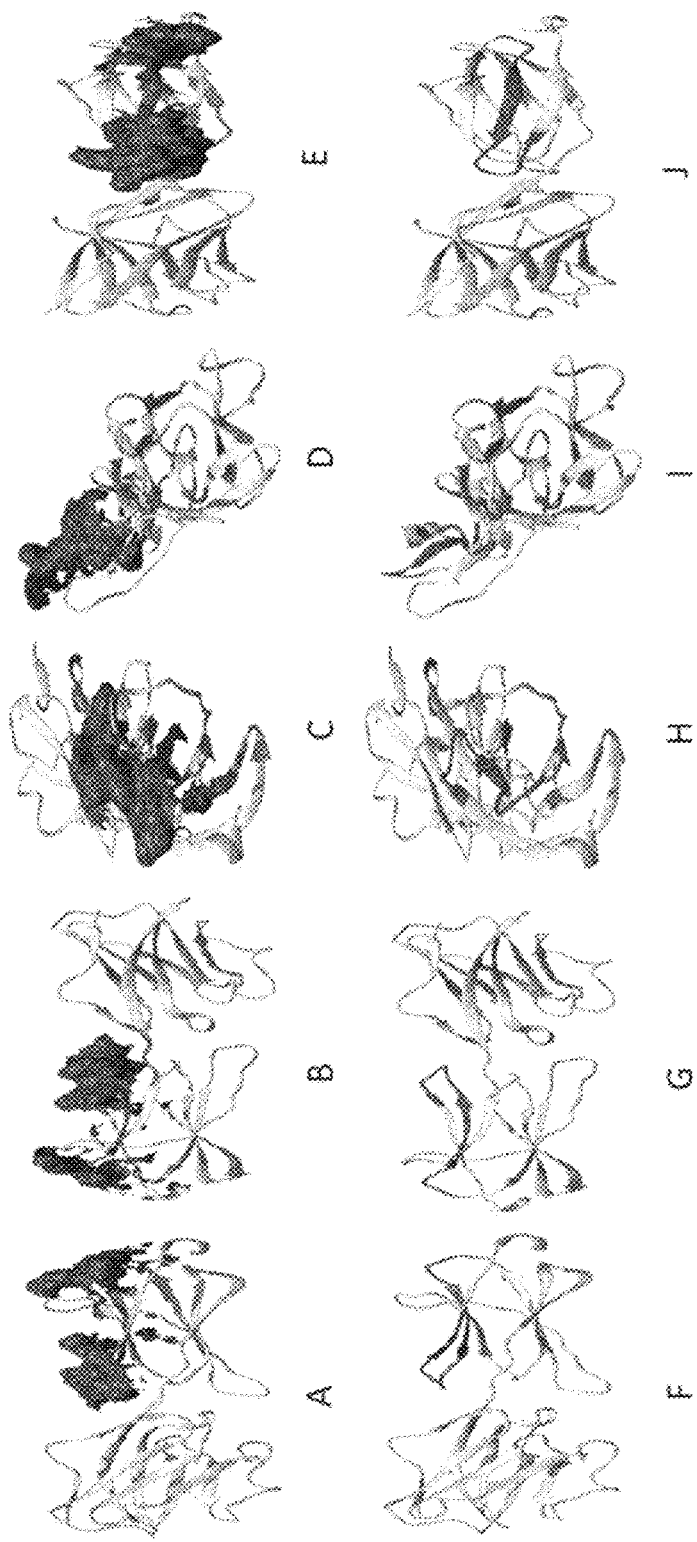

FIG. 16: Interaction BTN2A1/101G5. BTN2A1 PDB structure 4F9P was colored in grey on the epitope site. BTN2A1 amino acids colored in blue are corresponding to 212-229 (KSVRNMSCSINNTLLGQK) of BTN2A1 sequence provided. A, B, C, D, E: ribbon/surface representation of front view (A); back view (B), side view 1 (C), side view 2 (D) and top view (E). F, G, H, I, J: ribbon representation of front view (F); back view (G), side view 1 (H), side view 2 (I) and top view (J).

Figure 17:
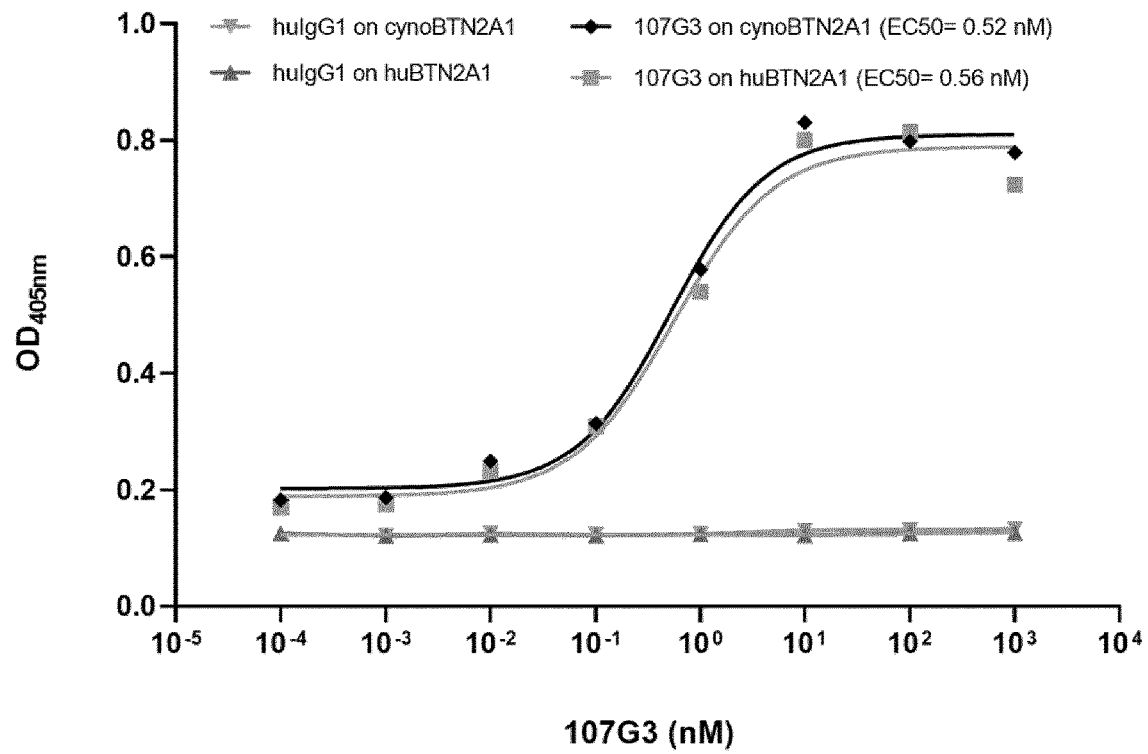
Figure 17:
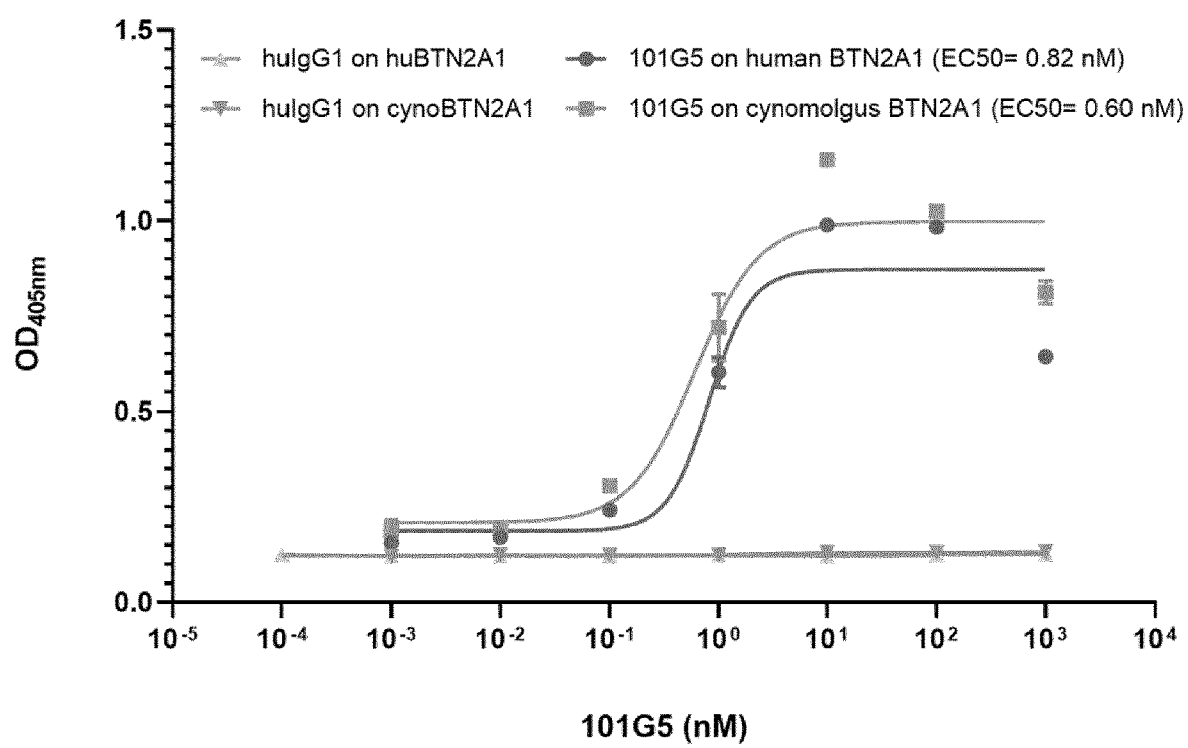

FIG. 17: Assessment of cross-reactivity of the reference anti-BTN2A1 101G5 and 107G3 mAbs against cynomolgus BTN2A1 ortholog. ELISA-based measurement of 107G3 and 101G5 binding to recombinant human BTN2A1-Fc fusion protein or recombinant cynomolgus BTN2A1-Fc fusion protein coated on ELISA plate. Graphs depict dose-response curves allowing EC50 calculation by nonlinear regression using a variable slope model.

EXAMPLES

Material and Methods

Cell Culture, Monocytes and NK Cell Sorting:

Peripheral blood mononuclear cells (PBMCs) were obtained from EDTA (Ethylene Diamine-tetraacetic acid)-buffy coats from healthy donors (HD) provided by the local Blood Bank (Etablissement Français du Sang (EFS)-Marseille-France) and isolated by centrifugation on density gradient (Eurobio). Fresh PBMCs were cultured at 37° C., 5% $CO_2$ in Roswell Park Memorial Institute medium 1640 (RPMI; Lonza) supplemented with 10% fetal bovine serum (FBS) and 1% Penicillin/Streptomycin (P/S).

Natural Killer (NK) cells were sorted from fresh PBMCs by negative selection using EasySep™ Human NK Cell Enrichment Kit (StemCell Technologies) following manufacturer's instructions. Human CD14+ monocytes were sorted by using CD14+ Microbead kit (Miltenyi) following manufacturer's instructions. Monocytes were cultured at a density of $10^6$ cells/mL in RPMI supplemented with 1% L-glutamine, 100 U/mL Penicillin/streptomycin, 1 mM Sodium Pyruvate, 10 mM HEPES, 0.1 mM non-essential amino acids and 10% FBS (all from Thermofisher), during 5 days at 37° C. Pancreatic adenocarcinoma cell line PANC-1 was cultured in RPMI supplemented with 10% FBS. Once grown to 90% confluence, culture medium was discarded, and cells were rinsed twice in PBS 1×. PANC-1 cells were then cultured in RPMI supplemented with 5% FBS for further 24 h (30 mL per 175 $cm^2$ flasks to get a concentrated supernatant). PANC-1 conditioned-medium was then collected, filtered (0.2 μM) and stored at −20° C. until use. Other human cell lines and their corresponding culture media are summarized in the table 1 below:

TABLE 1

| Cell Line | Tissue | Disease | Cell Type | Medium | |
|---|---|---|---|---|---|
| HEK-293T | embryonic kidney | NA | Epithelial | DMEM Glutamax | 10% FBS 1 mM |
| DU-145 | prostate | carcinoma | Epithelial | RPMI Glutamax | NaPyr |
| MDA-MB-231 | breast | Adenocarcinoma | Epithelial | DMEM Glutamax | |
| A-549 | lung | carcinoma | Epithelial | F-12K Medium | |
| HT-29 | colon | colorectal adenocarcinoma | Epithelial | DMEM Glutamax | |
| HCT-116 | colon | colorectal carcinoma | Epithelial | McCoy's 5a | 10% FBS |
| RAJI | B lymphoblast | Burkitt Lymphoma | B lymphocyte | RPMI Glutamax | 10% FBS 1 mM |
| HL60 | Peripheral blood | Acute promyelocytic leukemia | Promyeloblast | | NaPyr |

The following human cell lines were obtained from the American Type Culture Collection: Daudi (Burkitt's lymphoma), Jurkat (acute T cell leukemia), MDA-MB-134 (breast ductal carcinoma) and HEK-293T (embryonic kidney). The human pancreatic adenocarcinoma cell line L-IPC (PDAC087T) was kindly given by Dr. Juan IOVANNA. Daudi and Jurkat cells, as well as PBMCs, were cultured in RPMI 1640 medium supplemented with 10% foetal calf serum (FCS), 1% Na-Pyruvate, 1% L-glutamine (all from Life technologies). HEK-293T BTN2 KO cells were generated by CRISPR-Cas9-mediated inactivation of all isoforms of BTN2 (data not shown). MDA-MB-134, L-IPC, HEK-293 cells and HEK-293T BTN2 KO cells were cultured in DMEM medium (Life Technologies) with 10% FCS. Hybridomas were cultured in DMEM/Ham's F12 (1:1) (ThermoFisher Scientific), 4% FetalClone I (Hyclone), Chemically Defined Lipid Concentrate (1:250), 1% Glutamine, 1% sodium pyruvate and 100 μg/mL PenStrep (all from ThermoFisher Scientific). For collection of hybridoma supernatants, hybridomas were cultured for 4-5 days without Fetalclone.

For assessment of anti-BTN2A1 mAbs specificity, HEK-293T BTN2 KO cells were transfected independently with pcDNA3-Zeo-BTN2A1-CFP plasmids, which encode BTN2A1 and BTN2A2 CFP(Nter)-fusion proteins, using Lipofectamine 3000 reagent (Thermofisher Scientific) according to manufacturer's instructions.

Identification of the Reference Anti-BTN2A1 mAb 107G3

Mouse anti-human BTN2A1 antibodies were generated by immunizing 48 mice, bearing 6 different MHC combinations, with recombinant human BTN2A1-Fc fusion protein. Mice were bled after 21 days and serum titer of BTN2A1-specific polyclonal antibodies was determined via Luminex assay. Mice displaying the highest BTN2A1-specific antibodies titer were euthanized. Splenic B cells were isolated via positive selection and underwent PEG-induced fusion to myeloma cells for hybridoma generation.

Hybridomas were cloned by limiting dilution and hybridoma supernatants underwent two rounds of screening for target specificity and their capacity to induce Vγ9Vδ2-T cell degranulation (FIGS. 1c and 2), and lead to the identification of the reference mAb 107G3. Sequencing of VH and VL regions of these subclones was performed (see Table 1).

Expansion of Vγ9/Vδ2-T Cells

Effector Vγ9/Vδ2-T cells were established by culturing PBMCs from HV in presence of Zoledronate (Sigma, 1 μM) and recombinant human (rh)IL-2 (Proleukin, 200 IU/mL) starting at Day 0. From Day 5, rhIL-2 was renewed every other day and cell density was kept at $1.15×10^6$/mL for a total of 15 days. The last day, the purity of Vγ9/Vδ2-T cells was evaluated by flow cytometry. Only cell cultures that reached purity of Vδ9/Vδ2-T cells higher than 80% were selected to be used in functional tests. Purified Vδ9/Vδ2-T cells were frozen until use.

Luminex Assay

Magnetic COOH beads (Biorad) were conjugated to rhBTN2A1 protein (R&D) according to manufacturer's instructions and beads were stored in storage buffer (Biorad) at −20° C. until use. For titration of mouse sera, serial serum dilutions were made in Luminex assay buffer (Nanotools) starting at 1:50, by dilution steps 1:4; 100 μL bead suspension were mixed with 100 μL serum dilution and incubated for 1 hr at RT, after which beads were washed 3-times in washing buffer, incubated with 1 μg/mL biotinylated goat anti mouse IgG-Fc in Luminex assay buffer, and had 3 further washes in Luminex assay buffer. Finally, beads were incubated for 1 hr with 1 μg/mL streptavidin PE in Luminex assay buffer, before 3 final washes in Luminex read buffer (Nanotools). Beads were resuspended in Luminex read buffer and data were acquired on a Luminex 100/200 system. For hit identification, 30 μL supernatant were transferred into 96 well plates, and 90 μL Luminex assay buffer were added. One hundred microliters of bead suspension were mixed with 100 μL supernatant dilution and incubated for 16 hrs at RT, before proceeding to the protocol described above. For hit identification, those with the highest affinity for the target and the lowest affinity for an irrelevant control protein (Rank-Fc) were selected. For affinity/Kd calculation, hybridoma supernatants underwent serial dilution in Luminex assay buffer starting at 40.000 μM, by dilution steps 1:4, and were analyzed as described above. Kd corresponds to midpoint of the corresponding binding curve.

Flow Cytometry

PBMCs, purified Vγ9Vδ2-T cells-T cells or cell lines were incubated with specified mAbs before analysis on a BD LSRFortessa (BD Biosciences), CytoFlex LX or CytoFlex S (Beckman Coulter) using FlowJo 10.5.3 software (FlowJo). Antibodies used for Vγ9Vδ2-T cell degranulation assay were: anti-CD107a-FITC (BD Biosciences), anti-CD107b-FITC (BD Biosciences), anti-CD3-PeVio700 (Miltenyi), anti-PanTγδ-PE (Miltenyi), live/dead near IR (Thermofisher). All immune stainings performed using 10 μg/mL of purified mAbs, in presence of FcR Block reagent (Miltenyi), goat anti-mouse-PE 1:100 (Jackson Immunoresearch), and live/dead near IR (Thermofisher). Mouse anti-human CD277 (also known as BTN3A; clone 103.2 with IgG2a isotype) was previously disclosed (WO2012/080351). For assessment of anti-BTN2A1 mAbs specificity, 24 hours after transfection, HEK-293T BTN2 KO cells ($5 \times 10^4$/sample) were collected and stained with the indicated concentrations (5 ng/mL to 75 μg/mL) of anti-human BTN2A1 107G3 mAb as described above. Mouse IgG1 antibody (Miltenyi) was used as isotype control for staining.

Functional Assay on Vγ9/Vδ2-T Cells

Purified Vγ9/Vδ2-T cells from HV were cultured overnight in rhIL-2 (200 UI/mL). Then, Vγ9/Vδ2-T cells were co-cultured at 37° C. with the indicated target cell lines (at effector: target (E:T) ratio of 1:1) with or without the following mAbs (50 μL of hybridoma supernatant or 10 μg/ml purified mAb, as indicated): anti-BTN2A1 mAbs, mIgG1 (isotype control antibody) or hybridoma culture medium. Phorbol 12-myristate 13-acetate (PMA, 20 ng/mL) with ionomycine (1 μg/mL) were used as positive control for Vγ9/Vδ2-T cell activation. For first round of hybridoma supernatant screening, culture supernatants were collected after 4 hours and tested for their content on IFNγ, as an indicator of Vγ9/Vδ2-T cell activation, using the Human IFNγELISA set (BD Biosciences). For second round of hybridoma supernatant characterization, Vγ9/Vδ2-T cell degranulation was assessed by a 4 hours incubation in presence of GolgiStop (BD Biosciences) and soluble CD107 (a&b)-FITC. After 4 hours, cells were collected, fixed in PBS 2% paraformaldehyde and analyzed on a CytoFlex LX (Beckman Coulter) using FlowJo 10.5.3 software (FlowJo). Proliferation of Vγ9/Vδ2-T Cells Vδ9/Vδ2-T cells were isolated from PBMCs of healthy donors using anti-TCR γδ microbead kit (Miltenyi Biotec). The purity of γδ-T cells assessed by flow cytometry was greater than 80%. γδ-T cells were labeled with CellTrace Violet for 20 minutes at 37° C. Then, $5 \times 10^5$ CellTrace-labeled cells were cultured in 96-well round-bottom plates in the presence of IL-2 (200 UI/ml), with or without pAg, and with or without purified anti-BTN2A1 107G3 antibody (10 μg/ml). After 5 days of culture, CellTrace dilution was evaluated by flow cytometry on a CytoFlex LX (Beckman Coulter) using FlowJo 10.5.3 software (FlowJo).

Statistics:

For Vγ9/Vδ2-T cell degranulation, results are expressed as mean±SEM. $EC_{50}$ of purified anti BTN2A1 mAb on BTN2A1-transfected HEK-293T BTN2 KO cells was determined based on log(dose) response curves after non-linear regression following a variable-slope model. All analyses were performed using GraphPad Prism 7.04 software (GraphPad).

Identification of the Reference Anti-BTN2A mAb 101G5

After VH and VL sequencing, 23 anti-BTN2A mAbs obtained from mouse hybridoma generation as described above, were produced under a chimeric IgG1 format. Briefly, murine VH and VK anti-BTN2A mAb sequences were synthesized in vitro and amplified by PCR using PrimeSTAR Max DNA Polymerase (Takara). PCR products were cloned in heavy chain and light chain expression vectors (MI-mAbs) using In Fusion system (Clontech), and plasmids were transformed into Stellar competent cells (Clontech). Vector sequencing (MWG Eurofins) was performed in order to validate anti-BTN2A mAbs, before large scale (maxi) preparation of plasmid for further transfection. Vectors encoding matched light and heavy chains for each anti-BTN2A clone were transiently transfected in HEK-293 cells ($2.9 \times 10^6$ of cells/mL) with a ratio heavy chain/light chain 1:1.2, and medium was renewed after 18h. Seven days after transfection, culture supernatants were harvested for mAb purification. Affinity purification of antibodies was performed with Protein A Sepharose Fast Flow (GE Healthcare), overnight at 44° C. Binding buffer was 0.5 M Glycine, 3M NaCl, pH8.9. Elution was performed with the following buffer: 0.1 M Citrate pH3. Samples were neutralized right after elution with 1M Tris-HCl, pH9 (10% v/v). Finally, chimeric anti-BTN2A mAbs were dialyzed into PBS 1× and filtered through 0.22 μM filters (Millex GV hydrophilic PVDF, Millipore). Chimeric anti-BTN2A mAb concentration was determined in a Nanodrop 2000 Spectrophotometer (ThermoScientific) taking into account the extinction coefficient of the antibodies. Purity, as defined by the fraction of mAb monomers, was determined by UPLC-SEC using an Acquity UPLC-HClass Bio (Waters), with an Acquity UPLC Protein-BEH-200A, 1.7 μm 4.6×50 mm column (Waters). Antibody mass was determined in a Xevo G2-S Q-T of mass spectrometer (Waters) using a reversed phase column (PLRP-S 4000 A, 5 μm, 50×2.1 mm (Agilent technologies). All samples were analyzed after de-glycosylation with PNGase F glycosidase (New England Biolabs) at 37° C. When an unexpected mass was found, the primary amino acid sequence was analyzed using bioinformatic tools to identify putative glycosylation sites within the Fab region. SDS-PAGE of purified antibodies allowed detection of fragmentation and/or aggregation of the final material stain free Mini protean TGX gel 4-15 (Biorad). Endotoxin level was determined using a Chromogenic LAL Limulus Amebocyte Lysate kinetic assay (Charles River Endosafe) using a ClarioStar spectrophotometer (BMG Labtech).

In Vitro Macrophage Polarization Assays:

M1 or M2 macrophages were polarized from sorted monocytes from healthy donors. To this end, sorted monocytes were cultured in presence of GM-CSF or M-CSF (40 ng/mL; Miltenyi) to generate M1 or M2 macrophages, respectively. After 5 days, the resulting macrophages were either collected for phenotype analysis, or stimulated with LPS (200 ng/mL) for further 2 days. In some experiments, IL-4 (20 ng/mL) was added to M2 macrophages at day 4, which resulted in generation of "M2+IL-4" or macrophages. In some experiments, M2 macrophages were generated by culturing monocytes in presence of PANC-1 cancer cell-conditioned medium (diluted 30% v/v in culture medium, at day 0 and day 3) without M-CSF supplementation. The resulting M2 macrophages are called "Tum-ind-M2" in this application. In order to screen anti-BTN2A mAbs for their ability to modulate M2 differentiation, M2 macrophages were generated from monocytes, as described above, with or without chimeric anti-BTN2A mAbs or their isotype control (human IgG1; Sigma) at the indicated concentrations. All mAbs are wet-coated (overnight at RT in PBS 1x). As control for M2 differentiation inhibition, GM-CSF (40 ng/mL) and IFNγ (100 ng/mL, BioTechne) were added to monocytes during M-CSF-induced M2 polarization. M1 macrophages polarized in presence of GM-CSF were used as phenotype control. After polarization, the resulting macrophages and their culture supernatants were collected, and the expression of M1- and M2-related markers at the plasma membrane was assessed by flow cytometry. In addition, cytokine content in culture supernatants was quantitated using IL-10 and TNFα ELISA kit (ThermoFisher Scientific) following manufacturer's instructions.

In Vitro M2 Macrophage Reversion Assays:

M2 macrophages were generated from monocytes in presence of M-CSF as described above in absence of the reference mAbs. M2 macrophages were collected and cultured for 2 days, with or without LPS, on culture wells that were previously wet-coated overnight with 10 µg/mL of the reference antibodies or their control isotype mAb (human IgG1 from Sigma). As controls of M2 reversion, GM-CSF (40 ng/mL) and IFNγ (100 ng/mL) were added to M2 macrophages culture for 2 days. M1 macrophages polarized in presence of GM-CSF were used as phenotype control. After reversion experiments, macrophages reverted without addition of LPS were collected for phenotype analysis by flow cytometry. Culture supernatants from LPS-stimulated reverted macrophages were harvested cytokine quantitation using ELISA.

In Vitro Assays on M2 Macrophage-Mediated Inhibition of T Cell Proliferation and IFNγ Production M1, and M2 macrophages were generated with or without addition of the reference antibodies or their isotype control mAb as described above. CD3+ T cells were sorted from healthy donor PBMCs by using the CD3+ Microbead kit (Miltenyi) according to manufacturer's instructions and frozen until the co-culture. Activated CD3+ T cells were generated as follow: CD3+ T cells were stained with 5 µM CellTrace Violet dye (ThermoFisher Scientific), then $10^5$ such cells were cultured in X-Vivo 10 medium supplemented with 20 U/mL IL-2 (Miltenyi), LPS (200 ng/mL) and CountBright absolute counting beads ($5 \times 10^3$ per well, ThermoFisher Scientific) in 96-well flat-bottom plates, previously coated with 1 µg/mL anti-CD3 mAb (clone OKT3, BD biosciences). For co-culture with macrophages, $2 \times 10^4$ allogeneic M1, M2, or macrophages polarized in presence of M-CSF and the reference mAbs or their control isotype, were added to activated allogeneic CD3+ cells. After 5 days of co-culture, 20 ng/mL PMA and 0.5 µg/mL ionomycin were added to the co-culture in order to enhance cytokine production, in presence of GolgiStop Protein transport inhibitor for 5 hours. Then, cells were recovered for phenotype analysis by flow cytometry. CellTrace dilution was used as an indicator of CD3+ T cell proliferation. Results of phenotype and proliferation were expressed in percentage or absolute cell number per mL (after calibration with absolute counting beads).

Natural Killer (NK) Challenge with the Reference Anti-BTN2A1 mAbs:

Sorted Natural Killer (NK) cells from healthy donors were labelled with and were then cultured at 37° C., 5% $CO_2$ in RPMI supplemented with 10% FBS and 1% P/S, IL-2 (50 UI/mL) with or without IL-15 (10 ng/mL) stimulation. The reference anti-BTN2A mAbs or control isotype (10 µg/mL) were added to the culture on day 0. After 5 days, NK cells were extracellularly phenotyped for the expression of activation markers. NK activation was assessed by induction of CD69 and CD25 expression (percentage and Median Fluorescence Intensity MFI). Gating strategy for NK cells is shown in FIG. 4. For NK cell cytotoxicity measurement, sorted NK cells from 3 healthy donors were cultured at 37° C., 5% $CO_2$ in RPMI, 10% FBS and 1% P/S with or without IL-2 (50 UI/mL) and IL-15 (10 ng/mL). The reference anti-BTN2A mAbs or control isotype (10 µg/mL) were added on unstimulated or IL-2/IL-15-stimulated NK cells overnight. The next day, NK cells were co-cultured with the indicated blood or carcinoma cell lines at 1:1 ratio, and FITC-labelled anti-CD107a and anti-CD107b mAbs (all from BD Biosciences) were added to the co-culture and incubated for 4 hours. NK cell degranulation was assessed by flow cytometry as the percentage of CD107ab+ cells on non-stimulated or IL-2/IL-15-stimulated NK cells. For calculations of $EC_{50}$ of NK cell degranulation enhancement, the reference anti-BTN2A mAbs and their isotype control mAbs were used at concentrations ranging from 0.005 nM to 300 nM. For cancer cell NK cell-mediated killing assessment, purified NK cells were preincubated overnight with 10 µg/mL of the reference 101G5 and 107G3 mAbs or corresponding IgG1 control at 37° C., 5% $CO_2$ in RPMI supplemented with 10% FBS and 1% P/S IL-2 (50 UI/mL) and IL-15 (10 ng/mL) were used as positive control. The next day, NK cells were co-cultured with the indicated CellTrace-labelled cancer cell lines at 1:1 ratio for 4 hours. Cancer cell death was evaluated by accessing the percentage of caspase 3/7+ cells using CellEvent™ Caspase-3/7 Green Detection reagent (Thermofisher Scientific) on tumor cell lines.

Flow Cytometry:

Prior to staining, PBMCs/NK cells and monocytes/macrophages were incubated 10 min with human Fc block (Miltenyi) or human IgG1 (Sigma) for Fc receptor saturation. Labelled mAbs used were the following: CD14-FITC and -APC-Vio770 (Miltenyi), CD163-VioBlue (Miltenyi), DC-SIGN-PE-Vio770 (Miltenyi), CD80-PE (BD Biosciences), PDL1-APC (BD Biosciences), CD3-PE-CF594 (BD Biosciences) and CD3-BV605 (Biolegend), CD56-PE-Vio770 (Miltenyi) and -BV605 (BD Biosciences), CD69-BV421 (BD Biosciences), CD25-APC (BD Biosciences). Cells were incubated with the antibody cocktail 30 min at 4° C. Dead cells were excluded using a live/dead near IR dye (ThermoFisher Scientific) to define a "live" gate. For intracellular IFNγ staining, extracellularly stained cells were fixed and permeabilized using Intracellular Fixation & Permeabilization Buffer Set (eBioscience) and incubated with APC-labelled anti-IFNγ (BD Biosciences). Acquisition was performed on Fortessa flow cytometer (BD Biosciences)

using FlowJo 10 software. For BTN2A1 and BTN2A2 phenotyping, purified anti-BTN2A1-specific (mAb5) and anti-BTN2A2-specific (mAb17) were used at 10 µg/mL and revealed with PE-labelled anti IgG (H+L) (Jackson Immunoresearch). NK cells were CD45+CD14-CD3-CD56+ cells within the "live" gate, after selection of single cells. Monocytes were CD45+CD19-CD3-CD56-CD14+ cells within the "live" gate, after selection of single cells. Acquisition was performed on Cytoflex LS (Beckman Coulter), iQue Screener (Intellicyt) or Fortessa (BD Biosciences) flow cytometers, and data were analyzed using the FlowJo 10 software. Results are expressed as median fluorescence intensities (MFI) after subtraction of the value obtained with the corresponding staining control.

Octet-Based BTN2A1 Epitope Affinity Measurement and Binning Assay:

After generation of the reference anti-BTN2A antibodies in chimeric IgG1 format, affinities for the 2 different isoforms of this target (BTN2A1 and BTN2A2) were evaluated and competition assays were performed to determine whether these mAbs recognized the same epitope region of BTN2A1. Affinity and binning experiments were performed on an Octet Red96 platform (Fortebio/PALL), system based on Bio-layer interferometry (BLI) technology. For affinity experiments, recombinant human (rh)BTN2A1-Fc (GTP) was biotinylated using EZ-Link™ NHS-PEG4 Biotinylation Kit according to manufacturer's instructions, and biotinylated rhBTN2A2-Fc was purchased from R&D Systems. In the case of BTN2A1 affinity assays, biotinylated rhBTN2A1-Fc was loaded into streptavidin (SA) biosensors (ForteBio) diluted in Kinetic Buffer 1× (ForteBio) with a loading target level of around 1 nm, and chimeric anti-BTN2A antibodies were used as analytes. For BTN2A2 affinity assays, chimeric anti-BTN2A antibodies were loaded into FAB2G sensors (anti human CH1; Fortebio) as described above, and biotinylated rhBTN2A2-Fc was used as analyte. In both cases, analytes remained in solution and their working concentrations were diluted in Kinetic Buffer 10× (ForteBio). For the first run, the standard working concentration ranged from 200 to 3.125 nM. When necessary for the second run, working concentrations were adjusted from 80 to 1.25 nM. All runs (including loading, equilibration, association/dipping of sensors into analyte, dissociation and regeneration) were performed at 30° C. with shaking 1000 rpm. Analysis was performed using a 1:1 or 2:1 Langmuir model (for BTN2A1 or BTN2A2, respectively) calculated by Octet software, which allowed a better fitting calculation. For binning experiments, His-tagged BTN2A1 (rhBTN2A-His) was purchased from R&D Systems. The reference anti-BTN2A antibodies were tested in a pairwise manner against BTN2A1. Binning experiments were performed by following the«in-tandem»format, meaning that rhBTN2A-His was immobilized on the biosensor (anti-Penta-His«HIS1K biosensors; ForteBio/PALL) and presented to the 2 competing antibodies in consecutive steps. For this kinetic screening, the loading of rhBTN2A-His on HIS1K (signal intensity: 1 nm) was followed by an association step with 10 µg/mL of antibody for 3 min, then by a dissociation step of 3 min. rhBTN2A1-His activity was confirmed via a kinetic screening assay performed in the same format as the binning assay (BTN2A1 as ligand/capture on the sensor and antibody as analyte). All antibodies (saturating or competing one) were used at 10 µg/mL, diluted in Kinetic Buffer 1×. For this kinetic screening, the loading of rhBTN2A1-His on HIS1K (signal intensity: 1 nm) was followed by an association step with antibody for 3 min, then by a dissociation step of 3 min. Assay steps were as follow: Baseline→Antigen capture→Baseline→Saturating antibody→Baseline→Competing antibody→Regeneration following an "in-tandem" scheme. Binning data were analyzed using Octet Data Analysis HT 11.1 using epitope bin operation.

Epitope Mapping of the Reference mAbs 107G3 and 101G5

The interactions between BTN2A1 and the reference mAbs 107G3 and 101G5 were assessed by differential assessment of peptide mass fingerprint of BTN2A1 alone of with 107G3 or 101G5. Before starting the epitope mapping, a high-mass MALDI analysis has been performed on rhBTN2A1-Fc protein (GTP Technologies) in order to verify their integrity and aggregation level using an Autoflex II MALDI ToF mass spectrometer (Bruker) equipped with CovalX's HM4 interaction module (CovalX), which confirmed that no non-covalent aggregates or multimers of BTN2A1 were present in the sample. In order to characterize BTN2A1, and to determine the epitope of BTN2A1/107G3 and BTN2A1/101G5, we submitted the sample to trypsin, chymotrypsin, Asp-N, elastase and thermolysin proteolysis followed by nLC-LTQ-Orbitrap MS/MS analysis, using a nLC Ultimate 3000-RSLC system in line with a LTQ-Orbitrap mass spectrometer (Thermo Scientific). For BTN2A1/107G3 and BTN2A1/101G5 complexes, the protein complexes were incubated with deuterated cross-linkers prior to multi-enzymatic cleavage. After enrichment of the cross-linked peptides, the samples were and the data generated were analyzed using XQuest 2.0 and Stavrox 3.6 software. For sample preparation, reduction alkylation was performed as follows: BTN2A1 (4.04 µM) were mixed with DSS d0/d12 (2 mg/mL; DMF) before 180 minutes incubation time at room temperature. After incubation, reaction was stopped by adding 1 µL of Ammonium Bicarbonate (20 mM final concentration) before 1h incubation time at room temperature. Then, the solution was dried using a speedvac before $H_2O$ 8M urea suspension (10 µL). After mixing, 1 µL of DTT (500 mM) was added to the solution. The mixture was then incubated 1 hour at 37° C. After incubation, 1 µl of iodoacetamide (1M) was added before 1 hour incubation time at room temperature, in a dark room. After incubation, 100 µl of the proteolytic buffer were added. The trypsin buffer contains 50 mM Ambic pH 8.5, 5% acetonitrile, the chymotrypsin buffer contains Tris HCl 100 mM, $CaCl_2$ 10 mM pH 7.8; the ASP-N buffer contains Phopshate buffer 50 mM pH 7.8; the elastase buffer contains Tris HCl 50 mM pH 8.0 and the thermolysin buffer contains Tris HCl 50 mM, $CaCl_2$ 0.5 mM pH 9.0. For trypsin proteolysis, 100 µL of the reduced/alkyled BTN2A1 were mixed with 1 µL of trypsin (Roche Diagnostic) with the ratio 1/100. The proteolytic mixture was incubated overnight at 37° C. For chymotrypsin proteolysis, 100 µL of the reduced/alkyled BTN2A1 were mixed with 0.5 µL of chymotrypsin (Roche Diagnostic) with the ratio 1/200. The proteolytic mixture was incubated overnight at 25° C. For ASP-N proteolysis, 100 µL of the reduced/alkyled BTN2A1 were mixed with 0.5 µL of ASP-N(Roche Diagnostic) with the ratio 1/200. The proteolytic mixture was incubated overnight at 37° C. For elastase proteolysis 100 µL of the reduced/alkyled BTN2A1 were mixed with 1 µL of elastase (Roche Diagnostic) with the ratio 1/100. The proteolytic mixture was incubated overnight at 37° C. For thermolysin proteolysis, 100 µL of the reduced/alkyled BTN2A1 were mixed with 2 µL of thermolysin (Roche Diagnostic) with a ratio 1/50. The proteolytic mixture was incubated overnight at 70° C. After digestion formic acid 1% final was added to the solution. After proteolysis, 10 µL of the peptide solution generated by proteolysis were loaded onto a nano-liquid chromatography system (Ultimate 3000-RSLC) with the following settings: A: 95/05/0.1 $H_2O$/ACN/HCOOH v/v/v; B: 20/80/0.1 $H_2O$/ACN/HCOOH v/v/v, gradient 5-40% B in 35 minutes, injected volume 10 µL, precolumn 300-µm ID×5-mm C18 PepMap™, precolumn flow rate 20 µL/min, column 75-µm ID×15-cm C18 PepMapRSLC, column flow rate, 200 nL/min.

ELISA Assay for Human and Cynomolgus BTN2A1 Cross-Reactivity

Cynomolgus BTN2A1 ortholog sequence (XM_015448906.1) was identified after BLAST search using human BTN2A1 aminoacid sequence, and its extracellular domain was cloned into pFUSE-hIgG1FC2 vector (InvivoGen) using EcoRI/EcoRV restriction sites. Recombinant cynoBTN2A1-Fc fusion protein was produced by transfection of the resulting pFUSE-hIgG1FC2-cynoBTN2A1 plasmid into Expi293F™ cells with Expi-Fectamine™ 293 (ThermoFisher) according to manufacturer's instructions. The cell culture supernatant collected on day 6 was used for purification through an affinity purification column. The purified cynoBTN2A1-Fc protein was analyzed by SDS-PAGE and Western blotting for molecular weight and purity measurements. cynoBTN2A1-Fc protein concentration was determined by Bradford assay with BSA as a standard. For ELISA, cynoBTN2A1-Fc protein or recombinant human BTN2A1-Fc (huBTN2A1-Fc, GTP Technologies) were coated (5 µg/mL in 1×PBS) overnight at 4° C. After 3 washes in PBS, plates were saturated with BSA 2% v/v in PBS for 1 h at room temperature, then saturating buffer was discarded. The reference mAbs 101G5 and 107G3 or a control human IgG1 were diluted in PBS BSA 2% in 10-fold cascade dilutions starting from 1 µM to 1 pM, and 100 µL of each dilution were added per well and incubated for 90 minutes at room temperature on a plate shaker. All wells were washed 3 times in PBS before addition of Goat anti-mouse IgG HRP (Jackson ImmunoResearch, 1:10000 dilution in PBS BSA 2%) and incubation for 1 h at room temperature. Then, all wells were washed 3 times in PBS and 1-step ABTS solution (ThermoFisher) was added for binding revelation, as assessed by absorbance at 405 nm in a Spark spectrometer (Tecan). All samples were assessed in duplicates.

Results:

Identification of the Reference Antibody Anti-BTN2A1 107G3

The reference anti-BTN2A1 107G3 antibody was identified as follows: mice were immunized with BTN2A1-Fc antigen and splenocytes from mice presenting with the highest titer of BTN2A1-specific sera were collected and fused with a myeloma cell line to obtain hybridomas. Hybridoma culture supernatants displaying the highest affinity for BTN2A1 were selected for a first round of screening based on their ability to modulate secretion of IFN-γ by Vγ9/Vδ2-T cells. Selected clones from this first round of screening were subcloned and tested for their ability to induce IFN-γ secretion and Vγ9/Vδ2-T cell degranulation and IFN-γ secretion, notably their ability to induce Vγ9Vδ2-T cell degranulation (FIGS. 1c and 2), and leading to the identification of the reference mAb 107G3. Sequencing of VH and VL regions of these subclones was performed (see Table 2 below).

Anti-BTN2A1 107G3 Antibody Induces Vγ9Vδ2-T Cell Degranulation Against Different Cancer Cell Targets Purified Vγ9/Vδ2 T cells were expanded from PBMCs of healthy donors and co-cultured with different cancer cell lines, including Daudi (Burkitt's lymphoma), Jurkat (acute T cell leukemia), L-IPC (pancreatic adenocarcinoma) and MDA-MB-134 (breast carcinoma) as target cells, with or without anti-BTN2A1 107G3 hybridoma culture supernatant. As shown in FIG. 2 and Table 3, the addition of anti-BTN2A1 107G3 hybridoma supernatant lead to an induction of the cytolytic function of Vγ9/Vδ2 T cells, as measured by the percentage of CD107+ degranulating cells, compared to co-cultures with target cells alone, or in the presence of control hybridoma culture medium. PMA/ionomycin treatment of Vγ9/Vδ2 T cells lead to a maximum induction of their cytolitic function independently of the target cell, as expected.

The percentage of CD107+ cells induced by anti-BTN2A1 107G3 hybridoma supernatant ranged from 71.1±7.4% in Daudi cells to 17.1±2.9% in MDA-MB-134 cells vs. 24.9±4.7% and 4.9±0.4%, respectively, in co-cultures with control hybridoma culture medium. In co-cultures of Vγ9/Vδ2 T cells, with all of the cancer cell lines tested as targets, anti-BTN2A1 107G3 induced between 2-fold and 8-fold more Vγ9/Vδ2 T cell degranulation compared to the same co-cultures in the presence of control hybridoma culture medium.

Purified anti-BTN2A1 mAb 107G3 displayed an EC50 of 0.77 µg/mL (95% IC 0.32-13.22 µg/mL) for the induction of Vγ9/Vδ2 T cell degranulation, as depicted by the percentage of CD107+ cells, co-cultured with Daudi cells as targets in the presence of increasing concentrations (0 to 18 µg/ml) of the anti-BTN2A1 107G3 mAb (FIG. 2b).

TABLE 3

| | Anti-BTN2A1 107G3 | Control hybridoma supernatant |
|---|---|---|
| $EC_{50}$ on HEK-293T BTN2 KO + BTN2A1 | 0.32 (95% IC 0.21-0.46) µg/mL | not applicable |
| $EC_{50}$ on Functional assay on Daudi | 0.77 (95% IC 0.32-13.22) µg/ml | not applicable |
| Functional assay on Daudi (% CD107+ cells) | 71.1 ± 7.4% | 24.9 ± 4.7% |
| Functional assay on MDA-MB-134 (% CD107+ cells) | 17.1 ± 2.9% | 4.9 ± 0.4% |
| Functional assay on L-IPC (% CD107+ cells) | 31.1 ± 3.6% | 14.4 ± 0.5% |
| Functional assay on Jurkat (% CD107+ cells) | 25.7 +5.1% | 3.7 ± 0.4% |

Anti-BTN2A1 107G3 Antibody Recognizes the BTN2A1 but not BTN3

In order to establish the specificity of anti-BTN2A1 mAb 107G3 for the BTN2A1 isoform only, HEK-293T BTN2 KO cells, which bear a CRISPR-Cas9-mediated inactivation of both BTN2 isoforms, were transiently transfected with a plasmid encoding BTN2A1 as a CFP-fusion protein. As shown in FIG. 3a, staining with purified anti-BTN2A1 mAb 107G3 was only detected in HEK-293T BTN2 KO cells transfected with the BTN2A1-encoding plasmid, but not HEK-293T BTN2 KO cells alone.

The anti-BTN3 mAb 103.2, which recognizes all BTN3 isoforms, readily detected BTN3 expression in HEK-293T BTN2 KO cells. Hence, anti-BTN2A1 107G3 is specific for the BTN2A1 isoform and does not cross-react with BTN3.

Affinity of Anti-BTN2A1 107G3 mAb for BTN2A1 in Cellulo

In order to measure the affinity of anti-BTN2A1 107G3 mAb for its target, HEK-293T BTN2 KO cells transfected with the BTN2A1-encoding plasmid were stained with increasing concentrations (5 ng/mL to 75 µg/mL) of purified anti-BTN2A1 107G3 mAb or control mIgG1 (FIG. 3b). Non-linear regression analysis of mean fluorescence intensity data found an $EC_{50}$ of 0.32 µg/mL (95% IC 0.21-0.46 µg/mL) for the anti-BTN2A1 107G3 mAb.

Production of Chimeric Anti-BTN2A mAbs, Affinity Measurements and BTN2A Isoform Specificity:

Twenty-three monoclonal antibodies were transiently produced in HEK-293T cells, achieving different ranges of productivity. Most anti-BTN2A antibodies were produced at high levels (>100 mg/L and up to 430 mg/L). One antibody, anti-BTN2A mAb3 (Table 3), presented with very poor production in HEK-293T cells, ranging from 6 to 8 mg/L. Amino acid sequence analysis revealed an N-glycosylation site within its Fab portion, in the CDR1 of its VH. Two other antibodies, anti-BTN2A mAb9 and mAb11, also exhibited an N-glycosylation site within their Fab region (in CDR1_VH for mAb9 and in CDR1_VL for mAb11). Six antibodies exhibited a lower purity level (<95% in monomer) but only anti-BTN2A mAb1 and mAb3 had a purity level <90% (86% and 75%, respectively). All the final purified anti-BTN2A mAb exhibited a very low level of endotoxin (in the range of 0.1 EU/mg). Only mAb3 had a higher endotoxin level (0.73 EU/mg) than the others, but still within the criteria of acceptance (<1EU/mg). The affinity constants ($K_D$, $k_{on}$ and $k_{off}$) of the 23 anti-BTN2A chimeric mAbs were determined for BTN2A1 and BTN2A2 isoforms using Octet technology, by using biotinylated recombinant Fc-fusion soluble proteins. Table 4 recapitulates $K_D$ constants for each anti-BTN2A mAb. For mAb6 and mAb9, $K_D$ calculation was not possible due to the absence of dissociation observed during the time of measurement (koff $<10^{-7}$ s$^{-1}$), which could be explained by an avidity effect of these antibodies slowing down their dissociation from the target. Eight anti-BTN2A mAbs were found to bind only the BTN2A1 isoform (mAb2, mAb3, mAb4, mAb5, mAb6, mAb8, mAb9 and mAb10), 8 anti-BTN2A mAbs were found to bind only the BTN2A2 isoform (mAb16, mAb17, mAb18, mAb19, mAb20, mAb21, mAb22 and mAb23), and 7 mAbs were found to bind both isoforms (mAb1, mAb7, mAb11, mAb12, mAb13, mAb14 and mAb15).

TABLE 4

Chimeric anti-BTN2A mAb production and affinity summary.

| Antibody | Monomer Purity (%) (SEC-UPLC) | Endotox (EU/mg) | Theoretical Mass (Da) (reduced/intact-Kterm) | Actual Mass (Da) (reduced/intact-Kterm) | Productivity (mg/L) | KD (nM) BTN2A1 | KD (nM) BTN2A2 |
|---|---|---|---|---|---|---|---|
| mAb1 (101G5) | 85.66 | 0.09 | MW = 144302 LC = 23236 HC = 48941 | MW = 144331 LC = 23235 HC = 48938 | 158.11 | 0.041 | 4.4 |
| mAb2 (107G3) | 98.41 | 0.04 | MW = 144688 LC = 23749 HC = 48611 | MW = 144661 LC = 23747 HC = 48591 | 246 | 0.41 | No binding |
| mAb3* | 74.9 | 0.73 | MW = 146116 LC = 23451 HC = 49623 | MW = 146093 LC = 23448 HC = 49606 | 6.75 | 0.14 | No binding |
| mAb4 | 100 | 0.1 | MW = 146300 LC = 23556 HC = 49610 | MW = 146275 LC = 23554 HC = 49590 | 58.22 | 0.1 | No binding |
| mAb5 | 98.08 | 0.06 | MW = 146092 LC = 23498 HC = 49564 | MW = 146067 LC = 23496 HC = 49544 | 82.22 | 0.16 | No binding |
| mAb6 | 100 | 0.07 | MW = 146286 LC = 23369 HC = 49790 | MW = 146262 LC = 23366 HC = 49770 | 28.6 | $<10^{-3}$ | No binding |
| mAb7 | 94.72 | 0.07 | MW = 145098 LC = 23460 HC = 49105 | MW = 145105 LC = 23458 HC = 49101 | 279.78 | 0.1 | 7 |
| mAb8 | 98.93 | 0.15 | MW = 146274 LC = 23556 HC = 49597 | MW = 146248 LC = 23554 HC = 49576 | 44.22 | 0.11 | No binding |
| mAb9* | 98.78 | 0.03 | MW = 146790 LC = 23476 HC = 49935 | MW = 146765 LC = 23473 HC = 49921 | 328.89 | $<10^{-3}$ | No binding |
| mAb10 | 98.24 | 0.12 | MW = 147132 LC = 23383 HC = 50199 | MW = 147141 LC = 23381 HC = 50194 | 105.4 | 0.79 | No binding |
| mAb11* | 98.88 | 0.05 | MW = 147422 LC = 23995 HC = 49732 | MW = 147428 LC = 23991 HC = 49733 | 243.3 | 0.008 | 3.2 |
| mAb12 | 93.36 | 0.09 | MW = 143976 LC = 23391 HC = 48613 | MW = 143950 LC = 23388 HC = 48593 | 127 | 0.03 | 3.3 |
| mAb13 | 97.64 | 0.03 | MW = 145140 LC = 23679 HC = 48907 | MW = 145148 LC = 23677 HC = 48903 | 430 | 0.07 | 0.8 |
| mAb14 | 93.57 | 0.08 | MW = 144180 LC = 23440 HC = 48666 | MW = 144154 LC = 23338 HC = 48647 | 75.78 | 0.004 | 2.8 |

TABLE 4-continued

Chimeric anti-BTN2A mAb production and affinity summary.

| Antibody | Monomer Purity (%) (SEC-UPLC) | Endotox (EU/mg) | Theoretical Mass (Da) (reduced/ intact-Kterm) | Actual Mass (Da) (reduced/ intact-Kterm) | Productivity (mg/L) | KD (nM) BTN2A1 | KD (nM) BTN2A2 |
|---|---|---|---|---|---|---|---|
| mAb15 | 97.07 | 0.07 | MW = 143972<br>LC = 23558<br>HC = 48444 | MW = 143945<br>LC = 23556<br>HC = 48424 | 129.78 | 0.012 | 1.2 |
| mAb16 | 98.15 | 0.06 | MW = 146944<br>LC = 23983<br>HC = 49505 | MW = 146953<br>LC = 23981<br>HC = 49503 | 75.5 | No binding | 0.2 |
| mAb17 | 100 | 0.09 | MW = 146976<br>LC = 23983<br>HC = 49521 | MW = 146985<br>LC = 23981<br>HC = 49518 | 84.44 | No binding | 0.3 |
| mAb18 | 97.87 | 0.12 | MW = 146408<br>LC = 23977<br>HC = 49243 | MW = 146415<br>LC = 23975<br>HC = 49239 | 152.56 | No binding | 0.8 |
| mAb19 | 91.73 | 0.04 | MW = 147130<br>LC = 24000<br>HC = 49581 | MW = 147140<br>LC = 23995<br>HC = 49577 | 252.2 | No binding | 0.3 |
| mAb20 | 98.69 | 0.06 | MW = 146584<br>LC = 23970<br>HC = 49338 | MW = 146594<br>LC = 23968<br>HC = 49334 | 238 | No binding | 0.8 |
| mAb21 | 98.05 | 0.09 | MW = 147088<br>LC = 23992<br>HC = 49568 | MW = 147097<br>LC = 23990<br>HC = 49565 | 66.78 | No binding | 0.22 |
| mAb22 | 96.98 | 0.05 | MW = 146952<br>LC = 23508<br>HC = 49984 | MW = 147087<br>LC = 23506<br>HC = 49981 | 312.22 | No binding | 4.7 |
| mAb23 | 100 | 0.03 | MW = 147080<br>LC = 23969<br>HC = 49587 | MW = 147089<br>LC = 23967<br>HC = 49585 | 78.56 | No binding | 0.3 |

*presence of a site of N-glycosylation in VH or VL.

BTN2A1 and BTN2A2 Plasma Membrane Expression on Monocytes and NK Cells:

We sought to determine whether anti-BTN2A mAbs could target non-Vγ9Vδ2 T cell compartments of the peripheral blood, namely monocytes and NK cells, for therapeutic purposes. Hence, we used mAb5 and mAb17 that were found in our octet assays to bind only BTN2A1 or BTN2A2, respectively, for phenotyping monocytes and NK cells from the peripheral blood. As shown in FIG. 4, only anti-BTN2A1 mAb5 stained the plasma membrane of both monocytes and NK cells, with stronger signal observed in monocytes. Hence, BTN2A1 but not BTN2A2 was detected at the plasma membrane of monocytes and NK cells, giving a rational for screening mAbs recognizing BTN2A1 for their ability to modulate immune functions of these immune cell compartments.

Figure 4B:
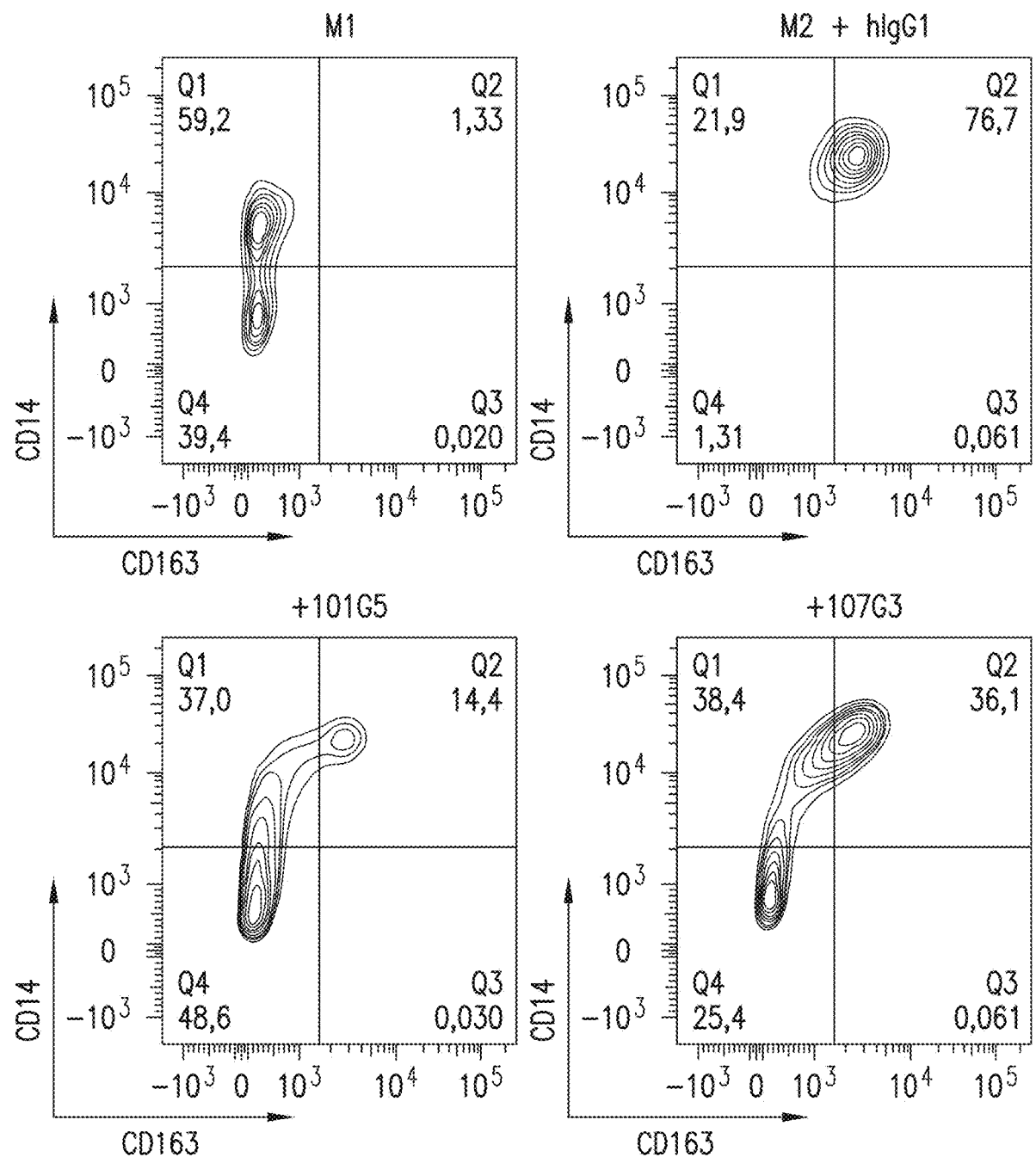

Screening of Anti-BTN2A mAbs for their Ability to Modulate Monocyte to Macrophage Polarization In response to signals from their microenvironment, monocytes can be polarized into M1 or M2 macrophages. M1 macrophages present with pro-inflammatory and anti-tumoral properties, whereas M2 macrophages have anti-inflammatory properties and are associated with tumor development. Given that only BTN2A1 isoform was found at the plasma membrane of monocytes, anti-BTN2A mAbs that recognized BTN2A1-only or both BTN2A1/BTN2A2 isoforms were evaluated for their ability to interfere with monocyte polarization into M2 macrophages in vitro in the presence of M-CSF. M1 macrophages generated in the presence of GM-CSF (CD14+/−CD163−), and M2 (CD14+ CD163+) macrophages generated in the presence of M-CSF, both without mAbs were used as controls for macrophage polarization. After 5 days of in vitro polarization, the expression of CD14 and CD163 at the plasma membrane of M1, M2, and M-CSF-induced macrophages polarized in the presence of anti-BTN2A mAbs or their control IgG1 were assessed by flow cytometry (Table 4). As expected, M1 cells presented with low CD14 expression and undetectable CD163 expression (Table 5 and FIG. 4), whereas M2 macrophages presented with high expression of both markers. Interestingly, anti-BTN2A mAb1, which will be called 101G5 from now on, induced the strongest reduction of the expression of CD14 and CD163 in presence of M-CSF, skewing M-CSF-induced macrophage polarization towards a M1-like phenotype (Table 4 and FIG. 4B). The second best inhibitor of M-CSF-induced M2 macrophage polarization was mAb2, which is 107G3 (Table 5 and FIG. 4B). This contrasts with the phenotype of macrophages obtained in the presence of M-CSF and the control IgG1, which is similar to untreated M2 macrophages.

TABLE 5

Effect of anti-BTN2A mAbs on the expression of CD14 and CD163 after monocyte to M2-macrophage polarization.

| | | M2-related markers (MFI; n = 3) | | | |
|---|---|---|---|---|---|
| | Polarizing | CD14 | | CD163 | |
| | Cytokine | Median | SEM | Median | SEM |
| M1 | GM-CSF | 1047 | 463.6 | 64 | 17.27 |
| M2 | M-CSF | 38878 | 3866 | 6405 | 1051 |
| hIgG1 | | 28070 | 2937 | 4524 | 839.4 |
| mAb1 (101G5) | | 347 | 1892 | 38 | 60.87 |
| mAb2 (107G3) | | 4408 | 8448 | 289 | 1407 |

TABLE 5-continued

Effect of anti-BTN2A mAbs on the expression of CD14 and CD163 after monocyte to M2-macrophage polarization.

| | M2-related markers (MFI; n = 3) | | | |
|---|---|---|---|---|
| Polarizing | CD14 | | CD163 | |
| Cytokine | Median | SEM | Median | SEM |
| mAb3 | 42997 | 3756 | 6757 | 1428 |
| mAb4 | 43853 | 4650 | 6493 | 1129 |
| mAb5 | 45119 | 4004 | 6450 | 949.7 |
| mAb6 | 38277 | 4793 | 5299 | 932.3 |
| mAb7 | 42071 | 3227 | 6337 | 1176 |
| mAb8 | 39483 | 3564 | 6722 | 1199 |
| mAb9 | 43203 | 4869 | 6432 | 1135 |
| mAb10 | 45362 | 3078 | 6737 | 1097 |
| mAb11 | 41519 | 3675 | 6605 | 1090 |
| mAb12 | 44750 | 2845 | 6909 | 1113 |
| mAb13 | 5684 | 9480 | 642 | 1173 |
| mAb14 | 33889 | 10427 | 4614 | 1498 |
| mAb15 | 17411 | 10372 | 2553 | 1429 |

FIG. 5 shows the dose-dependency of the M2-inhibitory effect of the reference 101G5 and 107G3 anti-BTN2A mAbs compared to isotype control in terms of CD14 and CD163 expression inhibition (FIGS. 5A and 5B), as well as increased expression of PDL1 and CD86 that is characteristic of M1 phenotype (FIGS. 5C and 5D). Cytokine secretion profile is also a discriminating feature between M2 vs M1 macrophages. Hence, IL-10 (anti-inflammatory, M2-related) and TNFα (pro-inflammatory, M1-related) secretion were assessed by ELISA after LPS stimulation from culture supernatants of M-CSF-induced macrophages with or without the reference anti-BTN2A mAbs. As shown in FIGS. 5E and 5F, the reference anti-BTN2A mAbs inhibited the secretion of IL-10 and increased TNFα secretion in a dose-dependent manner, in contrast to the isotype control. These observations confirm that 101G5 and 107G3 inhibit M-CSF-induced monocyte polarization into M2 macrophages in terms of phenotype and cytokine secretion by skewing towards a M1-like phenotype. Furthermore, these effects of 101G5 and 107G3 are dose-dependent. The $IC_{50}$ and $EC_{50}$ of each mAb are shown in Table 6. Of note, the lowest $IC_{50}$ and $EC_{50}$ for all parameters but PD-L1 were obtained with 101G5 compared to 107G3.

TABLE 6

$IC_{50}$ and $EC_{50}$ of the reference anti-BTN2A mAbs on M2 vs. M1-related phenotype and cytokine secretion

| | Effect of the reference | $IC_{50}/EC_{50}$ (µg/mL) | |
|---|---|---|---|
| Markers | anti-BTN2A mAbs | 101G5 | 107G3 |
| CD14 | inhibition | 0.51 | 7.7 |
| CD163 | inhibition | 0.43 | 6.2 |
| CD86 | induction | 2.55 | 25 |
| PDL1 | induction | 37.09 | 7 |
| IL-10 | inhibition | 0.105 | 14.8 |
| TNFα | induction | 1.12 | 19.8 |

Other stimuli from the tumor microenvironment have been described to induce M2 macrophage polarization (Mosser and Edwards, Nat Rev Immunol 2008; Mantovani and Allavena, J Exp Med 2015). In addition to M-CSF, one of the most commonly used stimuli to induce M2 polarization is IL-4. We determined the impact of 101G5 and 107G3 on the differentiation of the so called pro-tumoral "M2+IL-4" macrophages, generated from monocytes after stimulation with M-CSF and IL-4. After 5 days of culture in such conditions, 101G5 and 107G3 inhibited the expression of "M2+IL-4"-related markers (CD14, CD163 and DC-SIGN, FIGS. 6A, 6B and 6D) and IL-10 secretion (FIG. 6F), while increasing the expression of M1-related markers (CD86, PDL1) and TNFα secretion (FIGS. 6C, 6E and 6G). Therefore, in a pro-tumor environment (M-CSF and IL-4), 101G4 and 107G3 inhibit "M2+IL-4" differentiation and enhance pro-inflammatory M1 macrophage differentiation.

In addition, the effect of 101G5 and 107G3 on cancer cell-induced M2 polarization from monocytes was assessed by culturing sorted monocytes in the presence of PANC-1 (pancreatic adenocarcinoma cell line)-conditioned culture supernatants. When 101G5 or 107G3 was added in this setting, M2 polarization was inhibited, as shown by decreased expression of M2-related markers (CD14, CD163) and IL-10 secretion (FIG. 7A-C) and the increased expression of the M1-related pro-inflammatory TNFα (FIG. 7D).

Effect of the Reference Anti-BTN2A mAbs 101G5 and 107G3 on M2-Macrophage Reprograming Towards M1

The potential of the reference 101G5 and 107G3 mAbs to revert M2-polarized macrophages towards an M1 phenotype was assessed. For this purpose, M2 macrophages previously polarized in the presence of M-CSF for 5 days were seeded into wells previously coated with 101G5 and 107G3 mAbs and cultured for further 2 or 4 days. Treatment of M2 macrophages with IFNγ served as positive control of M2→M1 reversion. As shown in FIG. 8, M2 macrophages cultured in presence of 101G5 and 107G3 acquired a M1-like phenotype, similar to IFNγ treatment. Indeed, treatment of M2 macrophages with the reference 101G5 and 107G3 mAbs resulted in a decrease of CD14 (FIG. 8A) and CD163 (FIG. 8B) expression, and an increase of CD86 expression (FIG. 8C). Modest to no upregulation of PDL1 was observed after treatment with 101G5 or 107G3, respectively (FIG. 8D). Furthermore, treatment of M2 macrophages with 101G5 and 107G3 inhibited IL-10 secretion (FIG. 8E) and enhanced TNFα secretion (FIG. 8F), indicative of a M1 phenotype.

FIGS. 8G to I show the dose-dependency of the effect of the reference 101G5 and 107G3 mAbs on M2-macrophage reprogramming to M1 macrophages, compared to isotype control in terms of CD163 expression inhibition (FIG. 8G), the decrease of IL-10 and the increase of TNFα secretion (FIGS. 8H and I). The $IC_{50}$ and $EC_{50}$ of each mAb are shown in Table 7 for relevant specific M1/M2 markers where the anti-BTN2A 101G5 mAb shows the best activity on M2-macrophage reprogramming to M1 macrophages.

TABLE 7

$IC_{50}$ and $EC_{50}$ of the reference anti-BTN2A mAbs on M2 reversion

| | Effect of the reference | $IC_{50}/EC_{50}$ (µg/mL) | |
|---|---|---|---|
| Markers | anti-BTN2A mAbs | 101G5 | 107G3 |
| CD14 | inhibition | 3.77 | nd |
| CD163 | inhibition | 6.79 | 15.46 |
| CD86 | induction | 1.14 | nd |
| IL-10 | inhibition | 0.87 | 3.03 |
| TNFα | induction | 6.44 | 80.33 |

The Reference Anti-BTN2A mAbs 101G5 and 107G3 Release M2-Mediated Inhibition of T Cell Proliferation The ability of the reference 101G5 and 107G3 mAbs to affect the function of M2 macrophages namely, inhibition M2-mediated T cell proliferation, was investigated. To this end, allogeneic pre-activated CD3+ T cells were co-cultured with M1, M2, or M2 generated in the presence of the mAbs. As expected, co-culture with conventional M2 macrophages resulted in a decreased number of the CD3+ T cells, as well as decreased T cell proliferation (as assessed by CTV dilution) and production of IFNγ compared to M1 macrophages (FIGS. 9A, C, G, E and I). In contrast, M2 macrophages generated in the presence of 101G5 and 107G3 did not appear to inhibit T cell proliferation, as shown by the higher percentage and absolute numbers of CD3+ T cells compared to cultures of M2 macrophages generated in the presence of control IgG1 (FIGS. 9B, 9H and 9J). Moreover, the percentage and numbers of IFNγ-producing T cells were also higher in co-cultures containing macrophages generated in the presence of 101G5 and 107G3 compared to control IgG1 (FIGS. 9D and 9F).

Hence, in contrast to M2 macrophages induced by M-CSF alone, macrophages generated in presence of 101G5 or 107G3 in addition to M-CSF allow proliferation and Th1 function (IFNγ production) of allogeneic CD3+ T cells, similar to M1 macrophages.

The Reference Anti-BTN2A mAbs 101G5 and 107G3 Trigger NK Cell Activation and Cytotoxicity Since BTN2A1 was found at the plasma membrane of NK cells, the potential ability of 101G5 and 107G3 to modulate NK cell activation was investigated. Purified NK cells from healthy donors were cultured for 5 days in presence of 101G5 or 107G3, with or without further activation (IL-2 and IL-15 or IL-2 only, respectively). As shown in FIG. 10, both 101G5 and 107G3 enhanced the expression of CD69 at the plasma membrane of NK cells in all conditions tested (FIG. 10A). In addition, 101G5 and 107G3 also enhanced the expression of CD25 induced by IL-2 and IL-15 treatment of NK cells (FIG. 10B). Since 101G5 and 107G3 were able to activate purified NK cells, we investigated whether these mAbs could also enhance NK cell cytotoxicity. Hence, NK cell degranulation (% CD107+ cells) against the cancer cell lines HL-60 (myelogenous leukemia), HT-29 (colon carcinoma), MDA-MB-231 (breast adenocarcinoma) and A549 (lung adenocarcinoma) was assessed in presence of 101G5 or 107G3, with or without IL-2 and IL-15 stimulation. As expected, in presence of a control IgG1, only the HL-60 cells triggered NK cell degranulation (FIG. 10O), which was enhanced by stimulation with IL-2 and IL-15 (FIG. 10D). Modest NK cell degranulation against solid tumor cell lines HT-29, MDA-MB-231 and A549 was also observed in presence of control IgG1 and IL2+1L-15. Table 8 summarizes NK cell degranulation against these and other (Raji, HCT116, DU-145) cancer cell lines tested. Interestingly, the reference mAbs 101G5 and 107G3 enhanced NK cell degranulation against the solid tumor cell lines MDA-MB-231 and A549, and to a lesser extent on HT-29, without IL-2+IL-15 stimulation. Addition of IL-2 and IL-15 accentuated the effect of 101G5 and 107G3 in MDA-MB-231, A549 and DU145 cells (Table 8. No such enhancement was observed with HL-60 and Raji blood cancer cell lines by addition of the reference 101G5 or 107G3 mAbs (Table 8 and FIGS. 10C and D). In addition, the reference mAbs 101G5 and 107G3 were able to trigger NK cell degranulation against A549 cell when preincubated with NK cells prior to the co-culture, without further addition of the mAbs to the coculture (FIG. 10E). This suggests a direct effect of the reference 107G3 and 101G5 mAbs by direct binding to NK cells triggering cytotoxicity against cancer cells. Moreover, the dose-dependency of 101G5 and 107G3 on enhancement of NK cell degranulation against the prostate adenocarcinoma DU-145 cell line was assessed. Indeed, 101G5 and 107G3 enhanced NK cell degranulation against DU-145 cells in a dose-dependent manner ($EC_{50(no\ stim)}$=0.14 and 0.54 nM; $EC_{50(IL-2+IL-15)}$=0.08 and 0.2 nM for 101G5 and 107G3, respectively).

TABLE 8

NK cell degranulation (% CD107+ cells) against different cancer cell lines without IL-2 and IL-15 stimulation

| | | IgG1 | | 101G5 | | 107G3 | |
| --- | --- | --- | --- | --- | --- | --- | --- |
| Stimulation | Target cell | Mean | SEM | Mean | SEM | Mean | SEM |
| None | None | 1.74 | 1.26 | 2.06 | 0.95 | 1.81 | 1.03 |
| | HL-60 | 24.57 | 0.71 | 22.43 | 1.31 | 27.23 | 2.29 |
| | Raji | 8.70 | 1.43 | 9.19 | 0.84 | 11.68 | 0.56 |
| | HT-29 | 4.69 | 0.35 | 5.76 | 1.00 | 9.19 | 0.15 |
| | HCT116 | 2.79 | 0.46 | 3.98 | 1.81 | 5.62 | 0.47 |
| | MDA-MB-231 | 2.28 | 0.73 | 7.24 | 1.16 | 9.66 | 1.09 |
| | A549 | 1.68 | 0.07 | 6.78 | 2.44 | 12.57 | 1.15 |
| | DU-145 | 3.29 | 0.19 | 14.6 | 4.91 | 25.1 | 3.13 |
| IL-2 + IL-15 | None | 3.32 | 0.84 | 6.14 | 2.01 | 5.22 | 2.01 |
| | HL-60 | 65.83 | 1.09 | 57.37 | 3.18 | 58.57 | 3.18 |
| | Raji | 21.33 | 2.31 | 28.83 | 0.00 | 24.50 | 0.00 |
| | HT-29 | 22.43 | 2.11 | 20.73 | 2.18 | 19.83 | 2.18 |
| | HCT116 | 25.53 | 2.62 | 27.70 | 1.93 | 26.20 | 1.93 |
| | MDA-MB-231 | 11.85 | 3.26 | 29.00 | 4.00 | 30.70 | 4.00 |
| | A549 | 14.53 | 2.64 | 24.57 | 1.38 | 32.03 | 1.38 |
| | DU-145 | 23.73 | 4.71 | 41.07 | 0.67 | 56.80 | 0.67 |

Finally, we tested the capacity of 101G5 and 107G3 to enhance NK cell-mediated killing of cancer cells by assessing the percentage of caspase 3/7 cells after co-culture of purified NK cells with the leukemia cell line HL-60 or the lung adenocarcinoma cell line A459. As shown in FIG. 11, 101G5 and 107G3 enhanced NK cell-mediated killing of adenocarcinoma A549 cells (~2-fold) but not of HL-60 leukemia cells. Altogether, these observations indicate that 101G5 and 107G3 preferentially enhance NK cell cytotoxicity against cancer cells from solid tumors.

The Reference Anti-BTN2A 101G5 and 107G3 mAbs Recognize Different Epitopes of BTN2A1

Both 101G5 and 107G3 bind to BTN2A1 and share the ability to inhibit M2 macrophage polarization and to enhance NK cell activation and cytotoxicity. Hence, we investigated whether these mAbs recognized the same epitope region on the BTN2A1 protein. Therefore, octet-based binning experiments were performed where 101G5 and 107G3 competed for BTN2A1 binding using an "in-tandem" setting. As shown in FIG. 12, 101G5 and 107G3 did not block each other's binding to BTN2A1, indicating that these two mAbs do not bind to the same epitopic regions on BTN2A1.

Epitope Mapping of the Reference mAbs 101G5 and 107G3

In order to characterize BTN2A1 we submitted the sample to trypsin, chymotrypsin, Asp-N, elastase and thermolysin proteolysis followed by nLC-LTQ-Orbitrap MS/MS analysis. After trypsin proteolysis, 32 peptides were identified in the sequence of BTN2A1, covering 79.84% of the sequence; 27 peptides were identified after chymotrypsin proteolysis, covering 94.76% of the BTN2A1 sequence; 2 peptides were identified after ASP-N proteolysis, covering 12.50% of the BTN2A1 sequence; 33 peptides were identified after elastase proteolysis, covering 89.11% of the BTN2A1 sequence; 29 peptides were identified after thermolysin proteolysis, covering 78.23% of the BTN2A1 sequence. Based on the results obtained, an overlap mapping of the trypsin, chymotrypsin, ASP-N, elastase and thermolysin peptides was designed (FIG. 13). Combining the peptides of Trypsin, Chymotrypsin, ASP-N, Elastase and Thermolysin proteolysis, 96.37% of the BTN2A1 sequence was covered. In order to determine the epitope of BTN2A1/107G3 and BTN2A1/101G5 complexes with high resolution, the protein complexes were incubated with deuterated cross-linkers before being subjected to multi-enzymatic cleavage. After trypsin, chymotrypsin, ASP-N, elastase and thermolysin proteolysis of the protein complex BTN2A1/107G3, the nLC-orbitrap MS/MS analysis detected 17 cross-linked peptides between BTN2A1 and the antibody 107G3.

TABLE 9

Sequences and positions of cross-links between BTN2A1/107G3

| Sequence (sequence protein1- sequence protein 2) | Enzyme | Protein1 | Protein2 | Position Sequence Proteine 1 | Position Sequence Proteine 2 |
| --- | --- | --- | --- | --- | --- |
| LTNYV-EDMEVRWFRS QFSPA-a4-b6 | Elastase | 107G3_VH | BTN2A1 | 29-33 | 60-74 |
| LTNYV-EDMEVRWFRS QFSPA-a2-b9 | Elastase | 107G3_VH | BTN2A1 | 29-33 | 60-74 |
| LTNYV-EDMEVRWFRS QFSPA-a4-b9 | Elastase | 107G3_VH | BTN2A1 | 29-33 | 60-74 |
| WTGGDTNYNS-RWFRSQFSPAV-a8-b4 | Elastase | 107G3_VH | BTN2A1 | 52-61 | 65-75 |
| YCQHSRDLPYAF-FRSQFSPAVF-a10-b3 | Chymotrypsin | 107G3_VL | BTN2A1 | 91-102 | 67-76 |
| GLEWLGVIWTG GDTNYNSALKS R-SQFSPAVFVYKG GR-a18-b4 | Trypsin | 107G3_VH | BTN2A1 | 44-66 | 69-82 |
| LTNYV-EDMEVRWFRS QFSPA-a2-b13 | Elastase | 107G3_VH | BTN2A1 | 29-33 | 60-74 |
| TNYVI-EDMEVRWFRS QFSPA-a3-b13 | Elastase | 107G3_VH | BTN2A1 | 30-34 | 60-74 |
| YSYMHWYQQK PGQPPKL-FVYKGG-a2-b3 | Elastase | 107G3_VL | BTN2A1 | 34-50 | 76-81 |
| YCARGGQLGL-VYKGGRERTEE QMEEYRGRTTF-a4-b8 | Chymotrypsin | 107G3_VH | BTN2A1 | 94-103 | 77-98 |
| KSRLS-RERTEEQMEEY RGRTTFV-a2-b4 | Elastase | 107G3_VH | BTN2A1 | 64-68 | 82-99 |

TABLE 9-continued

Sequences and positions of cross-links between BTN2A1/107G3

| Sequence (sequence protein1-sequence protein 2) | Enzyme | Protein1 | Protein2 | Position Sequence Proteine 1 | Position Sequence Proteine 2 |
|---|---|---|---|---|---|
| ALKSR-VYKGGRERTEE QMEEYRGRTTF-a3-b9 | Thermolysin | 107G3_VH | BTN2A1 | 62-66 | 77-98 |
| SLTNYVISW-KGGRERTEEQM EEYRGRTTFVSK DISRGSVAL-a3-b17 | Chymotrypsin | 107G3_VH | BTN2A1 | 28-36 | 79-110 |
| YCARGGQLGL-VYKGGRERTEE QMEEYRGRTTF-a4-b21 | Chymotrypsin | 107G3_VH | BTN2A1 | 94-103 | 77-98 |
| GQRATISCRASK TVSSSGYSY-RGRTTFVSKDIS RGSVAL-a13-b5 | Chymotrypsin | 107G3_VL | BTN2A1 | 16-36 | 93-110 |
| TVSSSGYSYMH WYQQKPGQPP K-TTEVSK-a11-b5 | Trypsin | 107G3_VL | BTN2A1 | 28-49 | 96-101 |
| TVSSSGYSYMH WYQQKPGQPP K-TTFVSK-a8-b5 | Trypsin | 107G3_VL | BTN2A1 | 28-49 | 96-101 |

Hence, our analysis indicates that the interaction between BTN2A1 and 107G3 mAb includes the following amino acids on BTN2A1: 65, 68, 69, 72, 78; 84, 85, 95, 97, 100. These results are illustrated in FIG. 14A and FIG. 15.

After trypsin, chymotrypsin, ASP-N, elastase and thermolysin proteolysis of the protein complex BTN2A1/101G5, the nLC-orbitrap MS/MS analysis detected 14 cross-linked peptides between BTN2A1 and the antibody 101G5.

TABLE 10

Sequences and positions of cross-links between BTN2A1/101G5.

| Sequence (sequence protein1-sequence protein 2) | Enzyme | Protein1 | Protein2 | Position sequence Protein 1 | Position sequence Protein 2 |
|---|---|---|---|---|---|
| QSPEKSLEWIGEINP STGGTTYNQKFK-DKSVR-a16-b2 | Trypsin | 101G5_VH | BTN2A1 | 39-65 | 211-215 |
| QSPEKSLEWIGEINP STGGTTYNQKFK-DKSVR-a17-b2 | Trypsin | 101G5_VH | BTN2A1 | 39-65 | 211-215 |
| QSPEKSLEWIGEINP STGGTTYNQKFK-DKSVR-a25-b2 | Trypsin | 101G5_VH | BTN2A1 | 39-65 | 211-215 |
| FTVYYM-IRDKSVRNMSCS-a4-b5 | Thermolysin | 101G5_VH | BTN2A1 | 29-34 | 209-220 |
| FKAKATLTVDK-NMSCSINNTLLGQK K-a2-b3 | Trypsin | 101G5_VH | BTN2A1 | 64-74 | 216-230 |
| FKAKATLTVDK-NMSCSINNTLLGQK K-a4-b3 | Trypsin | 101G5_VH | BTN2A1 | 64-74 | 216-230 |
| TTYNQKFKAKA-VRNMSCS-a6-b5 | Elastase | 101G5_VH | BTN2A1 | 58-68 | 214-220 |

TABLE 10-continued

Sequences and positions of cross-links between BTN2A1/101G5.

| Sequence (sequence protein1-sequence protein 2) | Enzyme | Protein1 | Protein2 | Position sequence Protein 1 | Position sequence Protein 2 |
|---|---|---|---|---|---|
| TTYNQKFKAKA-VRNMSCS-a8-b5 | Elastase | 101G5_VH | BTN2A1 | 58-68 | 214-220 |
| INPSTGGTTYNQK-MSCSINNT-a10-b2 | Thermolysin | 101G5_VH | BTN2A1 | 51-63 | 217-224 |
| INPSTGGTTYNQK-MSCSINNT-a8-b2 | Thermolysin | 101G5_VH | BTN2A1 | 51-63 | 217-224 |
| FKAKATLTVDK-NMSCSINNTLLGQK-a4-b5 | Trypsin | 101G5_VH | BTN2A1 | 64-74 | 216-230 |
| LLIYRTSNLASGVPGR-SVRNMSCSINNTLLGQK-a7-b12 | Trypsin | 101G5_VL | BTN2A1 | 47-62 | 213-229 |
| ISSNYLHWYRHKPGFSPK-MSCSINNTL-a2-b8 | Thermolysin | 101G5_VL | BTN2A1 | 29-46 | 217-225 |
| FKAKATLTVDK-NMSCSINNTLLGQK-a2-b14 | Trypsin | 101G5_VH | BTN2A1 | 64-74 | 216-230 |

Hence, our analysis indicates that the interaction between BTN2A1 and 101G5 includes the following amino acids on BTN2A1: 212, 213, 218, 220, 224, 229. These results are illustrated in FIG. 14B and FIG. 16.

The Reference Anti-BTN2A 101G5 and 107G3 mAbs Present Cross-Reactivity with Cynomolgus BTN2A1 Ortholog BTN2A1 orthologs are present in most non-human primates, including cynomolgus (*Macaca fascicularis*). In order to determine the cross-reactivity of the reference mAbs 101G5 and 107G3 with cynomolgus BTN2A1 ortholog (cynoBTN2A1; NCBI ref. XM_015448906.1, 93.31% identity to human BTN2A1), we generated a recombinant Fc-fusion protein containing the ectodomain of cynoBTN2A1 (cynoBTN2A1-Fc) and we performed ELISA assay for assessing the binding of the reference mAbs to this protein. We also performed ELISA using recombinant human BTN2A1-Fc protein in order to compare the affinity of the reference mAbs between human and cynomolgus BTN2A1 orthologs. As shown in FIG. 13, both 101G5 and 107G3 were able to bind cynoBTN2A1 ectodomain with an $EC_{50}$ of 0.60 and 0.57 nM, respectively, which is comparable to the corresponding $EC_{50}$ obtained on huBTN2A1 (0.82 and 0.56 nM, respectively).

TABLE 11

Brief description of useful amino acid and nucleotide sequences for practicing the invention:

| SEQ ID NO: | Type | Description of the sequence | Sequence |
|---|---|---|---|
| 1 | aa | anti-BTN2A1 107G3 mAb heavy chain variable region | MAVLALLLCLMTFPSCALSQVQLKESGPGLVAPSQSLSITCTVSGFSLT NYVISWVRQPPGKGLEWLGVIWTGGDTNYNSALKSRLSISKDNSKSQ VFLKMNSLQTGDTARYYCARGGQLGLRGYWGQGTLVTVSA |
| 2 | aa | anti-BTN2A1 107G3 mAb light chain variable region | METDTLLLWVLLLWVPGSTGDIVLTQSPASLAVSLGQRATISCRASKTV SSSGYSYMHWYQQKPGQPPKLLIYLASNLESGVPARFSGSGSGTDFT LNIHPVEEEDAATYYCQHSRDLPYAFGGGTKLEIK |
| 3 | aa | HCDR1 of 107G3 mAb | NYVIS |
| 4 | aa | HCDR2 of 107G3 mAb | VIVVTGGDTNYNSALKS |
| 5 | aa | HCDR3 of 107G3 mAb | GGQLGLRGY |
| 6 | aa | LCDR1 of 107G3 mAb | RASKTVSSSGYSYMH |
| 7 | aa | LCDR2 of 107G3 mAb | LASNLES |
| 8 | aa | LCDR3 of 107G3 mAb | QHSRDLPYA |
| 9 | nt | HCDR1 of 107G3 mAb | AACTATGTTATAAGC |

TABLE 11-continued

Brief description of useful amino acid and nucleotide sequences for practicing the invention:

| SEQ ID NO: | Type | Description of the sequence | Sequence |
|---|---|---|---|
| 10 | nt | HCDR2 of 107G3 mAb | GTAATTTGGACTGGTGGAGACACAAATTATAATTCAGCTCTCAAATCC |
| 11 | nt | HCDR3 of 107G3 mAb | GGGGGACAGCTCGGGCTACGTGGTTAT |
| 12 | nt | LCDR1 of 107G3 mAb | AGGGCCAGCAAAACTGTCAGTTCATCTGGCTATAGTTATATGCAC |
| 13 | nt | LCDR2 of 107G3 mAb | CTTGCATCCAACCTAGAATCT |
| 14 | nt | LCDR3 of 107G3 mAb | CAGCACAGTAGGGATCTTCCGTACGCG |
| 15 | nt | 107G3 mAb heavy chain variable region | ATGGCTGTCCTGGCGCTACTCCTCTGCCTGATGACTTTCCCAAGC TGTGCCCTGTCCCAGGTGCAGCTGAAGGAGTCAGGACCTGGCCT GGTGGCGCCCTCACAGAGCCTGTCCATCACATGCACTGTCTCTGG GTTCTCATTAACCAACTATGTTATAAGCTGGGTTCGCCAGCCACCA GGAAAGGGTCTGGAGTGGCTTGGAGTAATTTGGACTGGTGGAGAC ACAAATTATAATTCAGCTCTCAAATCCAGACTGAGCATCAGCWGA CAACTCCAAGAGTCAAGTTTTCTTAAAAATGAACAGTCTGCAAACTG GTGACACAGCCAGGTACTACTGTGCCAGAGGGGACAGCTCGGG CTACGTGGTTATTGGGGCCAAGGGACTCTGGTCACTGTCTCTGCA |
| 16 | nt | 107G3 mAb light chain variable region | ATGGAGACAGACACACTCCTGTTATGGGTACTGCTGCTCTGGGTT CCAGGTTCCACTGGTGACATTGTGCTAACACAGTCTCCTGCTTCC TTAGCTGTATCTCTGGGGCAGAGGGCCACCATCTCATGCAGGGCC AGCWACTGTCAGTTCATCTGGCTATAGTTATATGCACTGGTACC AACAGAAACCAGGACAGCCACCCAAACTCCTCATCTATCTTGCATC CAACCTAGAATCTGGGGTCCCTGCCAGGTTCAGTGGCAGTGGGTC TGGGACAGACTTCACCCTCAACATCCATCCTGTGGAGGAGGAGGA TGCTGCAACCTATTACTGTCAGCACAGTAGGGATCTTCCGTACGC GTTCGGAGGGGGGACCAAGTTGGAAATAAAA |
| 17 | aa | Human BTN2A1 | MESAAALHFS RPASLLLLLL SLCALVSAQF IVVGPTDPIL ATVGENTTLR CHLSPEKNAE DMEVRWFRSQ FSPAVFVYKG GRERTEEQME EYRGRTTFVS KDISRGSVAL VIHNITAQEN GTYRCYFQEG RSYDEAILHL VVAGLGSKPL ISMRGHEDGG IRLECISRGW YPKPLTVWRD PYGGVAPALK EVSMPDADGL FMVTTAVIIR DKSVRNMSCS INNTLLGQKK ESVIFIPESF MPSVSPCAVA LPIIVVILMI PIAVCIYWIN KLQKEKKILS GEKEFERETR EIALKELEKE RVQKEEELQV KEKLQEELRW RRTFLHAVDV VLDPDTAHPD LFLSEDRRSV RRCPFRHLGE SVPDNPERFD SQPCVLGRES FASGKHYWEV EVENVIEWTV GVCRDSVERK GEVLLIPQNG FWTLEMHKGQ YRAVSSPDRI LPLKESLCRV GVFLDYEAGD VSFYNMRDRS HIYTCPRSAF SVPRPFFRL GCEDSPIFIC PALTGANGVT VPEEGLTLHR VGTHQSL |
| 18 | aa | Human BTN2A2 | MEPAAALHFS LPASLLLLLL LLLLSLCALV SAQFTVVGPA NPILAMVGEN TTLRCHLSPE KNAEDMEVRW FRSQFSPAVF VYKGGRERTE EQMEEYRGRI TFVSKDINRG SVALVIHNVT AQENGIYRCY FQEGRSYDEA ILRLVVAGLG SKPLIEIKAQ EDGSIWLECI SGGWYPEPLT VWRDPYGEVV PALKEVSIAD ADGLFMVTTA VIIRDKYVRN VSCSVNNTLL GQEKETVIFI PESFMPSASP WMVALAVILT ASPWMVSMTV ILAVFIIFMA VSICCIKKLQ REKKILSGEK KVEQEEEKEIA QQLQEELRWR RTFLHAADVV LDPDTAHPEL FLSEDRRSVR RGPYRQRVPD NPERFDSQPC VLGWESFASG KHYWEVEVEN VMVWTVGVCR HSVERKGEVL LIPQNGFWTL EMFGNQYRAL SSPERILPLK ESLCRVGVFL DYEAGDVSFY NMRDRSHIYT CPRSAFTVPV RPFFRLGSDD SPIFICPALT GASGVMVPEE GLKLHRVGTH QSL |
| 19 | aa | Anti-BTN2A1 101G5 mAb heavy chain variable region (including leader sequence) | MGWNWIFILILSVTTGVHSEVQLQQSGPELVKP GASVKISCKASGYSFTVYYMLVVVKQSPEKSLE WIGEINPSTGGTTYNQKFKAKATLTVDKSSSTAY MQLKSLTSEDSAVYYCARGPSFYALDYWGQGT SVTVSS- |
| 20 | aa | Anti-BTN2A1 101G5 mAb light chain variable region (including leader sequence) | MDFQMQIISLLLISVTVIVSHGEIVLTQSPTTMAA SPGEKITITCSATSSISSNYLHVVYRHKPGFSPKL LIYRTSNLASGVPGRFSGSGSTSYSLTIGTMEA EDVATYYCQQGSSIPRTFGGGTKLEIK |

TABLE 11-continued

Brief description of useful amino acid and nucleotide sequences for practicing the invention:

| SEQ ID NO: | Type | Description of the sequence | Sequence |
|---|---|---|---|
| 21 | aa | HCDR1 of 101G5 mAb | VYYML |
| 22 | aa | HCDR2 of 101G5 mAb | EINPSTGGTTYNQKFKA |
| 23 | aa | HCDR3 of 101G5 mAb | GPSFYALDY |
| 24 | aa | LCDR1 of 101G5 mAb | SATSSISSNYLH |
| 25 | aa | LCDR2 of 101G5 mAb | RTSNLAS |
| 26 | aa | LCDR3 of 101G5 mAb | QQGSSIPRT |
| 27 | nt | HCDR1 of 101G5 mAb | GTCTACTACATGCTC |
| 28 | nt | HCDR2 of 101G5 mAb | GAGATTAATCCTAGCACTGGTGGTACTACCTACAACCAGAAGTTCAAGGCC |
| 29 | nt | HCDR3 of 101G5 mAb | GGCCCGAGCTTTTATGCTCTGGACTAC |
| 30 | nt | LCDR1 of 101G5 mAb | AGTGCCACCTCTAGTATAAGTTCCAATTACTTGCAT |
| 31 | nt | LCDR2 of 101G5 mAb | AGGACATCCAATCTGGCTTCT |
| 32 | nt | LCDR3 of 101G5 mAb | CAGCAGGGTAGTAGTATACCACGCACG |
| 33 | nt | 101G5 mAb heavy chain variable region (including leader sequence) | ATGGGATGGAACTGGATCTTTATTTTAATCCTGTCAGTAACTACAGGTGTCCACTCTGAGGTCCAGCTGCAGCAGTCTGGACCTGAGCTGGTGAAGCCTGGGGCTTCAGTGAAGATATCCTGCAAGGCTTCTGGTTACTCATTCACTGTCTACTACATGCTCTGGGTGAAACAAAGTCCTGAAAAGAGCCTTGAGTGGATTGGAGAGATTAATCCTAGCACTGGTGGTACTACCTACAACCAGAAGTTCAAGGCCAAGGCCACATTGACTGTAGACAAATCCTCCAGCACAGCCTACATGCAGCTCAAGAGCCTGACATCTGAGGACTCTGCAGTCTATTACTGTGCAAGGGGCCCGAGCTTTTATGCTCTGGACTACTGGGGTCAAGGAACCTCAGTCACCGTCTCCTCA |
| 34 | nt | 101G5 mAb light chain variable region (including leader sequence) | ATGGATTTTCAGATGCAGATTATCAGCTTGCTGCTAATCAGTGTCACAGTCATAGTGTCTCATGGAGAAATTGTGCTCACCCAGTCTCCAACCACCATGGCTGCATCTCCCGGGGAGAAGATCACTATCACCTGCAGTGCCACCTCTAGTATAAGTTCCAATTACTTGCATTGGTATCGACATAAGCCAGGATTCTCCCCTAAACTCTTGATTTATAGGACATCCAATCTGGCTTCTGGAGTCCCAGGTCGCTTCAGTGGCAGTGGGTCTGGGACCTCTTACTCTCTCACAATTGGCACCATGGAGGCTGAAGATGTTGCCACTTACTACTGCCAGCAGGGTAGTAGTATACCACGCACGTTCGGAGGGGGGACCAAGCTGGAAATAAAA |
| 35 | aa | *Macaca fascicularis* (Cynomolgus monkey) BTN2A1 | MQRQFSKASRPCLPWVLMEPAAALHFSLPASLILLLLLLRLCALVSAQFTVVGPTDPILAMVGENTTLRCHLSPEKNAEDMEVRWFRSQFSPAVFVYKGGRERTEEQMEEYRGRTTFVSKDISRGSVALIIHNVTAQENGTYRCYFQEGRSYDEAILHLMVAGLGSKPLVEMRGHEDGGIRLECISRGWYPKPLTVWRDPYGRVVPALKEVFPPDTDGLFMVTTAVIIRDKSMRNMSCSISDTLLGQKKESVIFIPESFMPSVSPCVVALPIIVVFLMIIAVCIYWINRLQKETKILSGEKES |

TABLE 11-continued

Brief description of useful amino acid and nucleotide sequences for practicing the invention:

| SEQ ID NO: | Description of the Type sequence | Sequence |
|---|---|---|
| | | ERKTREIAVKELKKERVQKEKELQVKEQLQEEL
RWRRTVLHAVDVVLDPDTAHPDLLLSEDRRSVR
RCPLGHLGESVPDNPERFNSEPCVLGRESFAS
GKHYWEVEVENVIEVVTVGVCRDSVERKEEVLL
RPRNGFVVTLEMCKGQYRALSSPKRILPLKESLC
RVGVFLDYEAGDVSFYNMRDRSHIYTCPRLAFS
VPVRPFFRIGSDDSPIFICPALTGASGITVPEEGLI
LHRVGTNQSLMPVGTRCYGHGMRPTGFIRMRE
ERGIHRTTREEREPDMQNFDLGAHWSNNLPSA
RSREFLNSDLVPDHSLESPVTPGLANKTGEPQA
EVTCLCFSLPSSELRAFPSTATNHNHKATALGS
DLHIEVKGYEDGGIHLECRSTGWYPQPQIQWSN
TKGQHIPAVKAPVVADGVGLYAVAASVIMRGSS
GEGVSCIIRNSLLGLEKTASISITDPFFRNAQPWI
AALAGTLPISLLLLAGASYFLWRQQKEKIALSRET
EREREMKEMGYAATKQEISLRGGEKSLAYHGT
HISYLAAPERWEMAVFPNSGLPRCLLTLILLQLP
KLDSAPFDVIGPPEPILAVVGEDAELPCRLSPNA
SAEHLELRWFRKKVSPAVLVHRDGREQEAEQM
PEYRGRATLVQDGIAEGRVALRIRGVRVSDDGE
YTCFFREDGSYEEALVHLKVAALGSDPHISMQV
QENGEIWLECTSVGWYPEPQVQWRTSKGEKFP
STSESRNPDEEGLFTVAASVIIRDTSVKNVSCYI
QNLLLGQEKEVEIFIPG |

REFERENCES

Throughout this application, various references describe the state of the art to which this invention pertains. The disclosures of these references are hereby incorporated by reference into the present disclosure.

---

The invention claimed is:

1. An anti-butyrophilin-2A (BTN2A) antibody comprising:
a heavy chain variable region CDR1 comprising SEQ ID NO:3, a heavy chain variable region CDR2 comprising SEQ ID NO:4, a heavy chain variable region CDR3 comprising SEQ ID NO:5, a light chain variable region CDR1 comprising SEQ ID NO: 6, a light chain variable region CDR2 comprising SEQ ID NO:7, and a light chain variable region CDR3 comprising SEQ ID NO:8, or
a heavy chain variable region CDR1 comprising SEQ ID NO:21, a heavy chain variable region CDR2 comprising SEQ ID NO:22, a heavy chain variable region CDR3 comprising SEQ ID NO:23, a light chain variable region CDR1 comprising SEQ ID NO:24, a light chain variable region CDR2 comprising SEQ ID NO:25 and a light chain variable region CDR3 comprising SEQ ID NO:26.

2. The anti-BTN2A antibody of claim 1 which comprises:
a heavy chain variable region comprising a sequence having at least 90% identity with the amino acid sequence of SEQ ID NO:1 and a light chain variable region comprising a sequence having at least 90% identity with the amino acid sequence of SEQ ID NO:2, or
a heavy chain variable region comprising a sequence having at least 90% identity with the amino acid sequence of SEQ ID NO:19 and a light chain variable region comprising a sequence having at least 90% identity with the amino acid sequence of SEQ ID NO:20.

3. The anti-BTN2A antibody of claim 1, wherein said anti-BTN2A antibody has at least one of the following functions:
it activates secretion of cytolytic molecules of Vγ9Vδ2T cells,
it activates the cytolytic function of Vγ9Vδ2 T cells, and/or
it activates the proliferation of Vγ9Vδ2 T cells.

4. The anti-BTN2A antibody of claim 3, which competes for binding to BTN2A1 with the reference murine antibody mAb 107G3 comprising (i) a heavy chain variable region comprising the amino acid sequence of SEQ ID NO:1 and (ii) a light chain variable region comprising the amino acid sequence of SEQ ID NO:2.

5. The anti-BTN2A antibody of claim 1, having specificity for the human BTN2A1 isoform.

6. The anti-BTN2A antibody of claim 1, which is a chimeric or humanized antibody.

7. The anti-BTN2A antibody of claim 1, wherein the anti-BTN2A antibody has at least one of the following functions:
it inhibits the polarization of monocytes towards M2 macrophages,
it induces reversion of M2 macrophages towards anti-tumoral M1 macrophages,
it triggers NK cells activation directly, and/or
it enhances NK cell-mediated cytotoxicity.

8. The anti-BTN2A antibody of claim 1 which competes for binding to BTN2A1 with
the reference antibody mAb 107G3 comprising (i) a heavy chain variable region comprising the amino acid sequence of SEQ ID NO:1 and (ii) a light chain variable region comprising the amino acid sequence of SEQ ID NO:2, or
the reference antibody mAb 101G5 comprising (i) a heavy chain variable region comprising the amino acid sequence of SEQ ID NO:19 and (ii) a light chain variable region comprising the amino acid sequence of SEQ ID NO:20.

9. The anti-BTN2A antibody of claim 1, which binds an epitope comprising residues located in positions: 65, 68, 69, 72, 78; 84, 85, 95, 97, and 100 of SEQ ID NO. 17.

10. The anti-BTN2A antibody of claim 1, which binds an epitope comprising residues located in positions 212, 213, 218, 220, 224, and 229 of SEQ ID NO. 17.

11. The anti-BTN2A antibody of claim 1 which does not cross-react with the human BTN3A isoforms, and/or which cross-reacts with the cynomolgus BTN2A1 ortholog.

12. A pharmaceutical composition comprising the anti-BTN2A antibody of claim 1, and at least a pharmaceutically acceptable carrier.

13. A nucleic acid molecule, which encodes a heavy chain and/or a light chain of the anti-BTN2A antibody of claim 1.

14. A host cell comprising the nucleic acid of claim 13.

* * * * *

SEQUENCE LISTING

<160> NUMBER OF SEQ ID NOS: 35

<210> SEQ ID NO 1
<211> LENGTH: 136
<212> TYPE: PRT
<213> ORGANISM: Homo sapiens

<400> SEQUENCE: 1

Met Ala Val Leu Ala Leu Leu Cys Leu Met Thr Phe Pro Ser Cys
 1               5                  10                  15

Ala Leu Ser Gln Val Gln Leu Lys Glu Ser Gly Pro Gly Leu Val Ala
                20                  25                  30

Pro Ser Gln Ser Leu Ser Ile Thr Cys Thr Val Ser Gly Phe Ser Leu
            35                  40                  45

Thr Asn Tyr Val Ile Ser Trp Val Arg Gln Pro Pro Gly Lys Gly Leu
    50                  55                  60

Glu Trp Leu Gly Val Ile Trp Thr Gly Gly Asp Thr Asn Tyr Asn Ser
65                  70                  75                  80

Ala Leu Lys Ser Arg Leu Ser Ile Ser Lys Asp Asn Ser Lys Ser Gln
                85                  90                  95

Val Phe Leu Lys Met Asn Ser Leu Gln Thr Gly Asp Thr Ala Arg Tyr
            100                 105                 110

Tyr Cys Ala Arg Gly Gly Gln Leu Gly Leu Arg Gly Tyr Trp Gly Gln
        115                 120                 125

Gly Thr Leu Val Thr Val Ser Ala
    130                 135

<210> SEQ ID NO 2
<211> LENGTH: 131
<212> TYPE: PRT
<213> ORGANISM: Homo sapiens

<400> SEQUENCE: 2

```
Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Cys Arg Ala Ser Lys Thr
        35                  40                  45

Val Ser Ser Ser Gly Tyr Ser Tyr Met His Trp Tyr Gln Gln Lys Pro
    50                  55                  60

Gly Gln Pro Pro Lys Leu Leu Ile Tyr Leu Ala Ser Asn Leu Glu Ser
65                  70                  75                  80

Gly Val Pro Ala Arg Phe Ser Gly Ser Gly Ser Gly Thr Asp Phe Thr
                85                  90                  95

Leu Asn Ile His Pro Val Glu Glu Asp Ala Ala Thr Tyr Tyr Cys
            100                 105                 110

Gln His Ser Arg Asp Leu Pro Tyr Ala Phe Gly Gly Gly Thr Lys Leu
        115                 120                 125

Glu Ile Lys
    130
```

<210> SEQ ID NO 3
<211> LENGTH: 5
<212> TYPE: PRT
<213> ORGANISM: Homo sapiens

<400> SEQUENCE: 3

```
Asn Tyr Val Ile Ser
1               5
```

<210> SEQ ID NO 4
<211> LENGTH: 16
<212> TYPE: PRT
<213> ORGANISM: Homo sapiens

<400> SEQUENCE: 4

```
Val Ile Trp Thr Gly Gly Asp Thr Asn Tyr Asn Ser Ala Leu Lys Ser
1               5                   10                  15
```

<210> SEQ ID NO 5
<211> LENGTH: 9
<212> TYPE: PRT
<213> ORGANISM: Homo sapiens

<400> SEQUENCE: 5

```
Gly Gly Gln Leu Gly Leu Arg Gly Tyr
1               5
```

<210> SEQ ID NO 6
<211> LENGTH: 15
<212> TYPE: PRT
<213> ORGANISM: Homo sapiens

<400> SEQUENCE: 6

```
Arg Ala Ser Lys Thr Val Ser Ser Ser Gly Tyr Ser Tyr Met His
1               5                   10                  15
```

<210> SEQ ID NO 7
<211> LENGTH: 7
<212> TYPE: PRT
<213> ORGANISM: Homo sapiens

<400> SEQUENCE: 7

Leu Ala Ser Asn Leu Glu Ser
1               5

<210> SEQ ID NO 8
<211> LENGTH: 9
<212> TYPE: PRT
<213> ORGANISM: Homo sapiens

<400> SEQUENCE: 8

Gln His Ser Arg Asp Leu Pro Tyr Ala
1               5

<210> SEQ ID NO 9
<211> LENGTH: 15
<212> TYPE: DNA
<213> ORGANISM: Homo sapiens

<400> SEQUENCE: 9
aactatgtta taagc                                                     15

<210> SEQ ID NO 10
<211> LENGTH: 48
<212> TYPE: DNA
<213> ORGANISM: Homo sapiens

<400> SEQUENCE: 10
gtaatttgga ctggtggaga cacaaattat aattcagctc tcaaatcc                 48

<210> SEQ ID NO 11
<211> LENGTH: 27
<212> TYPE: DNA
<213> ORGANISM: Homo sapiens

<400> SEQUENCE: 11
gggggacagc tcgggctacg tggttat                                        27

<210> SEQ ID NO 12
<211> LENGTH: 45
<212> TYPE: DNA
<213> ORGANISM: Homo sapiens

<400> SEQUENCE: 12
agggccagca aaactgtcag ttcatctggc tatagttata tgcac                    45

<210> SEQ ID NO 13
<211> LENGTH: 21
<212> TYPE: DNA
<213> ORGANISM: Homo sapiens

<400> SEQUENCE: 13
cttgcatcca acctagaatc t                                              21

<210> SEQ ID NO 14
<211> LENGTH: 27
<212> TYPE: DNA
<213> ORGANISM: Homo sapiens

<400> SEQUENCE: 14
cagcacagta gggatcttcc gtacgcg                                27

<210> SEQ ID NO 15
<211> LENGTH: 408
<212> TYPE: DNA
<213> ORGANISM: Homo sapiens

<400> SEQUENCE: 15
atggctgtcc tggcgctact cctctgcctg atgactttcc caagctgtgc cctgtcccag    60
gtgcagctga aggagtcagg acctggcctg gtggcgccct cacagagcct gtccatcaca   120
tgcactgtct ctgggttctc attaaccaac tatgttataa gctgggttcg ccagccacca   180
ggaaagggtc tggagtggct tggagtaatt tggactggtg agacacaaa  ttataattca   240
gctctcaaat ccagactgag catcagcaaa gacaactcca agagtcaagt tttcttaaaa   300
atgaacagtc tgcaaactgg tgacacagcc aggtactact gtgccagagg gggacagctc   360
gggctacgtg gttattgggg ccaagggact ctggtcactg tctctgca               408

<210> SEQ ID NO 16
<211> LENGTH: 393
<212> TYPE: DNA
<213> ORGANISM: Homo sapiens

<400> SEQUENCE: 16
atggagacag acacactcct gttatgggta ctgctgctct gggttccagg ttccactggt    60
gacattgtgc taacacagtc tcctgcttcc ttagctgtat ctctggggca gagggccacc   120
atctcatgca gggccagcaa aactgtcagt tcatctggct atagttatat gcactggtac   180
caacagaaac caggacagcc acccaaactc ctcatctatc ttgcatccaa cctagaatct   240
ggggtccctg ccaggttcag tggcagtggg tctgggacag acttcaccct caacatccat   300
cctgtggagg aggaggatgc tgcaacctat tactgtcagc acagtaggga tcttccgtac   360
gcgttcggag gggggaccaa gttggaaata aaa                               393

<210> SEQ ID NO 17
<211> LENGTH: 527
<212> TYPE: PRT
<213> ORGANISM: Homo sapiens

<400> SEQUENCE: 17

Met Glu Ser Ala Ala Ala Leu His Phe Ser Arg Pro Ala Ser Leu Leu
1               5                   10                  15

Leu Leu Leu Leu Ser Leu Cys Ala Leu Val Ser Ala Gln Phe Ile Val
            20                  25                  30

Val Gly Pro Thr Asp Pro Ile Leu Ala Thr Val Gly Glu Asn Thr Thr
        35                  40                  45

Leu Arg Cys His Leu Ser Pro Glu Lys Asn Ala Glu Asp Met Glu Val
    50                  55                  60

Arg Trp Phe Arg Ser Gln Phe Ser Pro Ala Val Phe Val Tyr Lys Gly
65                  70                  75                  80

Gly Arg Glu Arg Thr Glu Glu Gln Met Glu Glu Tyr Arg Gly Arg Thr
                85                  90                  95

Thr Phe Val Ser Lys Asp Ile Ser Arg Gly Ser Val Ala Leu Val Ile
            100                 105                 110

His Asn Ile Thr Ala Gln Glu Asn Gly Thr Tyr Arg Cys Tyr Phe Gln
        115                 120                 125

Glu Gly Arg Ser Tyr Asp Glu Ala Ile Leu His Leu Val Ala Gly
        130                 135                 140

Leu Gly Ser Lys Pro Leu Ile Ser Met Arg Gly His Glu Asp Gly Gly
145                 150                 155                 160

Ile Arg Leu Glu Cys Ile Ser Arg Gly Trp Tyr Pro Lys Pro Leu Thr
                165                 170                 175

Val Trp Arg Asp Pro Tyr Gly Val Ala Pro Ala Leu Lys Glu Val
            180                 185                 190

Ser Met Pro Asp Ala Asp Gly Leu Phe Met Val Thr Thr Ala Val Ile
        195                 200                 205

Ile Arg Asp Lys Ser Val Arg Asn Met Ser Cys Ser Ile Asn Asn Thr
        210                 215                 220

Leu Leu Gly Gln Lys Lys Glu Ser Val Ile Phe Ile Pro Glu Ser Phe
225                 230                 235                 240

Met Pro Ser Val Ser Pro Cys Ala Val Ala Leu Pro Ile Ile Val Val
                245                 250                 255

Ile Leu Met Ile Pro Ile Ala Val Cys Ile Tyr Trp Ile Asn Lys Leu
                260                 265                 270

Gln Lys Glu Lys Lys Ile Leu Ser Gly Glu Lys Glu Phe Glu Arg Glu
        275                 280                 285

Thr Arg Glu Ile Ala Leu Lys Glu Leu Glu Lys Glu Arg Val Gln Lys
        290                 295                 300

Glu Glu Glu Leu Gln Val Lys Glu Lys Leu Gln Glu Glu Leu Arg Trp
305                 310                 315                 320

Arg Arg Thr Phe Leu His Ala Val Asp Val Leu Asp Pro Asp Thr
                325                 330                 335

Ala His Pro Asp Leu Phe Leu Ser Glu Asp Arg Arg Ser Val Arg Arg
                340                 345                 350

Cys Pro Phe Arg His Leu Gly Glu Ser Val Pro Asp Asn Pro Glu Arg
                355                 360                 365

Phe Asp Ser Gln Pro Cys Val Leu Gly Arg Glu Ser Phe Ala Ser Gly
        370                 375                 380

Lys His Tyr Trp Glu Val Glu Val Glu Asn Val Ile Glu Trp Thr Val
385                 390                 395                 400

Gly Val Cys Arg Asp Ser Val Glu Arg Lys Gly Glu Val Leu Leu Ile
                405                 410                 415

Pro Gln Asn Gly Phe Trp Thr Leu Glu Met His Lys Gly Gln Tyr Arg
                420                 425                 430

Ala Val Ser Ser Pro Asp Arg Ile Leu Pro Leu Lys Glu Ser Leu Cys
                435                 440                 445

Arg Val Gly Val Phe Leu Asp Tyr Glu Ala Gly Asp Val Ser Phe Tyr
        450                 455                 460

Asn Met Arg Asp Arg Ser His Ile Tyr Thr Cys Pro Arg Ser Ala Phe
465                 470                 475                 480

Ser Val Pro Val Arg Pro Phe Phe Arg Leu Gly Cys Glu Asp Ser Pro
                485                 490                 495

Ile Phe Ile Cys Pro Ala Leu Thr Gly Ala Asn Gly Val Thr Val Pro
                500                 505                 510

Glu Glu Gly Leu Thr Leu His Arg Val Gly Thr His Gln Ser Leu
        515                 520                 525

<210> SEQ ID NO 18
<211> LENGTH: 523

<212> TYPE: PRT
<213> ORGANISM: Homo sapiens

<400> SEQUENCE: 18

```
Met Glu Pro Ala Ala Ala Leu His Phe Ser Leu Pro Ala Ser Leu Leu
1               5                   10                  15

Leu Leu Leu Leu Leu Leu Leu Leu Ser Leu Cys Ala Leu Val Ser Ala
                20                  25                  30

Gln Phe Thr Val Val Gly Pro Ala Asn Pro Ile Leu Ala Met Val Gly
        35                  40                  45

Glu Asn Thr Thr Leu Arg Cys His Leu Ser Pro Glu Lys Asn Ala Glu
50                  55                  60

Asp Met Glu Val Arg Trp Phe Arg Ser Gln Phe Ser Pro Ala Val Phe
65                  70                  75                  80

Val Tyr Lys Gly Gly Arg Glu Arg Thr Glu Glu Gln Met Glu Glu Tyr
                85                  90                  95

Arg Gly Arg Ile Thr Phe Val Ser Lys Asp Ile Asn Arg Gly Ser Val
                100                 105                 110

Ala Leu Val Ile His Asn Val Thr Ala Gln Glu Asn Gly Ile Tyr Arg
                115                 120                 125

Cys Tyr Phe Gln Glu Gly Arg Ser Tyr Asp Glu Ala Ile Leu Arg Leu
130                 135                 140

Val Val Ala Gly Leu Gly Ser Lys Pro Leu Ile Glu Ile Lys Ala Gln
145                 150                 155                 160

Glu Asp Gly Ser Ile Trp Leu Glu Cys Ile Ser Gly Gly Trp Tyr Pro
                165                 170                 175

Glu Pro Leu Thr Val Trp Arg Asp Pro Tyr Gly Glu Val Val Pro Ala
                180                 185                 190

Leu Lys Glu Val Ser Ile Ala Asp Ala Asp Gly Leu Phe Met Val Thr
                195                 200                 205

Thr Ala Val Ile Ile Arg Asp Lys Tyr Val Arg Asn Val Ser Cys Ser
210                 215                 220

Val Asn Asn Thr Leu Leu Gly Gln Glu Lys Glu Thr Val Ile Phe Ile
225                 230                 235                 240

Pro Glu Ser Phe Met Pro Ser Ala Ser Pro Trp Met Val Ala Leu Ala
                245                 250                 255

Val Ile Leu Thr Ala Ser Pro Trp Met Val Ser Met Thr Val Ile Leu
                260                 265                 270

Ala Val Phe Ile Ile Phe Met Ala Val Ser Ile Cys Cys Ile Lys Lys
                275                 280                 285

Leu Gln Arg Glu Lys Lys Ile Leu Ser Gly Glu Lys Lys Val Glu Gln
290                 295                 300

Glu Glu Lys Glu Ile Ala Gln Gln Leu Gln Glu Glu Leu Arg Trp Arg
305                 310                 315                 320

Arg Thr Phe Leu His Ala Ala Asp Val Val Leu Asp Pro Asp Thr Ala
                325                 330                 335

His Pro Glu Leu Phe Leu Ser Glu Asp Arg Arg Ser Val Arg Arg Gly
                340                 345                 350

Pro Tyr Arg Gln Arg Val Pro Asp Asn Pro Glu Arg Phe Asp Ser Gln
                355                 360                 365

Pro Cys Val Leu Gly Trp Glu Ser Phe Ala Ser Gly Lys His Tyr Trp
370                 375                 380

Glu Val Glu Val Glu Asn Val Met Val Trp Thr Val Gly Val Cys Arg
385                 390                 395                 400
```

```
His Ser Val Glu Arg Lys Gly Glu Val Leu Leu Ile Pro Gln Asn Gly
                405                 410                 415

Phe Trp Thr Leu Glu Met Phe Gly Asn Gln Tyr Arg Ala Leu Ser Ser
            420                 425                 430

Pro Glu Arg Ile Leu Pro Leu Lys Glu Ser Leu Cys Arg Val Gly Val
            435                 440                 445

Phe Leu Asp Tyr Glu Ala Gly Asp Val Ser Phe Tyr Asn Met Arg Asp
    450                 455                 460

Arg Ser His Ile Tyr Thr Cys Pro Arg Ser Ala Phe Thr Val Pro Val
465                 470                 475                 480

Arg Pro Phe Phe Arg Leu Gly Ser Asp Asp Ser Pro Ile Phe Ile Cys
                485                 490                 495

Pro Ala Leu Thr Gly Ala Ser Gly Val Met Val Pro Glu Glu Gly Leu
            500                 505                 510

Lys Leu His Arg Val Gly Thr His Gln Ser Leu
            515                 520

<210> SEQ ID NO 19
<211> LENGTH: 137
<212> TYPE: PRT
<213> ORGANISM: Mus musculus

<400> SEQUENCE: 19

Met Gly Trp Asn Trp Ile Phe Ile Leu Ile Leu Ser Val Thr Thr Gly
1               5                   10                  15

Val His Ser Glu Val Gln Leu Gln Gln Ser Gly Pro Glu Leu Val Lys
            20                  25                  30

Pro Gly Ala Ser Val Lys Ile Ser Cys Lys Ala Ser Gly Tyr Ser Phe
        35                  40                  45

Thr Val Tyr Tyr Met Leu Trp Val Lys Gln Ser Pro Glu Lys Ser Leu
    50                  55                  60

Glu Trp Ile Gly Glu Ile Asn Pro Ser Thr Gly Gly Thr Thr Tyr Asn
65                  70                  75                  80

Gln Lys Phe Lys Ala Lys Ala Thr Leu Thr Val Asp Lys Ser Ser Ser
                85                  90                  95

Thr Ala Tyr Met Gln Leu Lys Ser Leu Thr Ser Glu Asp Ser Ala Val
            100                 105                 110

Tyr Tyr Cys Ala Arg Gly Pro Ser Phe Tyr Ala Leu Asp Tyr Trp Gly
        115                 120                 125

Gln Gly Thr Ser Val Thr Val Ser Ser
    130                 135

<210> SEQ ID NO 20
<211> LENGTH: 130
<212> TYPE: PRT
<213> ORGANISM: Mus musculus

<400> SEQUENCE: 20

Met Asp Phe Gln Met Gln Ile Ile Ser Leu Leu Leu Ile Ser Val Thr
1               5                   10                  15

Val Ile Val Ser His Gly Glu Ile Val Leu Thr Gln Ser Pro Thr Thr
            20                  25                  30

Met Ala Ala Ser Pro Gly Glu Lys Ile Thr Ile Thr Cys Ser Ala Thr
        35                  40                  45

Ser Ser Ile Ser Ser Asn Tyr Leu His Trp Tyr Arg His Lys Pro Gly
    50                  55                  60
```

Phe Ser Pro Lys Leu Leu Ile Tyr Arg Thr Ser Asn Leu Ala Ser Gly
65                  70                  75                  80

Val Pro Gly Arg Phe Ser Gly Ser Gly Ser Gly Thr Ser Tyr Ser Leu
                85                  90                  95

Thr Ile Gly Thr Met Glu Ala Glu Asp Val Ala Thr Tyr Tyr Cys Gln
            100                 105                 110

Gln Gly Ser Ser Ile Pro Arg Thr Phe Gly Gly Gly Thr Lys Leu Glu
        115                 120                 125

Ile Lys
    130

<210> SEQ ID NO 21
<211> LENGTH: 5
<212> TYPE: PRT
<213> ORGANISM: Mus musculus

<400> SEQUENCE: 21

Val Tyr Tyr Met Leu
1               5

<210> SEQ ID NO 22
<211> LENGTH: 17
<212> TYPE: PRT
<213> ORGANISM: Mus musculus

<400> SEQUENCE: 22

Glu Ile Asn Pro Ser Gly Gly Thr Thr Tyr Asn Gln Lys Phe Lys
1               5                   10                  15

Ala

<210> SEQ ID NO 23
<211> LENGTH: 9
<212> TYPE: PRT
<213> ORGANISM: Mus musculus

<400> SEQUENCE: 23

Gly Pro Ser Phe Tyr Ala Leu Asp Tyr
1               5

<210> SEQ ID NO 24
<211> LENGTH: 12
<212> TYPE: PRT
<213> ORGANISM: Mus musculus

<400> SEQUENCE: 24

Ser Ala Thr Ser Ser Ile Ser Ser Asn Tyr Leu His
1               5                   10

<210> SEQ ID NO 25
<211> LENGTH: 7
<212> TYPE: PRT
<213> ORGANISM: Mus musculus

<400> SEQUENCE: 25

Arg Thr Ser Asn Leu Ala Ser
1               5

<210> SEQ ID NO 26
<211> LENGTH: 9
<212> TYPE: PRT
<213> ORGANISM: Mus musculus

<400> SEQUENCE: 26

Gln Gln Gly Ser Ser Ile Pro Arg Thr
1               5

<210> SEQ ID NO 27
<211> LENGTH: 15
<212> TYPE: DNA
<213> ORGANISM: Mus musculus

<400> SEQUENCE: 27
gtctactaca tgctc                                              15

<210> SEQ ID NO 28
<211> LENGTH: 51
<212> TYPE: DNA
<213> ORGANISM: Mus musculus

<400> SEQUENCE: 28
gagattaatc ctagcactgg tggtactacc tacaaccaga agttcaaggc c       51

<210> SEQ ID NO 29
<211> LENGTH: 27
<212> TYPE: DNA
<213> ORGANISM: Mus musculus

<400> SEQUENCE: 29
ggcccgagct tttatgctct ggactac                                 27

<210> SEQ ID NO 30
<211> LENGTH: 36
<212> TYPE: DNA
<213> ORGANISM: Mus musculus

<400> SEQUENCE: 30
agtgccacct ctagtataag ttccaattac ttgcat                       36

<210> SEQ ID NO 31
<211> LENGTH: 21
<212> TYPE: DNA
<213> ORGANISM: Mus musculus

<400> SEQUENCE: 31
aggacatcca atctggcttc t                                       21

<210> SEQ ID NO 32
<211> LENGTH: 27
<212> TYPE: DNA
<213> ORGANISM: Mus musculus

<400> SEQUENCE: 32
cagcagggta gtagtatacc acgcacg                                 27

<210> SEQ ID NO 33
<211> LENGTH: 411
<212> TYPE: DNA
<213> ORGANISM: Mus musculus

<400> SEQUENCE: 33
atgggatgga actggatctt tattttaatc ctgtcagtaa ctacaggtgt ccactctgag    60
gtccagctgc agcagtctgg acctgagctg gtgaagcctg ggcttcagt gaagatatcc    120 tgcaaggctt ctggttactc attcactgtc tactacatgc tctgggtgaa acaaagtcct   180

-continued

```
gaaaagagcc ttgagtggat tggagagatt aatcctagca ctggtggtac tacctacaac      240
cagaagttca aggccaaggc cacattgact gtagacaaat cctccagcac agcctacatg      300
cagctcaaga gcctgacatc tgaggactct gcagtctatt actgtgcaag gggcccgagc      360
ttttatgctc tggactactg gggtcaagga acctcagtca ccgtctcctc a               411

<210> SEQ ID NO 34
<211> LENGTH: 390
<212> TYPE: DNA
<213> ORGANISM: Mus musculus

<400> SEQUENCE: 34
atggattttc agatgcagat tatcagcttg ctgctaatca gtgtcacagt catagtgtct       60
catggagaaa ttgtgctcac ccagtctcca accaccatgg ctgcatctcc cggggagaag      120
atcactatca cctgcagtgc cacctctagt ataagttcca attacttgca ttggtatcga      180
cataagccag gattctcccc taaactcttg atttatagga catccaatct ggcttctgga      240
gtcccaggtc gcttcagtgg cagtgggtct gggacctctt actctctcac aattggcacc      300
atggaggctg aagatgttgc cacttactac tgccagcagg gtagtagtat accacgcacg      360
ttcggagggg ggaccaagct ggaaataaaa                                        390

<210> SEQ ID NO 35
<211> LENGTH: 1083
<212> TYPE: PRT
<213> ORGANISM: Macaca fascicularis

<400> SEQUENCE: 35
```

Met Gln Arg Gln Phe Ser Lys Ala Ser Arg Pro Cys Leu Pro Trp Val
1               5                   10                  15

Leu Met Glu Pro Ala Ala Ala Leu His Phe Ser Leu Pro Ala Ser Leu
            20                  25                  30

Ile Leu Leu Leu Leu Leu Leu Arg Leu Cys Ala Leu Val Ser Ala Gln
        35                  40                  45

Phe Thr Val Val Gly Pro Thr Asp Pro Ile Leu Ala Met Val Gly Glu
    50                  55                  60

Asn Thr Thr Leu Arg Cys His Leu Ser Pro Glu Lys Asn Ala Glu Asp
65                  70                  75                  80

Met Glu Val Arg Trp Phe Arg Ser Gln Phe Ser Pro Ala Val Phe Val
                85                  90                  95

Tyr Lys Gly Gly Arg Glu Arg Thr Glu Glu Gln Met Glu Glu Tyr Arg
            100                 105                 110

Gly Arg Thr Thr Phe Val Ser Lys Asp Ile Ser Arg Gly Ser Val Ala
        115                 120                 125

Leu Ile Ile His Asn Val Thr Ala Gln Glu Asn Gly Thr Tyr Arg Cys
    130                 135                 140

Tyr Phe Gln Glu Gly Arg Ser Tyr Asp Glu Ala Ile Leu His Leu Met
145                 150                 155                 160

Val Ala Gly Leu Gly Ser Lys Pro Leu Val Glu Met Arg Gly His Glu
                165                 170                 175

Asp Gly Gly Ile Arg Leu Glu Cys Ile Ser Arg Gly Trp Tyr Pro Lys
            180                 185                 190

Pro Leu Thr Val Trp Arg Asp Pro Tyr Gly Arg Val Val Pro Ala Leu
        195                 200                 205

Lys Glu Val Phe Pro Pro Asp Thr Asp Gly Leu Phe Met Val Thr Thr
    210                 215                 220

-continued

```
Ala Val Ile Ile Arg Asp Lys Ser Met Arg Asn Met Ser Cys Ser Ile
225                 230                 235                 240

Ser Asp Thr Leu Leu Gly Gln Lys Lys Glu Ser Val Ile Phe Ile Pro
            245                 250                 255

Glu Ser Phe Met Pro Ser Val Ser Pro Cys Val Val Ala Leu Pro Ile
                260                 265                 270

Ile Val Val Phe Leu Met Ile Ile Ala Val Cys Ile Tyr Trp Ile
        275                 280                 285

Asn Arg Leu Gln Lys Glu Thr Lys Ile Leu Ser Gly Glu Lys Glu Ser
            290                 295                 300

Glu Arg Lys Thr Arg Glu Ile Ala Val Lys Leu Lys Lys Glu Arg
305                 310                 315                 320

Val Gln Lys Glu Lys Glu Leu Gln Val Lys Glu Gln Leu Gln Glu Glu
                325                 330                 335

Leu Arg Trp Arg Arg Thr Val Leu His Ala Val Asp Val Val Leu Asp
            340                 345                 350

Pro Asp Thr Ala His Pro Asp Leu Leu Leu Ser Glu Asp Arg Arg Ser
                355                 360                 365

Val Arg Arg Cys Pro Leu Gly His Leu Gly Glu Ser Val Pro Asp Asn
370                 375                 380

Pro Glu Arg Phe Asn Ser Glu Pro Cys Val Leu Gly Arg Glu Ser Phe
385                 390                 395                 400

Ala Ser Gly Lys His Tyr Trp Glu Val Glu Val Glu Asn Val Ile Glu
                405                 410                 415

Trp Thr Val Gly Val Cys Arg Asp Ser Val Glu Arg Lys Glu Glu Val
            420                 425                 430

Leu Leu Arg Pro Arg Asn Gly Phe Trp Thr Leu Glu Met Cys Lys Gly
            435                 440                 445

Gln Tyr Arg Ala Leu Ser Ser Pro Lys Arg Ile Leu Pro Leu Lys Glu
        450                 455                 460

Ser Leu Cys Arg Val Gly Val Phe Leu Asp Tyr Glu Ala Gly Asp Val
465                 470                 475                 480

Ser Phe Tyr Asn Met Arg Asp Arg Ser His Ile Tyr Thr Cys Pro Arg
                485                 490                 495

Leu Ala Phe Ser Val Pro Val Arg Pro Phe Phe Arg Ile Gly Ser Asp
                500                 505                 510

Asp Ser Pro Ile Phe Ile Cys Pro Ala Leu Thr Gly Ala Ser Gly Ile
            515                 520                 525

Thr Val Pro Glu Glu Gly Leu Ile Leu His Arg Val Gly Thr Asn Gln
            530                 535                 540

Ser Leu Met Pro Val Gly Thr Arg Cys Tyr Gly His Gly Met Arg Pro
545                 550                 555                 560

Thr Gly Phe Ile Arg Met Arg Glu Glu Arg Gly Ile His Arg Thr Thr
                565                 570                 575

Arg Glu Glu Arg Glu Pro Asp Met Gln Asn Phe Asp Leu Gly Ala His
                580                 585                 590

Trp Ser Asn Asn Leu Pro Ser Ala Arg Ser Arg Glu Phe Leu Asn Ser
            595                 600                 605

Asp Leu Val Pro Asp His Ser Leu Glu Ser Pro Val Thr Pro Gly Leu
        610                 615                 620

Ala Asn Lys Thr Gly Glu Pro Gln Ala Glu Val Thr Cys Leu Cys Phe
625                 630                 635                 640
```

-continued

```
Ser Leu Pro Ser Ser Glu Leu Arg Ala Phe Pro Ser Thr Ala Thr Asn
                645                 650                 655

His Asn His Lys Ala Thr Ala Leu Gly Ser Asp Leu His Ile Glu Val
            660                 665                 670

Lys Gly Tyr Glu Asp Gly Gly Ile His Leu Glu Cys Arg Ser Thr Gly
        675                 680                 685

Trp Tyr Pro Gln Pro Gln Ile Gln Trp Ser Asn Thr Lys Gly Gln His
690                 695                 700

Ile Pro Ala Val Lys Ala Pro Val Val Ala Asp Gly Val Gly Leu Tyr
705                 710                 715                 720

Ala Val Ala Ala Ser Val Ile Met Arg Gly Ser Gly Glu Gly Val
                725                 730                 735

Ser Cys Ile Ile Arg Asn Ser Leu Leu Gly Leu Glu Lys Thr Ala Ser
                740                 745                 750

Ile Ser Ile Thr Asp Pro Phe Phe Arg Asn Ala Gln Pro Trp Ile Ala
            755                 760                 765

Ala Leu Ala Gly Thr Leu Pro Ile Ser Leu Leu Leu Ala Gly Ala
        770                 775                 780

Ser Tyr Phe Leu Trp Arg Gln Gln Lys Glu Lys Ile Ala Leu Ser Arg
785                 790                 795                 800

Glu Thr Glu Arg Glu Arg Glu Met Lys Glu Met Gly Tyr Ala Ala Thr
                805                 810                 815

Lys Gln Glu Ile Ser Leu Arg Gly Gly Glu Lys Ser Leu Ala Tyr His
            820                 825                 830

Gly Thr His Ile Ser Tyr Leu Ala Ala Pro Glu Arg Trp Glu Met Ala
        835                 840                 845

Val Phe Pro Asn Ser Gly Leu Pro Arg Cys Leu Leu Thr Leu Ile Leu
850                 855                 860

Leu Gln Leu Pro Lys Leu Asp Ser Ala Pro Phe Asp Val Ile Gly Pro
865                 870                 875                 880

Pro Glu Pro Ile Leu Ala Val Val Gly Glu Asp Ala Glu Leu Pro Cys
                885                 890                 895

Arg Leu Ser Pro Asn Ala Ser Ala Glu His Leu Glu Leu Arg Trp Phe
            900                 905                 910

Arg Lys Lys Val Ser Pro Ala Val Leu Val His Arg Asp Gly Arg Glu
        915                 920                 925

Gln Glu Ala Glu Gln Met Pro Glu Tyr Arg Gly Arg Ala Thr Leu Val
930                 935                 940

Gln Asp Gly Ile Ala Glu Gly Arg Val Ala Leu Arg Ile Arg Gly Val
945                 950                 955                 960

Arg Val Ser Asp Asp Gly Glu Tyr Thr Cys Phe Phe Arg Glu Asp Gly
                965                 970                 975

Ser Tyr Glu Glu Ala Leu Val His Leu Lys Val Ala Ala Leu Gly Ser
            980                 985                 990

Asp Pro His Ile Ser Met Gln Val Gln Glu Asn Gly Glu Ile Trp Leu
        995                 1000                1005

Glu Cys Thr Ser Val Gly Trp Tyr Pro Glu Pro Gln Val Gln Trp
    1010                1015                1020
```

-continued

```
Arg Thr Ser Lys Gly Glu Lys Phe Pro Ser Thr Ser     Glu Ser Arg
    1025                1030                1035

Asn Pro Asp Glu Glu Gly Leu Phe Thr Val Ala Ala     Ser Val Ile
    1040                1045                1050

Ile Arg Asp Thr Ser Val Lys Asn Val Ser Cys Tyr     Ile Gln Asn
    1055                1060                1065

Leu Leu Leu Gly Gln Glu Lys Glu Val Glu Ile Phe     Ile Pro Gly
    1070                1075                1080
```